(12) United States Patent
Rangaramanujam et al.

(10) Patent No.: US 10,369,124 B2
(45) Date of Patent: Aug. 6, 2019

(54) DENDRIMER COMPOSITIONS AND THEIR USE IN TREATMENT OF DISEASES OF THE EYE

(71) Applicant: The Johns Hopkins University, Baltimore, MD (US)

(72) Inventors: Kannan Rangaramanujam, Highland, MD (US); Gerard Lutty, Hyattsville, MD (US); Siva Pramodh Kambhampati, Baltimore, MD (US); Manof Mishra, Ellicott City, MD (US); Imran Bhutto, Nottingham, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/307,284

(22) PCT Filed: Apr. 30, 2015

(86) PCT No.: PCT/US2015/028386
§ 371 (c)(1),
(2) Date: Oct. 27, 2016

(87) PCT Pub. No.: WO2015/168347
PCT Pub. Date: Nov. 5, 2015

(65) Prior Publication Data
US 2017/0043027 A1 Feb. 16, 2017

Related U.S. Application Data

(60) Provisional application No. 61/986,495, filed on Apr. 30, 2014.

(51) Int. Cl.
*A61K 49/00* (2006.01)
*A61K 9/00* (2006.01)
(Continued)

(52) U.S. Cl.
CPC .......... *A61K 31/198* (2013.01); *A61K 9/0019* (2013.01); *A61K 9/0048* (2013.01);
(Continued)

(58) Field of Classification Search
None
See application file for complete search history.

(56) References Cited

U.S. PATENT DOCUMENTS

| | | | |
|---|---|---|---|
| 4,507,466 | A | 3/1985 | Tomalia |
| 4,558,120 | A | 12/1985 | Tomalia |

(Continued)

FOREIGN PATENT DOCUMENTS

| | | |
|---|---|---|
| EP | 1639029 | 7/2007 |
| WO | 0018394 | 4/2000 |

(Continued)

OTHER PUBLICATIONS

Kurtoglu, Yunus E., et al. "Drug release characteristics of Pamam dendrimer—drug conjugates with different linkers." International journal of pharmaceutics 384.1 (2010): 189-194.*

(Continued)

*Primary Examiner* — Nissa M Westerberg
(74) *Attorney, Agent, or Firm* — Pabst Patent Group LLP

(57) ABSTRACT

The treatment of many ocular disorders is hampered because of poor penetration of systemically administered drugs into the eye. The tight junctional complexes (zonulae occludens) of the retinal pigment epithelium and retinal capillaries are the site of the blood-ocular barrier. This barrier inhibits penetration of substances, including antibiotics, into the vitreous. Over the last 18 years we have evaluated the nontoxic doses of various drugs. These include antibiotics and antifungals for treatment of bacterial and fungal endophthalmitis, antivirals for treatment of viral retinitis (specifically, when medication with these drugs poses the (Continued)

threat of toxicity to other organs). Intravitreal antineoplastic drugs have been studied to prevent cell proliferation in the vitreous cavity after retinal attachment surgery, which can lead to proliferative vitreoretinopathy (PVR). Furthermore, we evaluated the anti-inflammatory action of dexamethasone and cyclosporine A to reduce intraocular inflammation after intraocular surgery or in uveitis. Because these studies had been performed in the presence of the vitreous, which can slow down the diffusion of the drugs toward the retina, it was necessary to reevaluate the concentration of drugs which could be administered intravitreally in the vitrectomized eye. The nontoxic dose of numerous drugs when added to vitrectomy infusion fluid has also been evaluated. Furthermore, the role of vitrectomy in the treatment of bacterial fungal endophthalmitis has been studied and the role of vitrectomy in this ocular disorder is defined.

13 Claims, 24 Drawing Sheets

(51) Int. Cl.
| | | |
|---|---|---|
| *A61K 31/198* | (2006.01) | |
| *A61K 9/08* | (2006.01) | |
| *A61K 31/573* | (2006.01) | |
| *A61K 45/06* | (2006.01) | |
| *A61K 47/59* | (2017.01) | |

(52) U.S. Cl.
CPC .............. *A61K 9/08* (2013.01); *A61K 31/573* (2013.01); *A61K 45/06* (2013.01); *A61K 47/595* (2017.08); *A61K 49/0032* (2013.01); *A61K 49/0054* (2013.01)

(56) References Cited

U.S. PATENT DOCUMENTS

| | | |
|---|---|---|
| 4,568,737 A | 2/1986 | Tomalia |
| 4,587,329 A | 5/1986 | Tomalia |
| 5,714,166 A | 2/1998 | Tomalia |
| 5,968,979 A | 10/1999 | Brusilow |
| 8,148,356 B2 | 4/2012 | Pavliv |
| 8,399,445 B2 | 3/2013 | Pavliv |
| 8,404,215 B1 | 3/2013 | Scharschmidt |
| 8,427,225 B2 | 4/2013 | Nakatake |
| 8,642,012 B2 | 2/2014 | Scharschmidt |
| 8,653,061 B2 | 2/2014 | Pavliv |
| 8,722,738 B2 | 5/2014 | Pavliv |
| 8,889,101 B2 | 11/2014 | Kannan |
| 9,095,559 B2 | 8/2015 | Scharschmidt |
| 2002/0068795 A1 | 6/2002 | Won |
| 2002/0192843 A1 | 12/2002 | Kaganove |
| 2003/0135005 A1 | 7/2003 | Houser |
| 2003/0180250 A1 | 9/2003 | Chauhan |
| 2004/0151754 A1 | 8/2004 | Ashton |
| 2006/0041058 A1 | 2/2006 | Yin |
| 2006/0240110 A1 | 10/2006 | Kiick |
| 2007/0088014 A1 | 4/2007 | Edelman |
| 2007/0128681 A1 | 6/2007 | Barman |
| 2007/0298006 A1 | 12/2007 | Tomalia |
| 2008/0031848 A1 | 2/2008 | Konradi |
| 2009/0104123 A1 | 4/2009 | Yang |
| 2011/0034422 A1 | 2/2011 | Kannan |
| 2012/0003155 A1 | 1/2012 | Kannan |
| 2013/0123330 A1 | 5/2013 | Lu |
| 2015/0352230 A1 | 12/2015 | Mullen |

FOREIGN PATENT DOCUMENTS

| | | |
|---|---|---|
| WO | 2003080121 | 10/2003 |
| WO | 2004041310 | 5/2004 |
| WO | 2005055926 | 11/2004 |
| WO | 2004106411 | 12/2004 |
| WO | 2006033766 | 3/2006 |
| WO | 2007089607 | 8/2007 |
| WO | 2008068531 | 6/2008 |
| WO | 2009046446 | 4/2009 |
| WO | 2009142754 | 1/2010 |
| WO | 2010017181 | 2/2010 |
| WO | 2010147831 | 12/2010 |
| WO | 2011011384 | 7/2011 |
| WO | 2011123591 | 10/2011 |
| WO | 2014197909 | 12/2014 |
| WO | 2015027068 | 2/2015 |
| WO | 2015038493 | 3/2015 |
| WO | 2015168347 | 11/2015 |
| WO | 2014178892 | 12/2015 |
| WO | 2016025745 | 4/2016 |

OTHER PUBLICATIONS

Jonas, J. B., et al. "Intravitreal triamcinolone acetonide for exudative age related macular degeneration." British Journal of Ophthalmology 87.4 (2003): 462-468.*
Akaishi, et al., "Quantitative Analysis of Major Histocompatibility Complex Class 11-Positive Cells in Posterior Segment of Royal College of Surgeons Rat Eyes," Jpn. J. Ophthalmology, 42:357-62 (1998).
Akinc, et al., "Exploring polyethylenimine-mediated DNA transfection and the proton sponge hypothesis", J Gene Med, . 7(5): 657-63 (2005).
Alexandre, et al., "Accumulation of hydrogen peroxide is an early and crucial step for paclitaxel-induced cancer cell death both in vitro and in vivo", Int. J. Cancer, 19:41-8 (2006).
Allard, et al., "Convection-enhanced delivery of nanocarriers for the treatment of brain tumors", Biomaterials, 30(12):2302-18 (2009).
Almutairi, et al., "Biodegradable dendritic position emittinf nanoprobes for the nominvasive Imaging of angiogenesis", PNAS, 106(3):685-90 (2009).
Almutairi, et al., "Monitoring the biodfgradation of dendritic nrear-infrared nanoprobes by in vivo fluorescence imaging", Mol Pharm., 5(6):1103-10 (2008).
Alving, et al., "Therapy of leishmaniasis: Superior efficacies of liposome-encapsulated drugs", PNAS, 75(6):2959-63 (1978).
Antoni, et al., "A chemoselective approach for the accelerated synthesis of well-defined dendritic architectures", Chem Commun (Camb), 22(22):2249-51 (2007).
Antoni,et al., "Bifunctional dendrimers: from robust synthesis and accelerated one-pot postfunctionalization strategy to potential applications", Angew Chem Int Ed Engl, 48(12):2126-30 (2009).
Arrick and Nathan, "Glutathione metabolism as a determinant of therapeutic efficacy: a review", Cancer Res., 44:d224-32 (1984).
Aslam, et al., "Antibacterial and antifungal activity of cicerfuran and related 2-arylbenz.ofurans and stilbenes", Microbiol Res., 164:191-5 (2009).
Augustin, et al., "Effects of Allopurinol and Steroids on Inflammation and OxidativeTissue Damage in Experimental Lens Induced Uveitis: A Biochemical and Morphological Study," Br. J. Ophthalmol. 80(5):451-7 (1996).
Baek, et al., "Sybthesis and protein binding properties of T-antigen containing glycoPAMAM dendrimers", Bioorganic Med Chem., 10(1):11-7 (2002).
Ballatori, "N-Acetyl cystelne as an antidote in methyl mercury poisoning", EnViron. Health Perspect., 106 (5):267-71 (1998).
Balogh, et al., "Dendrimer-Silver Complexes and Nanocomposites as Antimicrobial Agents", Nano Lett., 1:18-21 (2001).
Barrett, et al., "Dendrimers in medical nanotechnology", Eng Med Biol Mag., 28(1):12-22 (2009).
Behl, et al., "Neuroprotection Against Oxidative Stress by Estrogens: Structure-Activity Relationship," Mol. Pharmacol. 51(4):535-41 (1997).
Bell , et al., "Effects of Intrauterine Inflammation on Developing Rat Brain," J. Neurosci.Res., 70:570-9 (2002).

(56) References Cited

OTHER PUBLICATIONS

Bellair, et al., "Investigation of clay modifier effects on the structure and rheology of supercritical carbon dioxide processed polymer nanocomposites", J Polymer Sci Part B, 48(8):823-31 (2010).
Beloosesky, et al., "Maternal N-acetyl cys1ein suppress fetal inflammatory cytokine responses to material lipopolysaccharide", Am J Obstet Gynenol., 195:1053-7 (2006).
Beloosesky, et al., "N-acetylcysteine suppresses amniotic fluid and placenta inflammatory cytokine responses to lipopolysaccharide in rats", Am. J Obstet. Gynecol., 194:268-73 (2006b).
Ben-Ari, "N-acetylcysteine in acute hepatic failure (non-paracetamol-induced)", Hepatogastreonterology, 47(33):786-9 (2000).
Bennewitz, et al., "Nanotechnology for delivery of drugs to the brain for epilepsy", Neurotherapeutics, 6(2):323-36 (2009).
Benz, "Strcture and faction of porins from gram negative bacteria", Microbial., 42:359-93 (1998).
Berger, et al., "Pathophysiology of X-linked adrenoleukodystrophy", Biochimie, 98:135-42 (2014).
Berk, et al., "The promise of N-acetylcysteine in neuropsychiatry", Trends Pharma Sci., 34(3):167-77 (2013).
Bickel, et al., "Delivery of peptides and proteins through the blood-brain barrier",, Adv Drug Deliv Rev., 46:247-79 (2001).
Billiards, et al., "Development of microglia in the cerebral white matter of the human fetus and infant", J Comp Neurol., 497:199-208 (2006).
Block, et al., "Microglia-mediated neurotoxicity: uncovering the molecular mechanisms", Nat Rev Neurosci., 8:57-69 (2007).
Borgstrom, et al., "Pharmacokinetics of N-acetylcysteine in man", Eu J Clin Pharmacol., 31:217-22 (1986).
Bosnjkovic, "A dendrimer-based immunosensor for improved capture and detection of tumor necrosis factor-alpha cytokine", Analytical Achiica Acta, 720:118-25 (2012).
Bosnjkovic, et al., "Poly(amidoamine) dendrimer-erythromycin conjugates for drug delivery to macrophages involved in periprosthetic inflammation", Nanomedicine Nanotech Biol Med., 7(3):284 (2011).
Bourges, et al., "Ocular Drug Delivery Targeting The Retina and Retinal PigmentEpithelium Using Polylactide Nanoparticles," Invest. Opthalmol. & Vis. Sci., 44:3562-9 (2003).
Bourne, et al., "Dendrimers, a new class of candidate topical microbicides with activity against herpes simplex virus infection", Antimicrobial Agents Chemotherapy, 44:2471-4 (2000).
Bracci, et al., "Synthetic peptides in the form of dendrimers become resistant to protease activity", J Biol Chem.,278:46590-5 (2003).
Brauge, et al., "First divergent strategy using two AB(2) unprotected monomers for the rapid synthesis of dendrimers", J Am Chem Soc.,123(27):6698-9 (2001).
Breitkreutz, et al., "Improvement of immune functions of HIV infection by sulfur supplementation: two randomized trails", J Mol Med., 78:55-62 (2000).
Buddi, et al., "Emerging treatments for diabetic eye disease: Update on clinical trials", http://www.retinalphysican.com/articleviewer.aspx?articleID=100022 . Retinal Physician, Accessed on line May 2, 2015.
Buhimschi, et al., "Protective effect of n-acetylcysteine against fetal death and preterm labor induced by matemal inflammation", Am K Obstet Gynecol., 188:203-8 (2003).
Cakara, et al., "Microscopic M, Protonation Mechanism of Branched Polyamines: Poly(amidoamine) versus Poly(propyleneimine] Dendrimers Croat", Chem Acta., 80:421-8 (2007).
Cakara, et al., "Microscopic Protonation Equilibria of Poly(amidoamine) Dendrimers from Macroscopic Titrations", Macromolecules, 36:4201-7 (2003).
Calabretta, et al., "Antibacterial activities of poly(amidoamine) dendrimers terminated with amino and poly(ethylene 8 ycol) groups", Biomacromolecules, 8:1807-11 (2007).
Carbonell, et al., "Migration of perilesional microglia after focal brain injury and modulation by CC chemokine receptor 5: an in situ time-lapse confocal imaging study", J Neurosci., 27:30):7040-7 (2005).

Carmody, et al., "Reactive Oxygen Species as Mediators of Photoreceptor Apoptosisln Vitro," Exp. Cell Res. 248(2):520-30 (1999).
Cerqueira, et al., "Microglia response and in vivo therapeutic potential of methylprednisolone-loaded dendrimer nanoparticles in spinal cord injury", Nanoparticles, 5:738-49 (2013).
Chaim,et al, "The relationship between bacterial vaginosis and preterm birth: A Review", Archives Gen Obst, 259:51-8 (1997).
Chandrasekar, et al., "The development of folate-Pamam dendrimer conjugates for targeted delivery of anti-arthritic drugs and their pharmacokinetics and biodtstribution in arthritic rats", Biomaterials, 28(3):504-12 (2007).
Chang, et al., "Effects of Glucocorticoids on Fas Gene Expression in Bovine Blood Neutrophils," J. Endocrinol. 183:569-83 (2004).
Chang, et al., "Inhibition of Microglial Nitric Oxide Production by Hydrocortisone and Glucocorticoid Precursors," Neurochem Res. 25(7):903-8 (2000).
Chang, et al., "Minocycline Partially Inhibits Caspase-3 Activation and Photoreceptor Degeneration After Photic Injury," Ophthalmic Res. 37:202-13 (2005).
Chauhan, et al., "Solubility enhancement of indomethacin with poly(amidoamine) dendrimers and targeting to inflammatory regions of arthritic rats", J Drug Targeting, 12(9-10):575-83 (2004).
Chen, "Quaternary annonium functionalized poly(propylene omine) dendrimers as effective antimicrobials structur-activity studies", Biomacromolecules, 1:473-82 (2000).
Chen, et al., "Interactions between dendrimer biocides and vacterial membranes", Biomaterials, 23:3359-68 (2002).
Chen, et at.,"Interaction of Dendrimers (Artificial Proteins) with Biological Hydroxyapatite Crystals", J. Dent. Res., 82(6):443-8 (2003).
Cheng, et al., "Pharmaceutical applications of dendrimers: promising nanocarriers for drug delivery", Front. Biosci., 13:1447-71 (2008).
Cheng, et al., "Polyamidoamine (PAMAM) dendrimers as biocompatible carriers of quinolone antimicrobials: An invitro study", Eur J Med Chem., 42:1032-8 (2007).
Choi, et al., "Dexamethasone conjugated poly(amidoamine) dendrimer as a gene carrier for efficient nuclear translocation", Int J Pharma, 320:171-8 (2006).
Chow, et al., "Synthesis and Characterization of Outer Sphereâ'Outer Sphere Connected Organoplatinum Dendritic Networks from Surface-Difunctionalized and Surface-Trifunctionalized Dendritic Monomers", Macromolecules, 37(10):3595-605 (2004).
Cloninger, "Biological applications of dendrimers", Curr Opin Chem Biol., 6:742-8 (2002).
Cox, "Glucocorticoid Treatment Inhibits Apoptosis in Human Neutrophils. Separation of Survival and Activation Outcomes," J. Immunol., 154:4719-25 (1995).
Cuchelkar, et al., "Synthesis and biological evaluation of disulfide-linked HPMA copolymer—mesochlorin e6 conjugates", Macromcl Biesci., 8:375-B3 (2008).
Dai, et al., "Intrinsic targeting of inflammatory cells in the brain-subarachnoid administration", Nanomedicine, 5(9):1317-29 (2010).
Darbre and Reymond, "Peptide Dendrimers as Artificial Enzymes, Receptors, and Drug-Delivery Agents", Accounts Chem Res., 39(12):925-34 (2006).
De Kozak, et al., "Tumor Necrosis Factor and Nitric Oxide Production by Resident Retinal Glial Cells From Rats Presenting Hereditary Retinal Degeneration," Ocul. Immunol. Inflamm. 5(2):85-94 (1997).
De Jesus, et al., "Polyester dendritic systems for drug delivery applications: in vitro and in vivo evaluation", Bioconjug Chem., 13:453-61 (2002).
De Vries, et al., "The blood-brain barrier in neuroinflammatory diseases", Pharma Rev., 49:143-55 (1997).
Dekhuijzen, "Antiosidant properties of N-acetyl cysteine. their relevance in relation to chronic obstructive pulmonary oisease", Eur Respir J., 23:629-36 (2004).
Dennig, et al., "Gene transfer into eukaryotic cells using activated polyamidoamine dendrimers", Mole Biotrch., 90:339-47 (2002).

(56) References Cited

OTHER PUBLICATIONS

Desai, et al., "Synthesis and characterization of photocurable polyamidoamine dendrimer hydrogels as a versatile platform for tissue engineering and drug delivery", Biomacromolecules, 11(3):666-73 (2010).

Di Biase, et al., "Free radical release in C6 glial cells enriched in hexacosanoic acid: implication for X-linked adrenoleukodystrophy pathogenesis", Neurochem. Int. 44:215-21 (2004).

Dickinson, et al., "Transient lipopolysaccharide-induced cytokine responses in the material serum and amniotic fluid of the guinea pig", Am J Obst Gyn, 200:531-34 (2009).

Dierks, et al., "Electroretinographic Effects of an intravitreal Injection of Triamcinolone in Rabbit Retina," Arch. Ophthalmol. 123(11):1563-69 (2005).

Dilger and Baker, "Oral N-acetyl L-cysteine is a safe and effective precursor of cysteine", J. Anim. Sci., J9:1-26 (2007b).

Dilger, et al., "Excess dietary L-cysteine, but not L-cystine, is lethal for chicks but not for rats or dogs", J Nutrition, 322:331-8 (2007).

Dinkel et al., "Novel Glucocorticoid Effects on Acute Inflammation in The CNS," J.Neurochem. 84(4):705-16 (2003).

Dodd, et al., "Putative neuroprotective agents in neuropsychiatric disorders", Progress in Neuro-Psychopharmacology & Biological Psychiatry, 42:135-45 (2003).

Downs, et al., "Long-Term Safety of Repeated Blood-Brain Barrier Opening via Focused Ultrasound with Microbubbles in Non-Human Primates Performing a Cognitive Task", Plos One, 10(5):e0125911 (2015).

Drew, et al., "Inhibition of Microglial Cell Activation by Cortisol," Brain Res. Bull.52(5):391-6 (2000).

Dumont, et al., "Bezafibrate administration improves behavioral deficits and tau pathology in P301S mice", Hum Mol Genet., 21(23):5091-5105 (2012).

Duncan and Izzo, "Dendrimer biocompatibility and toxicity", Adv Drug Deliv Rev., 57:2215-37 (2005).

Duncan, "The dawning era of polymer therapeutics", Nature Reviews, 2:347-60 (2003).

Dunlap, et al., "Nanoscopic structure of DNA condensed for gene delivery", Nucleic Acids Res, . 25(15):3095-101 (1997).

Dutta, et al ., "Poly(propyleneimine) dendrimer and dendrosome mediated genetic immunization against hepatitis B", Vaccine, 26:3389-94 (2008).

Eichler, et al., "Is microglial apoptosis an early pathogenic change in cerebral X-linked adrenoleukodystrophy", Ann Neurol., 63(6):729-42 (2008).

El-Remessy, et al., "Neuroproteclive effects of cannabi diol in endotoxin-induced uveilis: critical role of p38 MAPK activation", Mol. Vis., 14:2190-203 (2008).

Ellison, et al., "Damage of the outer membrane of enteric gram-negative bacteria by lactoferrin and transferrin", Infect Immun., 56:2774-81 (1988).

Engelen, et al., "Bezafibrate for X-linked adrenoleukodystrophy", PloS one, 7(7):e41013 (2012c).

Engelen, et al., "Bezafibrate lowers very long-chain fatty acids in X-linked adrenoleukodystrophy fibroblasts by inhibiting fatty acid elong", J Inherit Metab Dis., 35(6):1137-45 (2012).

Engelen, et al., "X-linked adrenoleukodystrophy (X-ALD): clinical presentation and guidelines for diagnosis, follow-up and management", Orphanet J Rare Dis., 7:51 (2012b).

Esfand, et Al., "Poly(amidoamine) (PAMAM) dendrimers: from biomimicry to drug delivery and biomediCBI applications", Drug Discov Today, 6:427-36 (2001).

Estensen, et al., "N-Acetyl cysteine suppression of the proliferative index in the colon of patients with previous adenomatous colonic polyps", Cancer Lett., 147:109-14 (1999).

Ethier-Chiasson, et al., "Modulation of placental pro1ein expression of OLR1: implication in pregnancy-related disorders", Reproduction, 136: 491-502 (2008).

Eversole, et al., "Protective Effect of The 21-Aminosteroid Lipid Peroxidation InhibitorTirilazad Mesylate (U74006F) on Hepatic Endothelium in Experimental Hemorrhagic Shock," Circ. Shock 40(2):125-31 (1993).

Eye Disorders, mMerck Manual Home Edition, Merck Sharp & Dohme Corp. 2010-2011, 9 pgs, http://www.merckmanuals.com/home/eye_disorders.html, accessed on Jan. 23, 2013.

Fang, et al., "Host—guest chemistry of dendrimer-drug complexes: 7. Formation of stable inclusions between acetylated dendrimers and drugs bearing multiple charges", J Phys Chem B, 116:3075-82 (2012).

Ferrari, et al., "NAcetylcysteine (D- and L-stereoisomers) prevents apoptotic death of neuronal cells", J Neurosci., 15:2857-66 (1995).

Filipovska, et al., "Delivery of antisense peptide nucleic acids (PNAs) to the cytosol by disulphide conjugation to a lipophilic cation", FFBS Lett., 556:180-6 (2004).

Fischer-Durand, et al., "Design of a New Multifunctionalized PAMAM Dendrimer with Hydrazide-Terminated Spacer Arm Suitable for Metalâ'Carbonyl Multilabeling of Aldehyde-Containing Molecules", Macromolecules, 40(24):8568-75 (2007).

Flora, et al., "Lead induced oxidative stress and its recovery following co-administration of melatonin or N-acetyl cysteine during chelation with succimer in male rats", Cell Mol Biol., 50: 543-5 (2004).

Fourcade, et al., "Early oxidative damage underlying neurodegeneration in X-adrenoleukodystrophy", Hum. Mol. Genet., 17:1762-73 (2008).

Fourcade, et al., "Thyroid hormone induction of the adrenoleukodystrophy-related gene (ABCD2)", Mol Pharma., 63(6):1296-303 (2003).

Fremount, "Biological effects of resveratrol", Life Sci., 66(8):663-73 (2000).

Fuchs, et al., "A surface-modified dendrimer set for potential application as drug delivery vehicles: synthesis, in vitro toxicity, and intracellular localization", Chemistry,10 (5):1167-92 (2004).

Fujiki, et al., "Peroxisome biogenesis in mammalian cells", Front Physiol., 5:307 (2014).

Fung, et al., "Chemotherapeutic drugs released from polymers: distribution of 1,3-bis(2-chloroethyl)-1-nitrosourea in the rat brain", Pharm Res., 13:671-82 (1996).

Gal, et al., "Mutations In MERTK, The Human Orthologue of The RCS Rat RetinalDystrophy Gene, Cause Retinitis Pigmentosa," Nat.. Genet. 26(3):270-1 (2000).

Galea, et al., "Oxidative stress underlying axonal degeneration in adrenoleukodystrophy: a paradigm for multifactorial neurodegenerative diseases", Biochim Biophys Acta., 1822(9):1475-88 (2012).

Galino, et al., "Oxidative damage compromises energy metabolism in the axonal degeneration mouse model of X-adrenoleukodystrophy", Antioxid Redox Signal., 15(8):2095-107 (2011).

Gibson, et al., "Recent advances in topical therapeutics for vitreoretinal diseases", US Ophthalmic Review, 8(1) (2015).

Gillies and Frechet, "Dendrimers and dendritic polymers in drug delivery", Drug Dlivery Today, 10:35-43 (2005).

Gillies, et al. "Pioglitazone," Drugs, 60(2):333-43 (2000).

Girt, et al., "Stimuli-responsive controlled-release delivery system based on mesoporous silica nanorods capped with magnetic nanoparticles", Angew. Chem., Int Ed. 44:5038-44 (2005).

Glezer, et al., "Glucocorticoids: Protectors of the Brain During Innate Immune Responses," Neuroscientist 10(6):538-52 ( 2004).

Gomez, et al., "Antibiotic administration to patients with preterm premature rupture of membranes does not eradicate intra-amniotic infection", J. Matern. Fetal Neonatal Med. 20: 167-73 (2007).

Gondcaille, et al., "Phenylbutyrate up-regulates the adrenoleukodystrophy-related gene as a nonclassical peroxisome proliferator", J Cell Biol., 169(1):93-104 (2005).

Gonzalez, et al., "Glucocorticoids Antagonize AP-1 by Inhibiting the Activation/ Phosphorylation of JNK Without Affecting Its Subcellular Distribution," J.Cell Biol. 150(5):1199-208 (2000).

Good, et al., "Lactobacillus rhamnosus HN001 decreases the severity of necrotizing enterocolitis in neonatal mice and preterm piglets: evidence in mice for a role of TLR9", Am J Physiol Gastrointest Liver Physiol., 306(11):G1021-32 (2014).

(56) References Cited

OTHER PUBLICATIONS

Goodwin, et al., "Rapid, Efficient Synthesis of Heterobifunctional Biodegradable Dendrimers", J Am Chem Soc.,129(22):6994-5 (2007).
Goyal, et al., "Multifunctionalization of dendrimers through orthogonal transformations", Chemistry, 13(31):8801-10 (2007).
Green and Kroemer, "The Pathophysiology of Mitochondrial Cell Death," Science,305(5684):626-9 (2004).
Grinstaff, "Designing hydrogel adhesives for corneal wound repair", Biomaterials, 28(35):5205-14 (2007).
Gupta , et al., "Activated Microglia in Human Retinitis Pigmentosa, Late-Onset RetinalDegeneration, and Age-Related Macular Degeneration," Exp. Eye Res. 76(4):463-71 (2003).
Gurdag, "Activity of dendrimer-methotrexate conjugates on methotrexate-sensitive and resistant cell lines", Bioconjugate Chem., 17:275-83 (2006).
Halford, "Dendr mers branch out", C& EN, 83:30-6 (2005).
Hall, et al., "Antioxidant effects in brain and spinal cord injury", J Neurotrauma, 9(sup 1):165-72 (1992).
Han, et al., "Multifunctional Dendrimer-Templated Antibody Presentation on Biosensor Surfaces for Improved Biomarker Detection", Adv. Funct. Mater., 20:409-21 (2010).
Harada, et al., "Kinetic analysis of covalent binding between N-acetyl-L-cysteine and albumin through the formation of mixed disulfides in human and rat serum in vitro", Pharm Res., 19:1648-54 (2002).
Harnett, et al., "Dose-dependent lipopolysaccharide-induced fetal brain injury in guinea pig", Am J Obstetrics Gyngcol., 197:179 e171 177 (2007).
Heier, et al, "VBP15, a novel anti-inflammatory and membrane-stabilizer, improves muscular dystrophy without side effects", EMBO Mol Med., 5(10): 1569-85 (2013).
Helander, et al., "Fluorometric assessment of gram-negative bacterial permeabilization", J Appl Microbiol, 88:213-9 (2000).
Higdon, et al., "Resveratrol," Linus Pauling Institute Micronutrient Information Center, http://lpi.oregonstate.edu/mic/dietary-factors/phytochemicals/resveratrol, accessed (Oct. 2015).
Hinman, et al., "Upeelacis, Preparation and characterization of monoclonal antibody conjugates of the calicheamicins: A novel and potent family of antitumor antibiotics", J. Cancer Res. 53: 3336-42 (1993).
Hollins, et al., "Toxicogenomics of drug delivery systems: exploiting delivery system-induced changes in target gene expression to enhance siRNA activity", J Drug Targeting, 15:83-8 (2007).
Hong, et al., "Glutathione-mediated delivery and release using monolayer protected nanoparticle carriers", J Am. Chem Soc., 128:1078-9 (2006).
Hong, et al., "Interaction of polycationic polymers with supported lipid bilayers and cells: nanoscale hole formation and enhanced membrane permeability", Bioconjug Chem., 17:728-34 (2006b).
Horwitz , et al., "Efficacy of Lipid Soluble, Membrane-Protective Agents Against Hydrogen Peroxide Cytotoxicity in Cardiac Myocytes," Free Radic. Biol. Med. 21 (6):743-53 (1996).
Hou., et al., "Antimicrobial dendrimer active against *Escherichia coli* biofilms", Bioorg Med Chem Lett, 19:5478-81 (2009).
Huang, et al., "Efficient gene delivery targeted to the brain using a transferrin-conjugated polyethyleneglycol-modified polyamidoamine dendrimer", FASEB, 21(4):1117-25 (2007).
Hughes , et al., "Minocycline Delays Photoreceptor Death in the RDS Mouse Through a Microglia-Independent Mechanism," Exp. Eye Res. 78(6):1077-84 (2004).
Ibrahim, et al., "Antimicrobial Effects of Lysozyme against Gram-Negative Bacteria Due to Covalent Binding of Palmitic Acid", J Agnc Food Chem., 39:, 2077-82 (1991).
Iezzi, et al., "Dendrimer-based targeted intravitreal therapy for sustained attenuation of neuroinflammation in retinal degeneration", Biomaterials, 33(3):979-88 (2012).
Ignarro, "Lysosome Membrane Stabilization In Vivo: Effects of Steroidal and Nonsteroidal Anti-Inflammatory Drugs on the Integrity of Rat Liver Lysosomes," J.Pharmacol Exp. Ther. 182(1):179-88 (1972).

Inapagollo, "In vivo efficacy of dendrimer-methylprednisolone conjugate formulation for the treatment of lung inflammation", Intl J Pharma., 399(1-2):140-7 (2010).
Islam, et al., "HPLC Separation of Different Generations of Poly(Amidoamine) Dendrimers Modified With Various Terminal Groups," Anal. Chem. 77:2063-70 (2005).
Islam, et al., "Controlling the cytokine storm in severe bacterial diarrhoea with an oral toll-like receptor 4 antagonist", Immunology, 147:178-89 (2015).
Jaffe , et al., "Fluocinolone Acetonide Implant (Retisert) For Non-infectious Posterior Uveitis: Thirty-Four-Week Results of A Multi-center Randomized Clinical Study," Ophthalmol. 113:1020-7 (2006).
Jaffe , et al., "Fluocinolone Acetonide Sustained Drug Delivery Device to Treat Severe Uveitis," Ophthalmol. 107:2024-33 (2000b).
Jaffe , et al., "Safety and Pharmacokinetics of an Intraocular Fluocinolone Acetonide Sustained Delivery Device," Invest. Ophthalmol. & Vis. Sci. 41:3569-75 (2000).
Jain, "Nanobiotechnology-based strategies for crossing the blood-brain barrier", Nanomedicine (Lond), 7(8):1225-33 (2012).
Jallouli, et al., "Influence of surface charge and inner composition of porous nanoparticles to cross blood-brain barrier in vitro", Inl J Pharma, 344:103-9 (2007).
Je and Kim, "Chitosan derivatives killed bacteria by disrupting the outer and inner membrane", J Agric Food Chem., 54:6629-33 (2006b).
Je and Kim., "Antimicrobial action of novel chitin derivalive", Biochim Biophys Acta, 1760:104-9 (2006a).
Jedlitschky, et al.,"Peroxisomal leukotriene degradation: biochemical and clinical implications", Adv Enzyme Regul., 33:181-94 (1993).
Jevprasesphant, et al., "The influence of surface modification on the cytotoxicity of PAMAM dendrimers", Int J Pharm., 252:263-6 (2003).
Jiang, et at.,"Tumor Imaging by Means of Proteolytic Activation of Cell-Penetrating Peptides", PNAS, vol. 101(51):17867-72 (2004).
Jones, et al., "Cationic PAMAM dendrimers aggressively initiate blood clot formation", ACS Nano, 6:9900-10 (2012).
Jones, et al., "Cationic PAMAM dendrimers disrupt key platelet functions", Mol Pharma., 9:1599-611 (2012b).
Jou , et al., "Gangliosides Trigger Inflammatory Responses Via TLR4 in Brain Glia," Am. J. Pathol., 168:1619-30 (2006).
Jucker, et al., "Adsorption of bacterial surface polysaccharides on mineral oxides is mediated by hydrogen bonds", Colloids and Surfaces B, 9:331-43 (1997).
Jucker, et al., "Quantification of Polymer Interactions in Bacterial Adhesion", Environ Sci Technol., 32:2909-15 (1998).
Kam, et al., "Functionalization of carbon nanotubes via cleavable disulf de bonds efficient intracellular delivery of ciRNA and potent gene sllenoing", J. Am. Chem Soc., 127:12492-3 (2005).
Kambharmpati, et al., "Dendrimer nanoparticles for ocular drug delivery", J Ocular Pharmacol Ther., 29(2):151-65 (2013).
Kaminskas, et al., "The impact of molecular weight and PEG chain length on the systemic pharmacokinetics of PEGylated poly 1-lysine dendrimers", Mol Pharm., 5(3): 449-63 (2008).
Kang, et al,., "Tat-conjugated PAMAM dendrimers as delivery agents for antisense and siRNA oligonucleotides", Pram Res., 22:2099-106 (2005).
Kannan, et al., "Dendrimer-based postnatal therapy for neuroinflammation and cerebral palsy in a rabbit model", Sci Trans Med., 4(130) (2012).
Kannan, et al., "Dynamics of cellular entry and drug delivery by dendritic polymers into human epithelial carcinoma cells", J. Biomater. Sci. Polym. Edn., 15:311-30 (2004).
Kannan, et al., "Magnitude of [(11)C]PK11195 binding is related to severity of motor deficits in a rabbit model of cerebral palsy induced by intrauterine endotoxin exposure", Dev Neurosci., 33:231-40 (2011).
Kannan, et al., "Microglial activation in perinatal rabbit brain induced by intrauterine inflammation detection with 11C-(R)-PK11195 an6 small-animal PE1", J. Nucl Med., 48(6):946-54 (2007).

(56) References Cited

OTHER PUBLICATIONS

Kansara, et al., "Routes of ocular drug administration", Drug Delivery Research Advances, Mashkevih Ed Nova Sci Publishers, Inc. pp. 4-6 (2007).
Kapadia, et al., "Mechanisms of anti-inflammatory and neuroprotective actions of PPAR-gamma agonists", Front Biosci., 13:1813-26 (2009).
Katai, et al., "Caspaselike Proteases Activated in Apoptotic Photoreceptors of Royal College of Surgeons Rats," Invest. Ophthalmol. Vis. Sci., 40:1802-7 (1999).
Keelan, et al., "Cytokine abundance in placental tissues: evidence of inflammatory activation in gestational membranes with term and preterm parturition", Am J Obstetrics Gynecology, 181: 1530-6 (1999).
Kenny, et al., "Multifunctional receptor-targeted nanocomplexes for the delivery of therapeutic nucleic acids to the brain", Biomaterials, 34(36):9190-200 (2013).
Khan, et al., "Administration of N-acetyl cysleine after focal cerebral ischemia protects brain and reduces inflammation in a rat model of experimental sboke", J Neurosci Res.,4:519-27 (2004).
Khan, et al., "Bactericidal Action of Egg Yolk Phosvitin against *echerichia coli* under Thermal Stress", J Agric Food Chem., 48:1503-06 (2000).
Khan, et al., "In vivo biodistribution of dendrimers and dendrimer nanocomposites implications for cancer imaging and therapy", Tech Cancer Res Treat., 4(6):603-13 (2005).
Khan, et al., "Very long-chain fatty acid accumulation causes lipotoxic response via 5-lipoxygenase in cerebral adrenoleukodystrophy", J Lipid Res., 51(7):1685-95 (2010).
Khandare, et al., "Synthesis, cellular transport, and activity of polyamidoamine dendrimer-methylprednisolone conjugates", Bioconjugate Chem. 16:330-7 (2005b).
Kiefer, et al., "Effects of Dexamethasone on Microglial Activation In Vivo: Selective Downregulation of Major Histocompatibility Complex Class II Expression in Regenerating Facial Nucleus," J. Neuroimmunol. 34(2):99-108 (1991).
Kim and Wogan, "Mutagenesis oflhe supF gene of pSP189 replicating in AD293 cells cocultivated with activated macrophages: roles of nitric oxide and reactive oxygen species", Chem. Res. Toxicol., 19:1483-91 (2006).
Kim, et al., "Systematic investigation of polyamidoamine dendrimerc surface-modified with poly(ethylene glycol) for drug delivery applications: synthesis, characterization, and evaluation of cytotoxicity", Bioconjug Chem., 19:1660-72 (2008).
Kim, et al., "Use of single-site-functionalized PEG dendrons to prepare gene vectors that penetrate human mucus barriers", Angew Chem Int Ed Engl., 52(14):3985-8 (2013).
Kirpotin, et al., "Antibody targeting of long-circulating lipidic nanoparticles does not increase tumor localization but does increase internalization in animal models", Cancer Res., 66:6732-40 (2006).
Kitchens, et al., "Endocytosis and interaction of poly(amidoamine) Dendrimers with caco-2 cells", Pharm Res., 24:2138-45 (2007).
Kitchens, et al., "Transepithelial and endothelial transport of poly (amidoamine) dendrimers", Adv Drug Deliv Rev., 57(15):2163-76 (2005).
Kobayashi, et al., "Comparison of the Macromolecular MR Contrast Agents with Ethylenediamine-Core Versus Ammonia-Core Generation-6 Polyamidoamine Dendrimer", Bioconjugate Chem., 12:100-7 (2001c).
Kobayashi, et al.,"3D-Micro-MR Angiography of Mice Using Macromolecular MR Contrast Agents With Polyamidoamine Dendrimer Core With Reference to Their Pharmacokinetic Properties", Magnetic Resonance in Medicine, 45:454-60 (2001b).
Kobayashi, et al., "Dynamic micro-magnetic resonance imaging of liver micrometastasis in mice with a novel liver macromolecular magnetic resonance contrast agent DAB-Am64-(1B4M-Gd)(64)", Cancer Res., 61(13):4966-70 (2001).
Kobayashi, et al., "Multimoal nanoprobes for radionuclide and five color near infrared optical lymphatic imaging", ACS Nano, 1(4):258-64 (2007).
Kobayashi, et al., "Renal tubular damage detected by dynamic micro-MRI with a dendrimer-based magnetic resonance contrast agent", Kidney Int.,61(6):1980-5 (2002).
Kolhatkar, et al., "Surface acetylation of polyamidoamine (PAMAM) dendrimers decreases cytotoxicity while maintaining membrane permeability",Bioconjug Chem., 18(6):2054-60 (2007).
Kolhe, et al "Preparation cellular transport and activity of polyamidoamine-based dendritic nanodevices with a high drug payload", Biomaterials, 27:660-9 (2006).
Kolhe, et al., "Drug complexation, in vitro release and cellular entry of dendrimers and hyperbranched polymer", Intl. J Pharma, 259(1-2):143-60 (2003).
Kolhe, et al., "Hyperbranched polymer-drug conjugates with high drug payload for enhanced cellular delivery", Pharma Research, 21(12):2185-95 (2004).
Kommareddy and Arniji, "Preparation and evaluation of thiolmodified gelatin nanoparticles for intracellular DNA delivery in response to glutathione", Bioconjugate Chem., 16:1423-32 (2005).
Kono, et al., "Transfection activity of polyamidoamine dendrimers having hydrophobic amino acid residues in the periphery", Bioconjug Chem.,16(1):208-14 (2005).
Kou, et al., "Glutathione- and cysteine-induced transverse overgrowth on gold nanorods", J Am Chem. Soc., 129:6402-4 (2007).
Kroll, et al., "Outwitting the blood-brain barrier for therapeutic purposes: osmotic opening and other means",Neurosurgery, 42(5):1099-100 (1998).
Kukowska-Latallo, et al., "Efficient transfer of genetic material into mammalian cells using starburst polyamidoamine dendrimers", PNAS, 93:4897-902 (1996).
Kukowska-Latallo, et al., "Intravascular and endobronchial DNA delivery to murine lung tissue using a novel, nonviral vector", Hum Gene Ther, 11(10):1385-95 (2000).
Kukowska-Latallo, et al., "Nanoparticle targeting of anticancer drug improves therapeutic response in animal model of human epithelial cancer", Cancer Res.,65:5317-24 (2005).
Kurtoglu, et al., "Drug release characteristics of PAMAM dendrimer-drug conjugates with different linkers", Intl J Pharma, 384(1-2):189-94 (2010).
Kurtoglu, et al., "Poly(amidoamine) dendrimer-drug conjugates with disulfide linkages for intracellular drug delivery", Biomalerials, 30, 2112-21 (2009).
Landers, et al., Prevention of Influenza Pneumonitis by Sialic Acid-conjugated Dendritic Polymers, J. of Infectious Diseases, 186:1222-30 (2002).
Lebreton, et al., "Antibacterial single-bead scieening", Tetrahedron, 59:10213-22 (2003).
Lee, et al., "A single dose of doxorubicin functionalized bow-tie dendrimer cures mice bearing C-26 colon carcinomas", PNAS, 103:16649-56 (2006).
Lee, et al., "Designing dendrimers for biological applications", Biotech., 23:1517-26 (2005).
Lee, et al., "Synthesis of symmetrical and unsymmetrical PAMAM dendrimers by fusion between azide- and alkyne-functionalized PAMAM dendrons", Bioconjugate Chem., 18:579-84 (2007).
Lehmann, et al., "Inhibition of Tumor Necrosis Factor-Alpha Release in Rat Experimental Endotoxemia by Treatment With The 21-Aminosteroid U-74389G," Crit. Care Med. 27(6):1164-7 (1999).
Lentz, et al., "Viral vectors for gene delivery to the central nervous system", Neurobiol Dis, 48(2):179-188 (2012).
Lesniak, et al., "Biodistribution of fluorescently labeled PAMAM dendrimers in neonatal rabbits: effect of neuroinflammation", Mol Pharma,10:4560-71 (2013).
Lesniak et al., "Synthesis and characterization of PAMAM dendrimer based multifunctional nanodevices for targeting alphavbeta3 integrins", Bioconjug Chem., 18(4):1148-54 (2007).
Lessio, et al., "Cyclosporine A and NAC on the inducible nitric oxide synthase expression and nitric oxide synthesis to rat renal artery cultured cells", Kidney Int., 68:2508-16 (2005).
Letteron, et al., ., "Glucocorticoids Inhibit Mitochondrial Matrix Acyl-CoA ehydrogenases and Fatty Acid—Oxidation," Am. J. Physiol. 272:G1141-50 (1997).

(56) References Cited

OTHER PUBLICATIONS

Li, et al., "Peroxynitrite generated by inducible nitric oxide synthase and NADPH oxidase mediates microglial toxicity to oligodendrocytes", PNAS, 102:9936-41 (2005).
Li, et al., "Pharmacokinetics and biodistribution of nanoparticles", Mol Pharm., 5(4):496-504 (2008).
Li, et al., "Poly(vinyl alcohol) nanoparticles prepared by freezing-thawing process for protein/peptide drug delivery", J Controlled Release, 56:117-26 (1998).
Liang, et al., "Long-Term Protection of Retinal Structure But Not Function Using RAAV.CNTF in Animal Models of Retinitis Pigmentosa," Mol. Ther. 4(5):461-72 (2001).
Liang, et al., "PAMAM Dendrimers and Branched Polythyleneglycol (nanoparticles) Prodrugs of (−)-[beta]-D-(2R, 4R)- Dioxolane-Thymine (DOT) and Their Anti-HIV Activity", Antiviral Chemistry and Chemotherapy, 17(6) 321-9 (2006).
Lieb, et al., "Inhibition of LPS-Induced iNOS and NO Synthesis in Primary Rat Microglial Cells," Neurochem. Int. 42(2):131-7 (2003).
Lim and Simanek, "Synthesis of water-soluble dendrimers based on melamine bearing 16 paclitaxel groups", Organic Lett., 10:201-4 (2008).
Liu, et al., "Dendrimeric pyridoxamine enzyme mimics", J Am Chem Soc., 125(40):12110-11 (2003).
Loes, et al., "Adrenoleukodystrophy: a scoring method for brain MR observations", AJNR Am J Neuroradiol, 15:1761-6 (1994).
Lopez-Erauskin, et al., "Antioxidants halt axonal degeneration in a mouse model of X-adrenoleukodystrophy", Annals of neurology, 70(1):84-92 (2011).
Lopez, et al., "Antibacterial activity and cytotoxicity of PEGylated poly(amidoamine) dendrimers", Mol Biosyst., 5:1148-56 (2009).
Louwerse, et al., "Randomized, double-blind, controlled trial of acetylcysteine in amyotrophic lateral sclerosis", Arch. Neurol., 52:559-64 (1995).
Lu, et al., "YC-1 attenuates LPS-induced proinflammatory responses and activation of nuclear factor-kB in microglia", Br J Pharmacol., 151:396-405 (2007).
Mackay, et al., Distribution in brain of liposomes after convection enhanced delivery; modulation by particle charge, particle diameter, and presence of steric coating Brain Res, 1035(2):139-53 (2005).
Majoros, et al., "Acetylation of Poly(amidoamine) Dendrimers", Macromolecules, 36(15):5526-9 (2003).
Majoros, et al., "Poly(amidoamine) dendrimer-based multifunctional engineered nanodevice for cancer therapy", J Med Chem., 48(19):5892-9 (2005).
Makki, et al., "Intrauterine administration of endotoxin leads to motor deceits in a rabbit model: a link between prenatal infection and cerebral palsy", Am. J. Obstet. Gynecol., 199: 651-1651 (2008).
Malik, et al., "Dendrimer-platinate: a novel approach to cancer chemotherapy", Anti Cancer Drugs, 10:767-76 (1999).
Malik, et al., "Dendrimers relationship between structure and biocompatibility in vitro and preliminary studies on the biodistributiom of 125I-labeled polyamidoamine dendrimers in vivo", J Control Release, 65:133-48 (2000).
Mallard, et al., "Astrocytes and microglia in acute cerebral injury underlying cerebral palsy associated with preterm birth"Pediatr Res., 75:234-40 (2014).
Marano, et al., "Dendrimer Delivery of an Anti-VEGF Oligonucleotide Into The Eye: A Long-Term Study Into Inhibition of Laser-Induced Cnv, Distribution, Uptake and Toxicity," Nature Gene Therapy 12:1544-50 (2005).
Marchetti, et al., "Mitochondrial Permeability Transition Is a Central Coordinating Event of Apoptosis," J. Exp. Med., 184(3):1155-60 (1996).
Marquet, et al., "Noninvasive, transient and selective blood-brain barrier opening in non-human primates in vivo",Plos One, 6(7):):e22598. doi: 10.1371 (2011).

Matsumura and Maeda, "A new concept for macromolecular therapeutics in cancer chemotherapy: mechanism of tumoritropic accumulation of proteins and the antitumor agent", Cancer Res.,46:6387-92 (1986).
Mayhan and Heistad, "Permeability of blood-brain barrier to various sized molecules", Am J Physiol., 248:H712-8 (1985).
Mecke, et al., "Lipid bilayer disruption by polycationic polymers: the roles of size and chemical functional group", Langmuir, 21:10348-54 (2005).
Medline Plus, Blindness and vision loss, http://www.nlm.nih.gov/medlineplus/ency/article/003040.htm, accessed Jan. 23, 2013.
Meister and Anderson, "Glutathione", Annu Rev Biochem.,52:711-60 (1983).
Menjoge, et al., "Transfer of Pamam dendrimers across human placenta: Prospects of its use as drug carrier during pregnancy", J Controlled Release, 150(3):326-38 (2011).
Menjoge, et al., "Transport and bio distribution of dendrimers across human fetal membranes Implications for intravaginal administration of dendrimer-drug conjugates", Biomaterials, 31(18):50107-21 (2010b).
Menoge et al., "Dendrimer-based drug and imaging conjugates design considerations for nanomedical applications", Drug Deliv Today, 15(5-6):171-85 (2010).
Meyer-Luehmann, et al., "Rspid appearance and local toxicity of amyloid—beta plaques in a mouse model of Alzheimer's disease", Nature; 451:720-4 (2008).
Mignani, et al., "Expand classical drug administration ways by emerging routes using dentrimer drug delivery systems: a concise overview", Adv Drug Delivery Rev., 65(10):1316-30 (2013).
Milovic, et al., "Immobilized N alkylated polyethylenimine avidly kills bacteria by rupturing cell membranes with no resistance developed", Biotechnol Bioeng., 90:715-22 (2005).
Min, et al., "Gangliosides Activate Microglia Via Protein Kinase C and NADPH Oxidase," Glia, 48:197-206 (2004).
Min, et al., "Plasminogen-induced IL-1§ and TNFa production in microglia is regulated by reactive oxygen species", Biophys. Res. Commun., 312:969-74 (2003).
Mintzer and Simanek, "Nonviral vectors for gene delivery", Chem Rev, 109(2): 259-302 (2009).
Misha, et al., "Surface-engineered dendrimers: a solution for toxicity issues.", J Biomaterials Sci., 20:141-66 (2009).
Mishra, "PAMAM dendrimer-azithromycin conjugate nanodevices for the treatment of chlamydia trachomatis infections", Nanomed NanoTech, 7(6):935-44 (2011).
Mishra, et al., "Dendrimer brain uptake and targeted therapy for brain injury in a large animal model of hypothermic circulatory arrest", ACS Nano, 8:2134-47 (2014).
Mishra, et al., "Dendrimer-enabled moderation of gene expression in chlamydia trachomatis", Molecular Pharma., 9(3):413 (2012).
Morato, et al., "Activation of sirtuin 1 as therapy for the peroxisomal disease adrenoleukodystrophy", Cell Death Differ., 22:1742-53 (2015).
Morato, et al., "Pioglitazone halts axonal degeneration in a mouse model of X-linked adrenoleukodystrophy", Brain, 136(Pt 8):2432-43 (2013).
Mulders, et al., "Synthesis of a novel amino acid based dendrimer", Tetrahedron Lett., 38(4):631-4 (1997).
Mumper, et al., "Formulating a sulfonated antiviral dendrimer in a vaginal microbicidal gel having dual mechanisms of action", Drug Dev Ind Pharma., 35:515-24 (2009).
Myers, "The Effect of Hydroxyl Ion Concentration on the Thermal Death Rate of Bacterium Coli", J Bacterio, 15:341-56 (1928).
Mythri, et al., "Novel mucoadhesive polymers-A Review", J App Pharma Sci., 1(8):37-42 (2011).
Naberezhnykh, et al., "Interaction of chitosans and their N-acylated derivatives with lipopolysaccharide of gram-negative bacteria", Biochemistry (Mosc), 73:432-41 (2008).
Nagaraju, et al., "Delta 9-11 Compound, VBP15: Potential Therapy for DMD", Children's National Medical Center Washington DC (accessed Oct. 2015).
Najlah, et al., "In vitro evaluation of dendrimer prodrugs for oral drug delivery", Int J Pharm., 336:183-90 (2007).

(56) References Cited

OTHER PUBLICATIONS

Najlah, et al., "Synthesis, characterization and stability of dendrimer prodrugs", Int J Pharm.,308:175-82 (2006b).
Nance, et al., "A dense poly(ethylene glycol) coating improves penetration of large polymeric nanoparticles within brain tissue", Sci Transl Med,, 4:149ra119 (2012).
Nance, et al., "Brain-penetrating nanoparticles improve paclitaxel efficacy in malignant glioma following local administration", ACS Nano.,8(10):10655-64 (2014).
Napoli and Neumann, "Microglial clearance function in health and disease", Neuroscience, 158:1030-3B (2009).
Navath, et al., "Amino acid-functionalized dendrimers with heterobifunctional chemoselective peripheral groups for drug delivery applications", Biomacromolecules, 11(6):1544-63 (2010b).
Navath, et al., "Dendrimer-drug conjugates for tailored intracellular drug release based on glutathione levels", Bioconjugate Chem., 19(12):2446-53 (2008).
Navath, et al., "Injectable PAMAM dendrimer-PEG hydrogels for the treatment of genital infections: formation and in vitro and in vivo evaluation", Molecular Pharma, 8(4):1209-23 (2011).
Navath, et al., "Stimuli-responsive star polyethylene glycol) drug conjugates for improved intracellular delivery of the drug in neuroinflammation", J Controlled Release, 142(3):447-56 (2010).
Neal, et al., "Discovery and validation of a new class of small molecule toll-like receptor 4 (TLR4) inhibitors", Plos One, 8(6):e65779 (2013).
Neeves, et al., "Dilation and degradation of the brain extracellular matrix enhances penetration of infused polymer nanoparticles", Brain Res., 1160:121-32 (2007).
Nigavekar, et al., "3H dendrimer nanoparticle organ/tumor distribution", Pharm Res., 21(3):476-83 (2004).
Nimmerjahn, et al., "Resting microglial cells are highly dynamic surveillants of brain parenchyma in vivo", Science, 308:1314-18 (2005).
Noack, et al., "Nitrosative stress in primary gllal cultures after induction of the inducible isoform of nitric oxide synthase (i-NOS)", Toxicology, 148:133-42 (2000).
O'Mahony, et al., "Non-viral nanosystems for gene and small interfering RNA delivery to the central nervous system: formulating the solution", J Pharm Sci, 102(10):3469-84.
Oh, et al., "Synthesis, Characterization, and Surface Immobilization of Metal Nanoparticles Encapsulated within Bifunctionalized Dendrimers",Langmuir,19(24): 10420-5 (2003).
Okuda, et al., "Biodistribution characteristics of amino acid dendrimers and their PEGylated derivatives after intravenous administration", J Control Release, 114(1):69-77 (2006).
Olivas, "ReveraGen BioPharma Announces Start of Phase 1 Clinical Trial of VBP15 Dissociative Steroid Drug," http://www.prnewswire.corn/news-releases/reveragen-biopharma-announces-start-of-phase-1-clinical-trial-of-vbp15-dissociative-steroid-drug-300037964.html, media release, (Feb. 18, 2015).
Ortega, et al., "Amine and ammonium functionalization of chlaromethylsilane-ended dendrimers. Antimicrobial activity studies", Org Biomol Chem. 6:3264-9 (2008).
Oupicky, et al., "Laterally stabilized complexes of DNA with linear reducible polycations: strategy for triggered intracellular activation of DNA delivery vectors", J. Am Chem. Soc., 124:, 8-9 (2002).
Padilla, et al., "Polyster dendritic systems for drug delivery applicastions:Vitro and in Vivo evaluation", Bioonjugate, 13:453-61 (2002).
Paintlia, et al., "Lipopolysaccharidminduced peroxisomal dysfunction exacerbates cerebral white maner injury attenuation by N-acetyl cysteine", Exp. Neurol., 210:560-76 (2008).
Paleos, et al., "Acid- and salt-triggered multifunctional poly(propylene imine) dendrimer as a prospective drug delivery system", Biomacromolecules, 5(2):524-9 (2004).
Palmer, et al., "S-Nitrosothiols signal hypoxia-mimetic vascular pathology", J Clin Invest., 117:2592-601 (2007).
Panyam, et al., "Fluorescence and Electron Microscopy Probes for Cellular and Tissue Uptake of Poly(D,L-Lactide-Co-Glycolide) Nanoparticles," Met. J. Pharm. 262:1-11 (2003).
Panyam, et al., "Polymer Degradation and In Vitro Release of A Model Protein From Poly(D,L-Lactide-Co-Glycolide) Nano- and Micro particles," J. Control. Release 92:173-87 (2003b).
Pardridge, "Drug transport across the blood-brain barrier", J Cereb Blood Flow Metab, 32:1959-72 (2012).
Pardridge, "GSM: Blood-brain barrier delivery",. Drug Discov. Today, 12(1-2):54-61 (2007).
Patel. et al, "Polymeric nanoparticles for drug delivery to the central nervous system", Adv Drug Delivery Rev, 64(7):701-5 (2012).
Pathak, et al., "Recent trends in non-viral vector-mediated gene delivery", Biotechnol J, 4(11):1559-72 (2009).
Patil, et al., "Internally cationic polyamidoamine PAMAM-OH dendrimers for siRNA delivery: effect of the degree of quatermization and cancer targeting", Biomacromolecules, 10:258-66 (2009).
Patri, et al., "Targeted drug delivery with dendrimers: comparison of the release kinetics of covalently conjugated drug and non-covalent drug inclusion complex", Adv Drug Deliv Rev., 57:2203-14 (2005).
Patrick, et al., "Developmenl of a guinea pig model of chorioamnionitis and fetal brain injury", Am J Obstetrics and Gyn., 191:1205-11 (2004).
Pawlik and Bing, "Quantitative capillary topography and blood flow in the cerebral cortex of cats: an in vivo microscopic study", Brain Res.,, 208(1):35-58 (1981).
Pedrelli, et al., "Thyroid hormones and thyroid hormone receptors: effects of thyromimetics on reverse cholesterol transport", World J Gastroenterol., 16(47):5958-64 (2010).
Perez-Martinez, et al., "The use of nanoparticles for gene therapy in the nervous system", J Alzheimers Dis, 31(4):697-710 (2012).
Perry, et al., "Glutathione levels and variability in breast tumors and normal tissue", Cancer, 72: 783-7 (1993).
Perry, et al., "Microglia in neurodegenerative disease", Nat Rev Neurol., 6:193-201 (2010).
Perumal, et al., "Effects of branching architecture and linker on the activity of hyperbranched polymer-drug conjugates", Bioconjugates Chem., 20(5):842-96 (2009).
Perumal, et al., "The effect of surface functionality on cellular trafficking of dendrimers", Biomaterials, 29(24-25):3469-76 (2008).
Petty, et al., "Junctional complexes of the blood-brain barrier: permeability changes in neuroinflammation", Prog Neurobiol., 68:311-23 (2002).
Pikkemaat, et al.,"Dendritic PARAS EST Contrast Agents for Magnetic Resonance Imaging", Contrast Media Mol. Imaging, 2:229-39 (2007).
Powers and Moser, "Peroxisomal disorders: genotype, phenotype, major neuropathologic lesions, and pathogenesis", Brain Pathol., 8(1):101-20 (1998).
Powers, et al., "The dorsal root ganglia in adrenomyeloneuropathy: neuronal atrophy and abnormal mitochondria", J Neuropathol Exp Neurol., 60(5):493-501 (2001).
Pujol, et al., "Late onset neurological phenotype of the X-ALD gene inactivation in mice: a mouse model for adrenomyeloneuropathy", Hum Mol Gene.,, 11(5):499-505 (2002).
Pyo, et al., "Gangliosides Activate Cultured Rat Brain Microglia," J.Biol. Chem., 274:34584-9 (1999).
Qi, et al., "PEG-conjugated PAMAM Dendrimers Mediate Efficient Intramuscular Gene Expression", AAPS J, 11(3):395-405 (2009).
Qian, et al. "Synergistic inhibition of human glioma cell by temozolomide and PAMAM-mediated miR-21i", Appl Polymer, DOI: 10.1002/app.37823 (2013).
Rajaguru, et al., "Development of improved retinal prosthesis, using local release polymer coatings and sustained release dendrimer-drug nanodevices", Am Inst of Chem Engineers, Annual meeting Session # 447d-(22b), Nov. 2006.
Rajur, et al., "Covalent protein-oligonucleotide conjugates efficient delivery of antisense molecules", Bioconjugate Chem. , 8:g3-g40 (1997).
Régina, et al., "Antitumour activity of ANG1005, a conjugate between paclitaxel and the new brain delivery vector Angiopep-2", Br. J. Pharmacol., 155(2):185-97 (2008).

(56) References Cited

OTHER PUBLICATIONS

Reiter, et al., "Cytotoxic and antitumor activity of a recombinant immunotoxin composed of disulfide-stabilized anti-TAC Fv fragment and truncated pseudomonas exoloxin", Int. J. Cancer, 58:142-149 (1994).
Rinderknecht, et al., "Transfer of dendrimers in the perfused human placental lobule in citro prospects for use as drug carriers during pregnancy", Birth Defects Res part A, 88(5):351 (2010).
Romero, et al. "Micronutrients and intrauterine infection, preterm birth and the fetal inflammatory response syndrome", J Nutrition, 16685-16735 (2003).
Romero, et al., "A fetal systemic inflammatory response is followed by the spontaneous onset of preterm parturition", Am. J Obstet Gynecol., 179:186-93 (1998).
Romero, et al., "Inflammation in pregnancy: its roles in reproductive physiology, obstetnical complications, and fetal injury", Nutr Rev., 65:5194-202 (2007a).
Romero, et al., "The preterm panurition syndrome", Int J Obstet Gynaecol., 113:17-42 (2006).
Romero, et al., "The role of inflammation and infection in preterm birth", Semin. Reprod. Med., 25:21-39 (2007b).
Roy, et al., "Oral gene delivery with chitosan-DNA nanoparticles gnerates immunologic protection in a murine model of peanut allergy", Nature Med., 5:387-91 (1999)., Free Radic Biol Med. ,45:686-99 (1999).
Roy, et al., "Reactive oxygen species up- regulate CD11 b in microglia via nitric oxide: implications for neurodegenerative diseases", Free Radic. Biol. Med., 26:116-21 (2008).
Rui, et al., "Displasmenylcholine-folate liposomes: an efficient vehicle for intracellular drug delivery", J Am Chem Soc., 120(44):11213-18 (1998).
Saad, et al., "Receptor targeted polymers, dendrimers, liposomes: which nanocarrier is the most efficient for tumor-specific treatment and imaging", J Control Release,130(2):107-14 (2008).
Saadani-Makki, et al, "Intrauterine administration of endotoxin leads to motor deficits in a rabbit model: a link between prenatal infection and cerebral palsy", Am J Obstet Gynecol., 199(6):651-9 (2009b).
Saadani-Makki, et al., "Intrauterine endotoxin administration leads to white matter diffusivity changes in newborn rabbits", J. Child Neurol., 24:1179-89 (2009).
Sadekar, et al., "Comparative pharmacokinetics of PAMAM-OH dendrimers and HPMA copolymers in ovarian tumor-bearing mice", Drug Deliv Transl Res., 3(3):260-71 (2013).
Sadekar, et al., "Transepithelial transport and toxicity of PAMAM dendrimers for oral drug delivery", Adv Drug Del Rev., 64:571-88 (2012).
Sahoo, et al., "Residual Polyvinyl Alcohol Associated With Poly (D,L-Lactide-Co-Glycolide) Nanoparticles Affects Their Physical Properties and Cellular Uptake," J. Control. Release, 82:105-14 (2002).
Saito, et al., "Drug delivery strategy utilizing conjugation via reversible disulfide linkages: role and site of cellular reducing activities", Adv Drug Deliv Rev., 55:199-215 (2003).
Sakurai, et al., "Effect of Particle Size of Polymeric Nanospheres on Intravitreal Kinetics," Ophthalmic Res. 33:31-6 (2001).
Sanvicens, et al., "Oxidative Stress-Induced Apoptosis in Retinal Photoreceptor Cells is Mediated by Calpains and Caspases and Blocked by the Oxygen Radical Scavenger CR-6," J. Biol. Chem. 279(38):39268-78 (2004).
Sarin, et al., "Effective transvascular delivery of nanoparticles across the blood-brain tumor barrier into malignant glicoma cells", J Trans Med., 6(80):1-15 (2008).
Sato, et al., "Pharmacokinetics and enhancement patterns of macromolecular MR contrast agents with various sizes of polyamidoamine dendrimer cores", Magn Reson Med., 46:1169-73 (2001).

Sato, et at.,"Tumor Targeting and Imaging of Intraperitoneal Tumors by Use of Antisense Oligo-DNA Complexed with Dendrimers and/or Avidin in Mice1", Clinical Cancer Research, 7:3606-12 (2001 b).
Schlageter, et al. "Microvessel organization and structure in experimental brain tumors: microvessel populations with distinctive structural and functional properties",, Microvasc. Res., 58:312-28 (1999).
Schonenberger and Kovacs, "Hypoxia signaling pathways: modulators of oxygen-related organelles", Front Cell Dev Biol., 3:42-19 (2015).
Semmler, et al., "Therapy of X-linked adrenoleukodystrophy", Expert Rev. Neurother, 8:1367-79 (2008).
Shcharbin, et al. "How to study dendrimers and dendriplexes III. Biodistribution, pharmacokinetics and toxicity in vivo",, J Controlled Release, 181:40-2 (2014).
Shi, et al., "Dendrimer-entrapped gold nanoparticles as a platform for cancer-cell targeting and imaging", Small, 3:1245-52 (2007).
Shimazawa, et al., "Neuroprotective effects of minocycline against in vitro and in vivo retinal ganglion cell damage", Brain Res., 1053:185-94 (2005).
Shirai, et al., "Lack of carcinogenicity of butylated hydroxytoluene on long term administration of B6C3F Mice", Fd Chem Toxic, 20:861-5 (1982).
Sieving, et al., "Ciliarophic factor (CNTF) for human retinal degeneration phase 1 trial of CNTF delivered by encapsulated cell intraocular implants", PNAS, 103(10):3896-901 (2006).
Singh, "Peroxisomal fatty acid oxidation and cellular redox", Methods Enzymol, 352:36-372 (2002).
Sivanandan, et al., "Functional group diversity in dendrimers", Org Lett.,4 (21):3751-3 (2002).
Sk, et al., "Comparative study of microtubule inhibitors—Estramustine and natural podophyllotoxin conjugated PAMAM dendrimer on glioma cell proliferation", Eu J Med Chem., 68:47-57 (2013b).
Sk, et al., "Enhancing the efficacy of Ara-C through conjugation with PAMAM dendrimer and linear PEG: a comparative study", Biomacromolecules, 14(3):801-10 (2013).
Smith, et al., "Pioglitazone: mechanism of action", J Clin Pract Suppl, (121):13-8 (2001).
Southam, et al., "Drug Redeployment to Kill Leukemia and Lymphoma Cells by Disrupting SCD1-Mediated Synthesis of Monounsaturated Fatty Acids", Cancer Res., 75(12):2530-40 (2015).
Spierings, et al., "Connected to death: the (unexpurgated) mitochondrial pathway of apoptosis", Science, 310(5745):66-7 (2005).
Steffensen and Simanek, "Synthesis and manipulation of orthogonally protected dendrimers: building blocks for library synthesis", Angew. Chem., 116:5290-2 (2004).
Steinberg, et al., "Peroxisome biogenesis disorders", Biochim Biophys Acta., 1763(12):1733-48 (2006).
Stence, et al., "Dynamics of microglial activation: a confocal time-lapse analysis in hippocampal slices", Glia., 33(3):256-66 (2001).
Stolp, et al., "Effects of neonatal systemic inflammation on blood-brain barrier permeability and behaviour in juvenile and adult rats", Cardiovasc Psychiatry Neurol., 2011:469046 (2011).
Sun and Zhang, "Cationic polymer optimization for efficient gene delivery", Mini Rev Med Chem, 10(2):108-25 (2010).
Svenson, et al., "Dendrimers in biomedical applicatioms refections on the field", Adv Drug Delivery, 57(15):2106-29 (2005).
Sykova, and Nicholson, "Diffusion in brain extracellular space", Physiol Rev, 88(4):1277-340 (2008).
Tang, et al., "Insertion mode of a novel anionic antimicrobial peptide MDpep5 {Val-Glu-Ser-Trp-Val) from Chinese traditional edible larvae of housefly and its effect on surface potential of bacterial membrane", J Pharm Biomed Anal., 48:1187-94 (2008).
Tanito, et al., "Cytoprotective effects of geranylgeranylacetone against retinal photoxidative damage", J Neurosci., 25(9):2396-404 (2005).
Tao, et al., "Application of encapsulated cell technology for retinal degeneration diseases", Expert Opin Biol Ther., 6(7):717-26 (2006).
Tao, et al., "Encapsulated cell-based delivery of CNFT reduces photoreceptor degeneration in animal models of retinitis pigmentosa", Invest Opthalmol Vis Sci., 43(10):3292-8 (2002).

(56) References Cited

OTHER PUBLICATIONS

Teo, et al., "Preventing acute gut wall damage in infectious diarrhoeas with glycosylated dendrimers", EMBO Mol Med., 4:866-81 (2012).
Tepel, et al., "Prevention of radiographic-contrast-agent-induced reductions in renal function by acetylcysteine", NEJM, 343:180-4 (2000).
Thanos, et al., "Sick photoreceptors attract activated microglia from the ganglion cell layer: A model to study the inflammatory cascades in rats with inherited retinal dystrophy", Brain Res., 588(1):21-8 (1992).
Thanos, et al., "The migratory potential of vitally labelled microglial cells within the retina of rats with hereditary photoreceptor dystrophy", Int J Dev Neurosci., 11(5):671-80 (1983).
Thomas, "Paracetamol (acetaminophen) poisoning", Pharma Ther., 60:91-120 (1993).
Thomas, et al., "Progress and problems with the use of viral vectors for gene therapy", Nat Rev Genet, 4(5):346-58 (2003).
Thomas, et al., "Targeting and inhibition of cell growth by an engineered dendritic nanodevice", J Med Chem., 48:3729-35 (2005).
Thorne and Nicholson, "In vivo diffusion analysis with quantum dots and dextrans predicts the width of brain extracellular space", PNAS, 103(14):5567-72 (2006).
Till, et al., "Pexophagy: the selective degradation of peroxisomes", Int. J. Cell Biol. 2012:512721(2012).
Tolar, et al,, "N-acetyl-L-cysteine improves outcome of advanced cerebral adrenoleukodystrophy", Bone Marrow Transplant, 39(4), 211-215 (2007).
Tolic, et al., "Electrospray ionization Fourier transform ion cyclotron resonance mass spectrometric characterization of high molecular mass Starburst™ dendrimers", Intl J of Mass Spectrometry and Ion Processes, 165-166:405-18 (1997).
Tomalia, et al.,"Dendrimers as Multi-Purpose Nanodevices for Oncology Drug Delivery and Diagnostic Imaging", Biochemical Society Transactions, 35(1):61-7 (2007).
Tso, et al., "Apoptosis Leads to Photoreceptor Degeneration in Inherited Retinal Dystrophy of RCS Rats," Invest. Ophthalmol. Vis. Sci., 35(6):2693-9 (1994).
Tulu, et all. "Synthesis, characterization and antimicrobial activity of water soluble den6ritic macromolecules", Eur J Med Chem Ed., 4:1093-9 (2009).
Tziveleka, et al., "Synthesis and characterization of guanidinylated poll (propylene imine) dendrimers as gene transfection agents", J Control Release 117:137-1'16 (2007).
Ugwumadu, "Role of antibiotic therapy for bacterial vaginosis and intermediate flora in pregnancy". Best Pactice Research, 21:391-402 (2007).
Ulbrich, et al., "HPMA copolymers with pH-controlled release of doxorubicin in vitro cytotoxicity and in vivo antitumor activity", J Controlled Release, 87:33-47 (2003).
Unal, et al., "Gelation and swellinf behavior of end-linked hydrogels prepared from linear poly(ethylene glycol) and poly(amidoamine) dendrimers", Polymer, 47(24):8173-82 (2006).
University of Birmingham. "Contraceptive, cholesterol-lowering drugs used to treat cancer." ScienceDaily, https://www.sciencedaily.com/releases/2015/05/150514102813.htm, (May 2015).
Urakuboa, et al.,"Prenatal exposure to maternal infection alters cytokine expression in the placenta, amniotic fluid, and fetal brain", Schizophrenia Research. 47: 27-36 (2001).
Vale, et al., "Paracetamol (acetaminophen) poisoning", Lancet, 346:547-52 (1995).
Van Schayck, et al., "Are anti-oxidant and anti-ingammatory treatments effective in different subgroups of COPD a hypothesis", Respir Med., 92:1259-64 (1998).
Vargas, et al., "Neuroglial activation and neuroinflammation in the brain of patients with autism", Ann Neurol.,57(1):67-81 (2005).
Verma, et al., "Tunable reactivation of nanoparticle-inhibited-galactosidase by glutathione at intracellular concentrations", J Am Chem Soc., 126:13987-91 (2004).

Viers, et al., "Hydrogels formed by Endlinking Peg to dendrimer crosslink agents", Polymer Reprints, 41(1):729 (2000).
Villalonga-Barber, et al., "Dendrimers as biopharmaceuticals: Synthesis and properties", Curr Topic Med Chem., 8:1294-309 (2008).
Vincent, et al.,"Efficacy of Dendrimer-Mediated Angiostatin and Timp-2 Gene Delivery on Inhibition of Tumor Growth and Angiogenesis: In Vitro and In Vivo Studies", Int. J. Cancer, 105:419-29 (2003).
Voges, et al., "Imaging-guided convection-enhanced delivery and gene therapy of glioblastoma", Ann Neurol, 54(4):479-87 (2003).
Wagner, et al., "DNA-binding transferrin conjugates as functional gene-delivery agents: synthesis by linkage of polylysine or cthldium homodimer to the Iransferrin carbohydrate moiety", Bioconjugate Chem., 2:226-31 (1991).
Waite, et al., "Acetylation of PAMAM dendrimers for cellular delivery of siRNA", BMC Biotechnol., 9:38 (2009).
Wanders, "Peroxisomes, lipid metabolism, and human disease." Cell Biochem Biophys.,32: Spring:89-106 (2000).
Wanders, et al., "Peroxisomes, lipid metabolism and lipotoxicity", Biochim Biophys Acta., 1801(3):272-80 (2010).
Wang, et al., "The 21-Aminosteroid Tirilazad Mesylate Protects Against Liver Injury Via Membrane Stabilization Not Inhibition of Lipid Peroxidation," J. Pharm. Exp. Ther. 277(2):714-20 (1996).
Wang, et al., "Anti-inflammatory and anti-oxidant activity of anionic dendrimer-N-acetyl cysteine conjugates in activated microglial cells", Intl J Pharma, 377(1-2):159-68 (2009).
Wang, et al., "Inhibition of bacterial growth and intramniotic infection in a guinea pig model of chorioamnionitis using PAMAN dendrimers", Intl J Pharma, 395(1-2):298-308 (2010).
Wang, et al., "N-acetylcysteine reduces lipopolysaccharide-sensitized hypoxic—ischemic brain injury", Ann. Neurol., 61:263-71 (2006).
Wang, et al., "Synthesis characterization and in vitro activity of dendrimer-streptokinase conjugates", Bioconjugate Chem., 18(3):791-9 (2007).
Wang, et al., "The role of autophagy in the neurotoxicity of cationic PAMAM dendrimers", Biomaterials, 35:7588-97 (2014).
Waseem, et al., "Exogenous ghrelin modulates release of pro-inflammatory and anti-inflammatory cytokines in LPS stimulated macrophages through distinct signaling pathways", Surgery, 143(3):334-42 (2008).
Wells, et al., "Neuroprotection by minocycline facilitates significant recovery from spinal cord injury in mice", Brain, 126:162-37 (2003).
Wenzel, et al., "Prevention of Photoreceptor Apoptosis by Activation of the Glucocorticoid Receptor," Invest. Ophthalmol. Vis. Sci., 42(7):1653-9 (2001).
Wheeler, et al., "A defect of sphingolipid metabolism modifies the properties of normal appearing white matter in multiple sclerosis", Brain, 131:3092-3102 (2008).
Wiegand et al., "Agar and broth dilution methods to determine the minimal inhibitory concentration (MIC) of antimicrobial substances", Nature protocols, 3:163-75 (2008).
Wiesinger, et al., "The genetic landscape of X-linked adrenoleukodystrophy: inheritance, mutations, modifier genes, and diagnosis", Appl Clin Genet., 8:109-21 (2015).
Win-Shwe, et al., "Effects of PAMAM dendrimers in the mouse brain after a single intranasal instillation", Toxicol. Lett, 228:207-18 (2014).
Winterbourn and Metodiewa, "Reactivity of biologically important thiol compounds with superoxide and hydrogen peroxide", Free Radic Biol Med.,27:322-8 (1999).
Wipi, et al., "Synthesis of anti-inflammatory α-and β-linked acetamidopyranosides as inhibitors of toll-like receptor 4 (TLR4)", Tetrahedron Ltr., 56(23):3097-3100 (2015).
Wiwattanapatapee, et al., "Anionic PAMAM dendrimers rapidly cross adult rat intestine in vitro! a potential oral delivery system", Pharr». Res.,2:991-98 (2000).
Wiwattanapatapee, et al., "Dendrimers conjugates for colonic delivery of 5-aminosalicylic acid", J Control Release, 88:1-9 (2003).
Wohlfart, et al., "Transport of drugs across the blood-brain barrier by nanoparticles", J Control Release, 161(2):264-73 (2012).

(56) References Cited

OTHER PUBLICATIONS

Wolf, et al., "DARS-associated leukoencephalopathy can mimic a steroid-responsive neuroinflammatory disorder", Neurology, 84(3):226-30 (2015).
Wolinsky and Grinstaff, "Therapeutic and diagnostic applications of dendrimers for cancer treatment", Adv. Drug Deliv Rev., 60 (9):1037-55 (2008).
Woller and Cloninger, "The lectin-binding properties of six generations of mannose-functionalized dendrimers", Org Lett., 4(1):7-10 (2002).
Writer, et al., "Lipid peptide nanocomplexes for gene delivery and magnetic resonance imaging in the brain", J Control Release, 162(2):340-8 (2012).
Wu, et al., "Multivalent, bifunctional dendrimers prepared by click chemistry", Chem Commun (Camb), (46):5775-7 (2005).
Wu, et al., "Preparation and characterization of novel physically cross-linked hydrogels composed of poly(vinyl alcohol) and amine-terminated polyamidoamine dendrimer", Macromolecular Bioscience, 4(2):71-5 (2004).
Xu, et al., "Effect of N-acelylcysteine on lipopolysaccharide-induced intra-uterine fetal death and intra-uterine growth retardation in mice", Toxicol. Sci., 8B:525-33 (2005).
Yan and Sun, "Distribution of intracerebral ventricularly administered neurotropfiins in rat brain end its correlation with trk receptor expression", Exp Neurol., 127:23-36 (1994).
Yang, et al., "Dendrimers for Pharmaceutical and Biomedical Applications," J.Biomater. Sci. Polymer Ed. 17:3-19 (2006).
Yang, et al., "Fas and Activation-Induced Fas Ligand Mediate Apoptosis of T Cell Hybridomas: Inhibition of Fas Ligand Expression by Retinoic Acid and Glucocorticoids," J. Exp. Med., 181:1673-82 (1995).
Yang, et al., "Stealth dendrtmers for drug delivery: correlation between PEGylation, cytocompatibility, and drug payload", J Mater Sci Mater Med., 19:1991-7 (2008).
Yeh, et al., "A study of glutathione status in the blood and tissues of patients with breast cancer", Cell. Biochem. Funct., 24:555-9 (2006).
Yip, et al., "Intravenous administration of oral N-acetyl cysteine", Crit Care Med.,26:40-3 (1998).
Yiyun, et al., "Polyamidoamine dendrimers used as solubility enhancers of ketoprofen", Eu J Med Chem., 40:1390-3 (2005).
You, et al., "Reducible poly(2 dimethylaminoethyl methacrylate) Synthesis, cylotoxicity, and gene delivery activity", J. Controlled Release, 122:217-25 (2007).
Zafarullah, et al., "Molecular mechanisms of N acetyl cysteine actions", Cell Mol Life Sci.,60:6-20 (2003).
Zamecnik, "The extracellular space and matrix of gliomas.", J., Acta Neuropathol, 110(5):435-442 (2005).
Zeiss, et al., "CNTF Induces Dose-Dependent Alterations in Retinal Morphology in Normal and RCD-1 Canine Retina," Exp. Eye Res., 82(3):395-404 (2006).
Zeng, et al., "Identification of Sequential Events and Factors Associated With Microglial Activation, Migration, and Cytotoxicity in Retinal Degeneration in rd Mice," Invest. Ophthalmol. Vis. Sci. 46(8):2992-9 (2005).
Zhang, et al., "Neuroprotection of Photoreceptors by Minocycline in Light-Induced Retinal Degeneration," Invest. Ophthalmol. Vis. Sci., 45:2753-9 (2004).
Zhang, et al., "Conjugation of Polyamidoamine Dendrimers on Biodegradable Mircoparticles for Nonviral Gene Delivery", Bioconjugate Chemistry, 18(6): 2068-76 (2007).
Zhang, et al., "Evaluation of multivalent dendrimers based on melamine: kinetics of thiol—disulfide exchange depends on the structure of the dendrimer", J Am Chem Soc., 25:5086-94 (2003).
Zhang, et al., "Uniform brain tumor distribution and tumor associated macrophage targeting of systemically administered dendrimers", Biomaterials, 52:507-16 (2015).
Zheng, et al., "Multimodal nanoprobes evaluating physiological pore size of brain vasculatures in ischemic stroke models", Adv Healthc Mater., 3(11):1909-18 (2014).
Zhuo, et al., "In vitro release of 5-fluorouracil with cyclic core dendritic polymer", J Control Release,57:249-57 (1999).
Zimmermann, et al., "Extracellular matrix of the central nervous system: from neglect to challenge", Histochem Cell Biol, 130(4):635-53 (2008).
Zugates, et al., "Synthesis of polys amino esters) with thiol-reactive side chains for DNA delivery", J Am. Chem Soc., 12B:12726-34 (2006).
Alexiou, et al., "Magnetic Drug Targeting—Biodistribution of the Magnetic Carrier and the Chemotherapeutic agent Mitoxantrone after Locoregional Cancer Treatment", J Drug Targeting, 11(3):139-49 (2003).
Alizadeh, et al., "Tumor-associated macrophages are predominant carriers of cyclodextrin-based nanoparticles into gliomas", Nanomedicine, 6:382-90 (2010).
Apparaju, et al., "Pharmokinetics of gemcitabine in tumor and non-tumor extracellular fluid of brain: an in vivo assessment in rats employing intracerebral microdialysis", Cancer Chemother Pharmacol., 61:223-9 (2008).
Badie, et al., "Flow cycometric characterization of tumor-associated macrophages in experimental gliomas", Neurosurgery, 46(4):957-62 (2000).
Badie, et al., "In Vitro Modulation of Microglia Motility by Glioma Cells Is Mediated by Heptocyte Growth Factor/Scatter Factor", Neurosurgery, 44:1077-83 (1999).
Badie, et al., "Role of Microglia in Glioma Biology", Microscopy Res Tech., 54:106-13 (2001).
Balakrishnan, et al., "Nanomedicine in cerebral palsy", Intl J Nanomedicine, 8:4183-95 (2013).
Berger, et al., "Current and future pharmacological treatment strategies in x-linked adrenoleukodystrophy", Brain Pathol., 20(4):845-56 (2010).
Bertossi, et al., "Ultrastructural and Morphometric Investigation of Human Brain Capillaries in Normal and Peritumoral Tissues", Ultrastructural Pathology, 21:41-9 (1997).
Blasberg, et al., "Transport of α-Aminoisobutyric Acid Across Brain Capillary and Cellular Membranes", J Cerebral Blood Flow Metab, 3:8-32 (1983).
Boche, et al., "Review: Activation patterns of microglia and their identification in the human brain", Neuropath Applied Neurobiol., 39:3-18 (2013).
Bregy, et al., "The role of Gliadel wafers in the treatment of high-grade gliomas", Exp Rev Anticancer Therapy, 13(12):1453-61 (2013).
Brigger, et al., "Negative preclinical results with stealth nanospheres-encapsulated Doxorubicin in an orthotopic murine brain tumor model", J Controlled Release, 100:29-40 (2004).
Cabral, et al., "Accumulation of sub-100 nm polymeric micelles in poorly permeable tumours depends on size", Nature Nanotechnology, 6:815-23 (2011).
Chauhan, et al., "Strategies for advancing cancer nanomedicine", Nature Materials, 12:958-62 (2013).
Chekhonin, et al., "Targeted delivery of liposomal nanocontainers to the peritumoral zone of glioma by means of monoclonal antibodies against GFAP and the extracellular loop of Cx43", Nanomedicine, 8:63-70 (2012).
Chertok, et al., "Glioma Selectivity of Magnetically Targeted Nanoparticles: A Role of Abnormal Tumor Hydrodynamics", J Controlled Release, 122(3):315-23 (2007).
Chertok, et al., "Substantiating in vivo magnetic brain tumor targeting of cationic iron oxide nanocarriers via adsorptive surface masking", Biomaterials, 30:6780-7 (2009).
Choi, et al., "Dynamic fluorescence imaging for multiparametric measurement of tumor vasculature", J Biomedical Optics, 16(4):046008 (2011).
Choi, et al., "Renal clearance of quantum dots", Nature Biotechnology, 25(10):1165-70 (2007).
Chouinard-Pelletier, et al., "Use of inert gas jets to measure the forces required for mechanical gene transfection", BioMedical Eng OnLine, 11(67):1-12 (2012).
Curthoys, et al., "Proximal Tubule Function and Response to Acidosis", Clin J Am Soc Nephrol, 9:1627-38 (2014).

(56) References Cited

OTHER PUBLICATIONS

Da Fonseca, et al., "Microglia and Macrophages in Malignant Gliomas: Recent Discoveries and Implications for Promising Therapies", Clin Dev Immunol., Article ID 264124:1-5 (2013).
Dai, et al., "Intrinsic targeting of inflammatory cells in the brain by polyamidoamine dendrimers upon subarachnoid administration", Nanomedicine 5(9):1317-29 (2010).
Dave, et al., "The pharmacokinetics of letrozole in brain and brain tumor in rats with orthotypically implanted C6 glioma, assessed using intracerebral microdialysis", Cancer Chemother Pharmacol, 72:349-57 (2013).
Dinda, et al., "A transmission and scanning electron microscopic study of tumoral and peritumoral microblood vessels in human gliomas", J Neuro-Oncology, 16:149-58 (1993).
Dreaden, et al., "Small Molecule-Gold Nanorod Conjugates Selectively Target and Induce Macrophage Cytotoxicity Towards Breast Cancer Cells", Small J, 8(18):2819-22 (2012).
El Andaloussi, et al., "Stimulation of TLR9 with CpG ODN Enhances Apoptosis of Glioma and Prolongs the Survival of Mice with Experimental Brain Tumors", Glia, 54:526-35 (2006).
Gabrusiewicz, et al., "Characteristics of the Alternative Phenotype of Micrglia/Macrophages and its Modulation in Experimental Gliomas", PLoS One, 6(8): e23902 1-12 pages (2011).
Galarneau, et al., "Increased Glioma Growth in Mice Depleted of Macrophages", Cancer Research, 67(18):8874-81 (2007).
Giese, et al., "Cost of Migration: Invasion of Malignant Gliomas and Implications for Treatment", J Clinical Oncology, 21(8):1624-36 (2003).
Haga, et al., "Involvement of the Multidrug Resistance Protein 3 in Drug Sensitivity and Its Expression in Human Glioma", Jp J Cancer Res., 92:211-19 (2001).
Heath, et al., "Nanotechnology and Cancer", Ann Rev Med., 59:251-65 (2008).
Hirano, et al., "Vascular Structures in Brain Tumors", Human Pathology, 6(5):611-21 (1975).
Hobbs, et al., "Regulation of transport pathways in tumor vessels: Role of tumor type and microenvironment", PNAS, 95:4607-12 (1998).
Huang, et al., "Size-Dependent Localization and Penetration of Ultrasmall Gold Nanoparticles in Cancer Cells, Multicellular Spheroids, and Tumors in Vivo", ACS Nano, 6(5):4483-93 (2012).
Huo, et al., "Superior Penetration and Retention Behavior of 50 nm Gold Nanoparticles in Tumors", Cancer Research, 73(1):319-30 (2012).
Hussain, et al., "A Novel Small Molecule Inhibitor of Signal Transducers and Activators of Transcription 3 Reverses Immune Tolerance in Malignant Glioma Patients", Cancer Research, 67(20):9630-6 (2007).
Hussain, et al., "The role of human glioma-infiltrating microglia/macrophages in mediating antitumor immune responses", Neuro-Oncology, 8:261-79 (2006).
Jackson, et al., "Quantum Dots are Phagocytized by Macrophages and Colocalize with Experimental Gliomas", Neurosurgery, 60:524-30 (2007).
Jain, et al. "Delivering nanomedicine to solid tumors", Ntl Rev Clinical Oncology, 7(11):653-64 (2010).
Komohara, et al., "Possible involvement of the the M2 anti-inflammatory macrophage phenotype in growth of human gliomas", J Pathology, 216:15-24 (2008).
Kostarelos, et al., "Binding and Interstitial Penetration of Liposomes within Avascular Tumor Spheroids", Intl J Cancer, 112:713-21 (2004).
Kostarelos, et al., "Engineering Lipid Vesicles of Enhanced Intratumoral Transport Capabilities: Correlating Liposome Characteristics with Penetration into Human Prostate Tumor Spheroids", J Liposome Res., 15:15-27 (2005).
Lee, et al., "Blood Volume in the Rat", J Nuclear Med., 25:72-6 (1985).

Leukodystropy, National Organization for Rare Disorders, pp. 1-20, https://rarediseases.org/rare-diseases/leukodystrophy/, retrieved from the internet Sep. 5, 2017.
Li, et al., "The molecular profile of microglia under the influence of glioma", Neuro-Oncology, 14(8):958-78 (2012).
Liebner, et al., "Claudin-1 and claudin-5 expression and tight junction morphology are altered in blood vessels of human glioblastoma multiforme", Acta Neuropathol., 100:323-31 (2000).
Lintas, et al., "Genome-wide expression studies in autism spectrum disorder, rett syndrome, and down syndrome", Neurobiol. Disease, 45:57-68 (2012).
Locke, et al., "PET imaging of tumor associated macrophages using mannose coated 64Cu liposomes", Biomaterials, 33:7785-93 (2012).
Markovic, et al., "Minocycline reduces glioma expansion and invasion by attenuating microglial MT1-MMP expression", Brain, Behavior, Immunity, 25:624-8 (2011).
Meyers, et al., "Nanoparticles for imaging and treating brain cancer", Nanomedicine (Lond), 8(1):123-43 (2013).
Mildner, et al., "Microglia in the adult brain arise from Ly-6ChiCCR2+ monocytes only under defined host conditions", Nature Neuroscience, 10(12):1544-53 (2007).
Nakashima, et al., "In-vivo Microdialysis Study of the Distribution of Cisplatin into Brain Tumor Tissue after Intracarotid Infusion in Rats With 9L Malignant Glioma", J Pharma Pharmacol., 49:777-80 (1997).
Nitta, et al., "Expression of granulocyte colony stimulating factor and granulocyte-macrophage colony stimulating factor genes in human astrocytoma cell lines and in glioma specimens", Brain Research, 571:19-25 (1992).
Noell, et al., "Selective enrichment of hypericin in malignant glioma: Pioneering in vivo results", Intl J Oncology, 38:1343-8 (2011).
Okada, et al., Tumor-associated macrophage/microglia infiltration in human gliomas is correlated with MCP-3, but not MCP-1, Intl J Oncology, 34:1621-7 (2009).
Orr, et al., "Adenosine A2A receptor mediates microglial process retraction", Nat Neurosci., 12(7):872-8 (2009).
Parney, et al., "Flow cytometry and in vitro analysis of human glioma-associated macrophages", J Neurosurg., 110(3):572-82 (2009).
Perrault, et al., "Mediating Tumor Targeting Efficiency of Nanoparticles Through Design", Nano Lttrs, 9(5):1909-15 (2009).
Recinos, et al., "Combination of Intracranial Temozolomide With Intracranial Carmustine Improves Survival When Compared With Either Treatment Alone in a Rodent Glioma Model", Neurosurgery, 66:530-7 (2010).
Rippe, et al., "Effects of glomerular filtration rate on Ficoll sieving coefficients (theta) in rats", Kidney Intl, 69:1326-32 (2006).
Rittierodt, et al., "Repetitive doxorubicin treatment of glioblastoma enhances the PGP expression—a special role for endothelial cells", Exp Toxic Pathol., 55:39-44 (2003).
Roggendorf, et al., "Distribution and characterization of microglia/macrophages in human brain tumors", Acta Neuropathol, 92:288-93 (1996).
Sadekar, et al., "Comparative Biodistribution of Pamam Dendrimers and HPMA Copolymers in Ovarian Tumor-Bearing Mice", Biomacromolecules, 12(1):88-96 (2011).
Sarin, et al., "Physiologic upper limit of pore size in the blood-tumor barrier of malignant solid tumors", J Translational Medicine, 7(51):1-12 (2009).
Schadlich, et al., "Tumor Accumulation of NIR Fluorescent PEG—PLA Nanoparticles: Impact of Particle Size and Human Xenograft Tumor Model", ACS Nano, 5(11):8710-20 (2011).
Schwartzbaum, et al., "Epidemiology and molecular pathology of glioma", Nature Clin Practice Neurology, 2(9):494-503 (2006).
Siegal, "Which drug or drug delivery system can change clinical practice for brain tumor therapy", Neuro-Oncology, 15(6):656-69 (2013).
Siegal, et al., "Doxorubicin encapsulated in sterically stabilized liposomes for the treatment of brain tumor model: biodistribution and therapeutic efficacy", J Neurosurgery, 83:1029-37 (1995).
Suzuki, et al., "Regulation of cell migration and cytokine production by HGF-like protein (HLP)/macrophage stimulating protein (MSP) in primary microglia", Biomed Res., 29(2):77-84 (2008).

(56) References Cited

OTHER PUBLICATIONS

Tang, et al., "Size-Dependent Tumor Penetration and in Vivo Efficacy of Monodisperse Drug-Silica Nanoconjugates", Mol Pharma., 10:883-92 (2013).

Tang, et al., "Synthesis and Biological Response of Size-Specific, Monodisperse Drug-Silica Nanoconjugates", ACS Nano, 6(5):3954-66 (2012).

Tyler, et al., "A thermal gel depot for local delivery of paclitaxel to treat experimental brain tumors in rats", J Neurosurgery, 113:210-17 (2010).

Tzeng, et al., "Therapeutic nanomedicine for brain cancer", Therapeutic Delivery, 4(6):1-29 (2013).

Van Handel, et al., "Selective uptake of multi-walled carbon nanotubes by tumor macrophages in a murine glioma model", J Neuroimmunology, 208:3-9 (2009).

Venishetty, et al., "Increased brain uptake of docetaxel and ketoconazole loaded folate-grafted solid lipid nanoparticles", Nanomedicine. 9:111-21 (2013).

Wohlfart, et al., "Kinetics of transport of doxorubicin bound to nanoparticles across the blood-brain barrier", J Controlled Release, 154:103-7 (2011).

Wong, et al., "Multistage nanoparticle delivery system for deep penetration into tumor tissue", PNAS, 108(6):2426-31 (2011).

Wu, et al., "Oligo(ethylene glycol)-Based Thermosensitive Dendrimers and Their Tumor Accumulation and Penetration", J Am Chem Soc., 136:3145-55 (2014).

Yabroff, et al., "Patterns of care and survival for patients with glioblastoma multiforme diagnosed during 2006", Neuro-Oncology, 14(3):351-9 (2012).

Yoshii, et al., "Intercapillary Distance in the Proliferating Area of Human Glioma", Cancer Research, 48:2938-41 (1988).

Yu, et al., "Synthesis of Paclitaxel-Conjugated β-Cyclodextrin Polyrotaxane and Its Antitumor Activity", Angewandte Chemie Intl Ed., 52:7272-7 (2013).

Zhai, et al., "Microglia/Macrophages Promote Glioma Progression", Glia, 59(3):472-85 (2011).

Zhou, et al., "Highly penetrative, drug-loaded nanocarriers improve treatment of glioblastoma", PNAS, 110(29):11751-6 (2013).

Zhu, et al., "Systemic Delivery of Neutralizing Antibody Targeting CCL2 for Glioma Therapy", J Neurooncol, 104(1):83-92 (2011).

Zhu, et al., Targeting of Tumor-Associated Macrophages Made Possible by PEG-Sheddable, Mannose-Modified Nanoparticles, Mol Pharma., 10:3525-30 (2013).

* cited by examiner

Synthesis of D-TA (drug delivery) and Cy5-D-TA (imaging) conjugates

|   |   | Zeta (mV) | Mol wt (kD) |
|---|---|---|---|
| G4-OH | 4.20±0.54 | +4.26±0.28 | 14,100 |
| D-TA | 5.20±0.67 | +4.81±0.21 | 19,700 |
| D-TA-NH$_2$ | 5.0+0.2 | +5.30±0.23 |   |

FIG. 5C

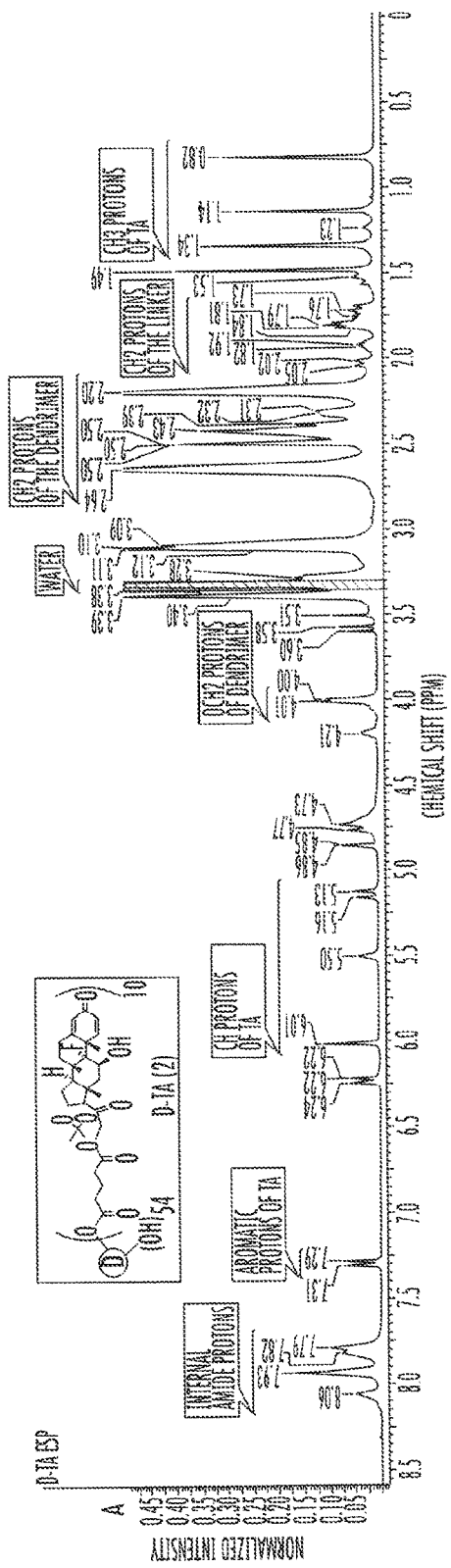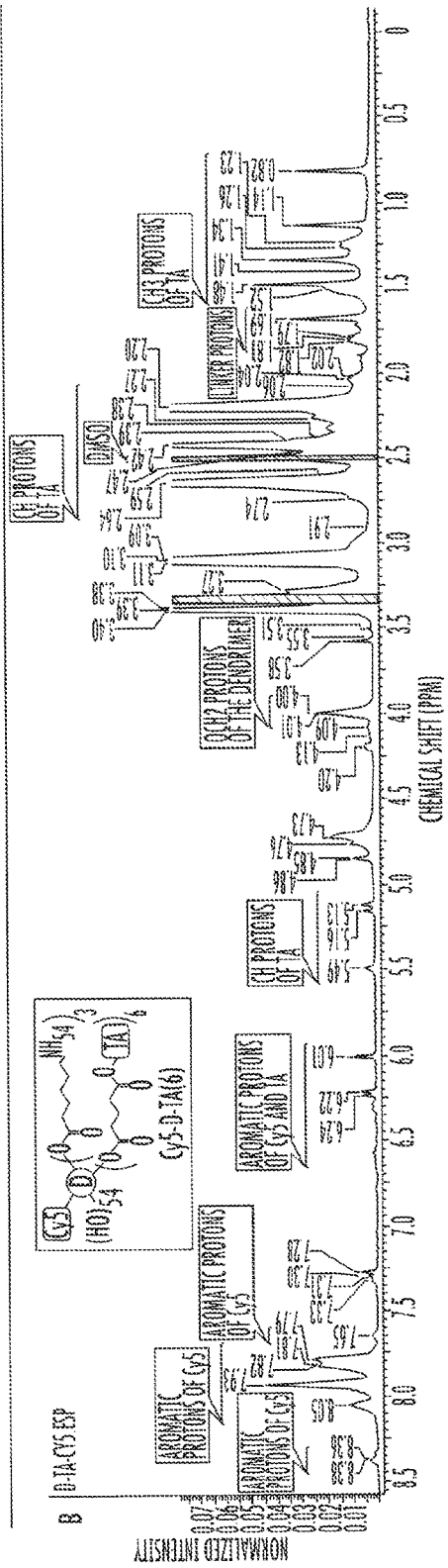
FIG. 6A
FIG. 6B

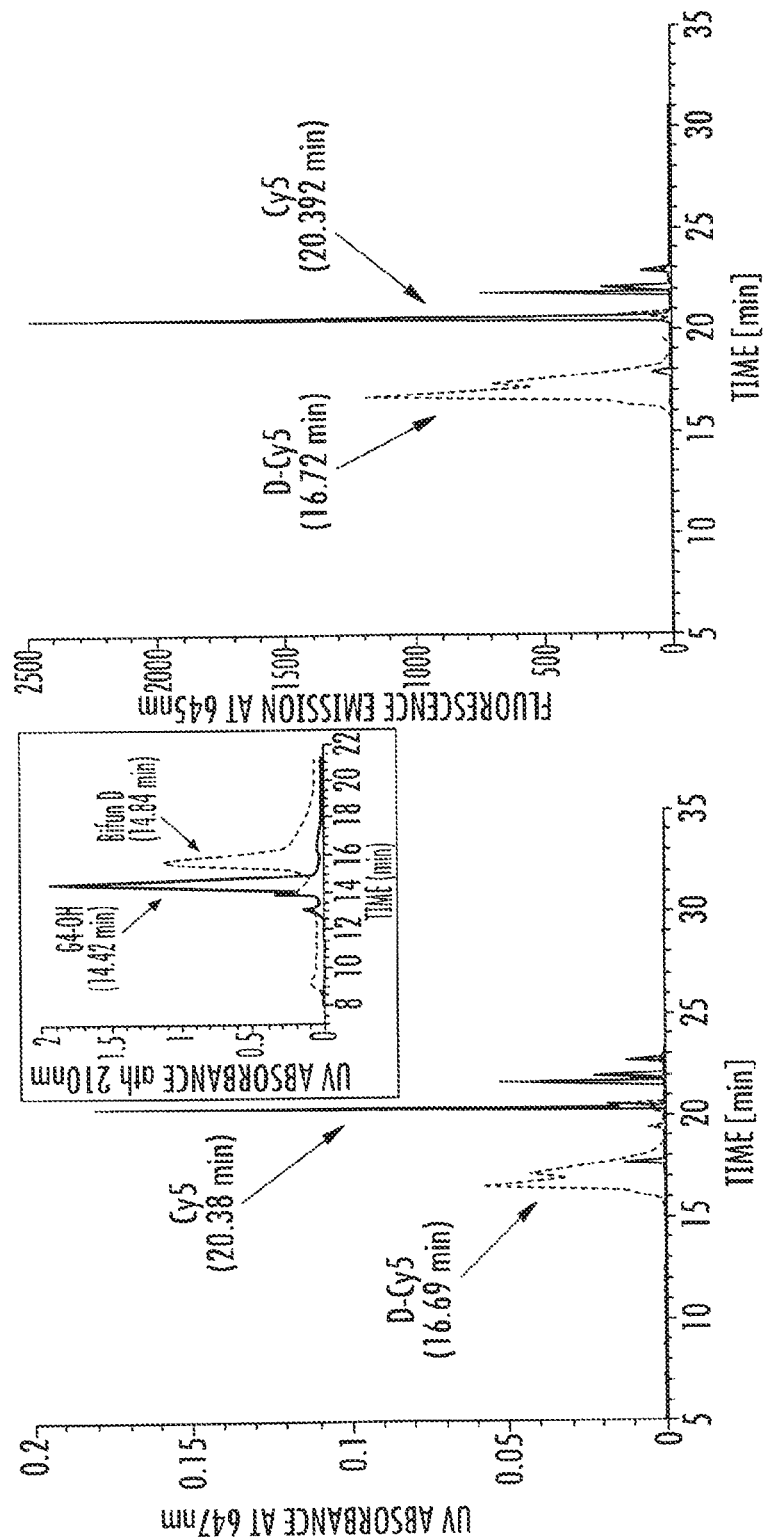

DENDRIMER COMPOSITIONS AND THEIR USE IN TREATMENT OF DISEASES OF THE EYE

REFERENCE TO RELATED APPLICATIONS

This application is a 371 application of International Application No. PCT/US2015/028386 filed Apr. 30, 2015, which claims the benefit of U.S. Provisional Patent Application No. 61/986,495, filed on Apr. 30, 2014, which is hereby incorporated by reference for all purposes as if fully set forth herein.

BACKGROUND OF THE INVENTION

Microglia are the resident macrophages of the brain and retina. They become activated in diseases such as diabetes and retinal degeneration where cells die, causing microglia to phagocytose cellular debris. Activation of retinal microglia occurs in a mouse model of ischemia/reperfusion injury (I/R), as occurs in inflammatory diseases of the eye, including glaucoma, age related macular degeneration (AMD), diabetic retinopathy and branch vein occlusion. Retinal vascular occlusion, be it by high intra-ocular pressure in the I/R model or thrombus in BVO, causes a decrease in blood flow within the eye resulting in retinal ischemia. This causes death of neurons initiating further activation of microglia.

Exudative (wet form) AMD is characterized by serous or hemorrhagic separation of the retinal pigment epithelium or neurosensory layer. Patients may develop choroidal neovascularization (CNV), which is manifested as fluid accumulation, hemorrhage, and/or lipid exudation.

The earliest stage of diabetic retinopathy (DR) is characterized by retinal vascular abnormalities including microaneurysms (saccular out-pouchings from the capillary wall), intraretinal hemorrhages, and cotton-wool spots (nerve fiber layer infarctions). As the disease progresses, the gradual closure of retinal vessels results in retinal ischemia, giving rise to signs including venous abnormalities (beading, loops), intraretinal microvascular abnormalities, and increasing retinal hemorrhage and exudation. Non-proliferative diabetic retinopathy is graded as mild, moderate, severe, and very severe according to the presence and extent of the above lesions.

The more advanced stage of DR involves the formation of new blood vessels, induced by the retinal ischemia, which spreads out either from the disc (neovascularization of the disc, NVD) or from elsewhere in the retina (neovascularization elsewhere, NVE). New vessels extending into the vitreous can cause vitreous hemorrhage, and tractional retinal detachments associated with accompanying contractile fibrous tissue (FIG. 1).

Dendrimers are a group of nanostructured polymers that have the potential to deliver drugs and small molecule therapies because of their large number of functional groups, to intracellular domains. Kannan et al has shown the therapeutic utility of a dendrimer-based therapies in treating a rabbit model cerebral palsy (CP). This rabbit model replicates the neuro-inflammation seen in the adult brain during CP.

To date, the only treatment conclusively demonstrated to be of long term benefit for DR is focal laser photocoagulation.

The standard treatment for patients with AMD is intravitreal injections of anti-VEGF into the eye, and there have been studies that have shown that anti-VEGF therapy may be useful in diabetic macular edema (DME). However, systemic delivery would have many advantages beyond current treatments as there are at present no systemic treatments available for ischemic retinopathies or AMD. These advantages include less frequent injections due to retention in microglia and ability to delivery systemically, avoiding frequent intraocular injections as in current anti-VEGF therapies, or of drugs or drug releasing implants from erobable or non-erodable sustained release devices.

Currently, there are no targeted therapies for AMD or DR. Targeting the activated microglia/macrophages from systemic administration can increase efficacy of the drugs and reduce side effects.

SUMMARY OF THE INVENTION

In accordance with an embodiment, the present inventors investigated the ability of systemically delivered dendrimers to target activated microglia in retina in ischemic retina. Microglial activation was induced an ischemia/reperfusion injury. The differential uptake of dendrimers between normal and ischemic retina was compared.

The inventors surprisingly found that the PAMAM dendrimers were able to target one key cell type in retinal neuroinflammation, activated microglia/macrophages (mi/ma). Retention by activated microglia/macrophages (mi/ma) occurred whether the dendrimer was delivered intravenously or intravitreally. Furthermore, the microglia and the retinal pigment epithelial cells retained dendrimer while other cell types in the eye and other organs did not take up the dendrimer. The dendrimers remained in mi/ma for an extended period of time, 21 days, the longest time point evaluated in this study.

In accordance with the embodiment, the present inventors, also administered dendrimers, systemically (intravenous), into animals where retinal (RNV) and choroidal neovascularization (CNV) was induced by a sub-retinal lipid injection. The differential uptake of dendrimers between normal and lipid-injected retina and choroids was compared.

The inventors found that the systemically administered dendrimers were selectively localized in the activated microglia/macrophages in the areas of RNV and the macrophages in the areas of CNV, but were not present in the fellow, uninjured eye.

In accordance with an embodiment, the present invention provides a method for treating an inflammatory and/or angiogenic disease in the eye of a subject comprising administering to the subject systemically, a composition comprising dendrimer nanoparticles, wherein the dendrimer nanoparticles comprise poly(amidoamine) (PAMAM) hydroxyl-terminated dendrimers covalently linked to at least one biologically active agent, in an amount effective to suppress or inhibit the inflammatory and/or angiogenic disease in the eye.

The present invention provides a method to treat retinal and choroidal neovascularization, upon systemic administration of a dendrimer carrying an active biological agent.

In accordance with another embodiment, the present invention provides a method for treating an inflammatory and/or angiogenic disease in the eye of a subject comprising periodically administering to the subject intravenously, a composition comprising dendrimer nanoparticles, wherein the dendrimer nanoparticles comprise poly(amidoamine) (PAMAM) hydroxyl-terminated dendrimers covalently linked to a biologically active agent, in an amount effective to suppress or inhibit the inflammatory and/or angiogenic disease in the eye.

BRIEF DESCRIPTION OF THE DRAWINGS

FIG. 2A There was a significant increase in the number of Iba-1$^+$ cells in I/R retinas (p<0.01). The software was trained only to select soma cells not processes that had both Iba-1 label only (yellow arrows) or Iba-1 as well as D-Cy5 (white arrows) in this 3-D surface volume. The total number of microglia/macrophages (green) and those with D-Cy5 are shown at all three time points after intravitreal (FIG. 2B) and intravenous (FIG. 2C) administration to I/R eyes. These values are significantly greater than in non-I/R retinas where no cells in retina had D-Cy5.

FIG. 3A) dendrimer levels upon single intravitreal injection of 20 µg of D-Cy5, shows significant difference between non I/R and I/R eyes. FIG. 3B D-Cy5 levels upon single intravenous injection of 600 µg; FIG. 3C Comparison of dendrimer levels in I/R eyes in both intravitreal and intravenous (at 30× higher dose) routes are comparable (n=8, student t-test). For quantification, posterior eye cups were homogenized lyophilized, and dendrimers were extracted into a small volume of methanol. Fluorescence was measured using previously established protocols, with appropriate D-Cy5 calibration and controls. D-Cy5 was near detection limit (NDL) in healthy eyes (3 and 21 days). (* indicates p<0.01 when I/R is compared to non-I/R)

FIGS. 5A-5C show chromatograms depicting the purity of the FIG. 5A) D-TA and FIG. 5B) Cy5-D-TA conjugates. FIG. 5C) shows the size, zeta potential, and molecular weights of the conjugates.

FIGS. 6A-6B depict the NMR characterization of the FIG. 6A) D-TA and FIG. 6B) Cy5-D-TA conjugates.

FIGS. 9A-9B show gel permeation chromatographs of the synthesized bifunctional dendrimer. FIG. 9A shows an elution time of 14.84 min from the column which differed from the elution time of G4-OH dendrimer (elution time 14.42 min). This indicates formation of a new compound and that there is only a minor shift in elution time indicating that the structural property of G4-OH dendrimer has not changed significantly. Appearance of a new peak simultaneously in 16.69 min at 647 nm (UV λmax for Cy5) and 645 nm (fluorescence emission of Cy5), which is different from the Cy5 peaks (20.39 min) FIG. 9B, confirms successful conjugation of dye to the dendrimers.

FIGS. 10A-10C are the HPLC chromatograms of the kidney extract at 24 hrs, 72 hrs and 21 days respectively post D-Cy5 injection intravenously proving the fluorescence signals from kidney cortex are from intact D-Cy5 (based on the retention time 14.92 min), whereas the time increases the peak signal decreases indicating D-Cy5 excretion via urine and is in good agreement with the confocal images.

FIG. 18B: monocyte chemoattractant-MCP-1). D-NAC also enhanced anti-inflammatory (IL-10) (FIG. 18C). *** denotes p<0.001.

FIG. 19 is a bar graph representing the measurement of CNV areas (mm$^2$) of HpODE, D-TA, or free TA (F-TA). About 95% of the reduction of CNV can be attributed to a dual anti-inflammatory and anti-angiogenic effect.

DETAILED DESCRIPTION OF THE INVENTION

Figure 1:
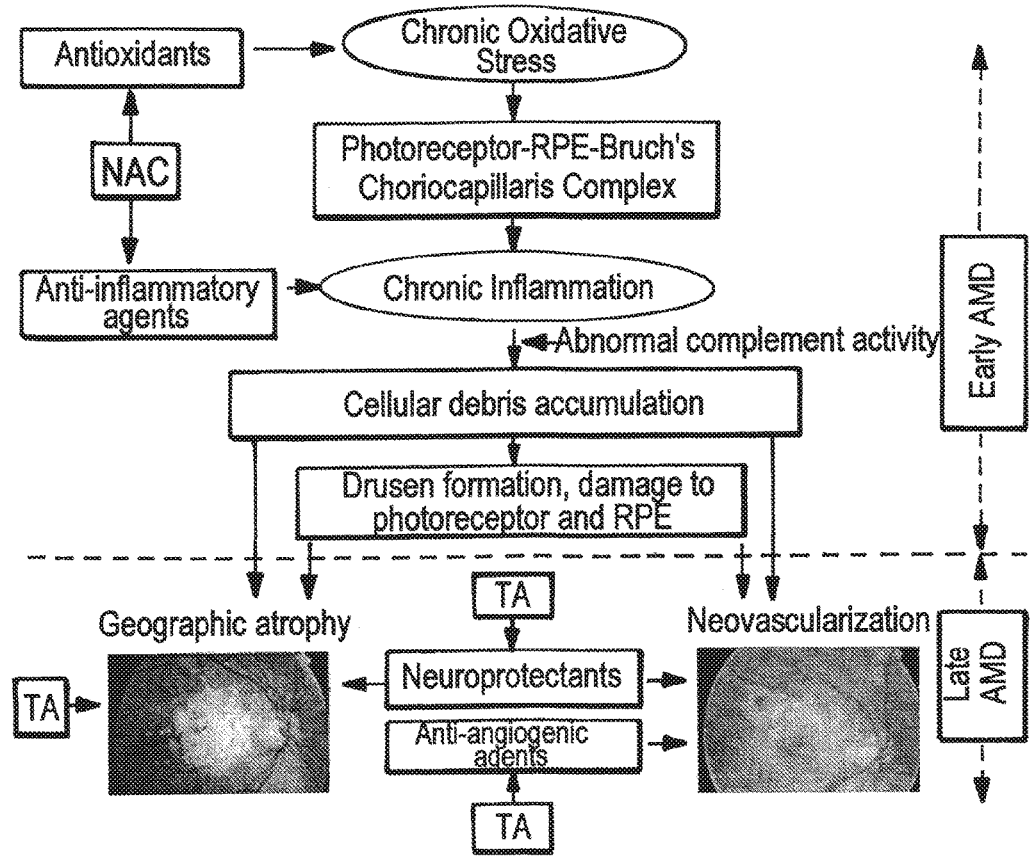
FIG. 1 is a schematic showing the pathogenesis of AMD and how N-acetyl-cysteine (NAC) is a multimodal drug that can attenuate multiple pathways.

In accordance with one or more embodiments, the present invention discloses the ability of PAMAM dendrimers to target one key cell type in retinal neuroinflammation, activated microglia via intravenous, systemic injection. Surprisingly, retention by activated microglia occurred whether the dendrimer was delivered intravenously when compared to intravitreal injection. Furthermore, the microglia retained dendrimer while other cell types did not take up the dendrimer. The dendrimers remained in microglia for an extended period of time, 21 days, the longest time point evaluated in this study. Activated microglia/macrophages have been associated with inflammatory and/or angiogenic retinal diseases such as macular degeneration, diabetic retinopathy, glaucoma, and retinopathy of prematurity. Ischemia-reperfusion (I/R) injury has been used to model certain aspects of chronic glaucoma, diabetic retinopathy and branch vein occlusion (BVO). I/R injury causes occlusion of both retinal and choroidal blood vessels, resulting in reduced blood flow and tissue hypoxia. The above conditions were reported to cause disruption of blood retinal barriers (BRB), activation of resident microglia/macrophages, infiltration of microglia and macrophages from choroid and systemic circulation, elevated production of cytokines (TNF-$\alpha$, Inf-$\alpha$, TGF-$\beta$. IL-1$\beta$ and IL-6) and death of retinal ganglion cells (RGCs).

An important aspect of the inventive methods was the fact that the D-Cy5 was retained almost exclusively in activated microglia, whether they were delivered intravenously or intravitreally. Intravenous administration is safer than intravitreal, but intravitreal is currently the standard of care for anti-VEGF therapies used in treating exudative age-related macular degeneration (wet AMD) and diabetic macular edema. D-Cy5 retention in microglia at 21 days post femoral injection is also very significant in that repeated injections like current anti-VEGF therapies would not require intravitreal injection.

This method was further supported by the surprising finding that in a rat choroid neovascularization (CNV) model, systemic intravenous injection of a dendrimer compound of the present invention conjugated to N-acetalcysteine significantly reduced the area of CNV in the treated animals compared to controls.

In accordance with some embodiments, the present invention provides a composition comprising dendrimer nanoparticles, wherein the dendrimer nanoparticles comprising predominantly hydroxyl-terminated poly(amidoamine) (PAMAM) dendrimers covalently linked to at least one or more biologically active agents, which can be the same or different, in an amount effective to suppress or inhibit an inflammatory disease in the eye. As used herein, the term "predominantly hydroxyl-terminated" means that a majority of the surface functional groups of the dendrimers are OH groups. In some embodiments, the dendrimers can have a mixture of different functional groups.

Thus, in accordance with another embodiment, the present invention provides a method for treating an inflammatory and/or angiogenic disease in the eye of a subject by administering a composition comprising dendrimer nanoparticles intravenously; wherein the dendrimer nanoparticles comprise one or more ethylene diamine-core poly(amidoamine) (PAMAM) hydroxyl-terminated dendrimers covalently linked to at least one or more biologically active agents, which can be the same or different, in an amount effective to suppress or inhibit the inflammatory and/or angiogenic disease in the eye.

As used herein, the term "PAMAM dendrimer" means poly(amidoamine) dendrimer, which may contain different cores, with amidoamine building blocks. The method for making them is known to those of skill in the art and generally, involves a two-step iterative reaction sequence that produces concentric shells (generations) of dendritic $\beta$-alanine units around a central initiator core. This PAMAM core-shell architecture grows linearly in diameter as a function of added shells (generations). Meanwhile, the surface groups amplify exponentially at each generation according to dendritic-branching mathematics. They are available in generations G0-10 with 5 different core types and 10 functional surface groups. The dendrimer-branched polymer may consist of polyamidoamine (PAMAM), polyester, polyether, polylysine, or polyethylene glycol (PEG), polypeptide dendrimers. It will be understood by those of skill in the art that the dendrimer compositions described and claimed herein can be dendrimers of G3 to G10 in range, typically, G4 or G5 in range, with mixtures of different G levels also possible.

In accordance with some embodiments, the PAMAM dendrimers used can be generation 4 dendrimers, with hydroxyl groups attached to their functional surface groups.

In some embodiments, the dendrimers are in nanoparticle form and are described in detail in international patent publication No. WO2009/046446, which is incorporated by reference herein.

As used herein, the term "inflammatory disease of the eye" means diseases of the eye associated with inflammation of the tissues of the eye, including, for example, age-related macular degeneration (ARMD), retinitis pigmentosa, optic neuritis, infection, sarcoid, sickle cell disease, retinal detachment, temporal arteritis, retinal ischemia, arteriosclerotic retinopathy, hypertensive retinopathy, retinal artery blockage, retinal vein blockage, hypotension, diabetic retinopathy, macular edema, and also includes angiogenic diseases including, for example, choroidal neovascularization.

In accordance with an embodiment, the present invention provides for the use of the compositions disclosed herein, for treating an inflammatory and/or angiogenic disease in the eye of a subject comprising administering to the subject systemically, in an effective amount, to suppress or inhibit the inflammatory disease in the eye of the subject.

In accordance with another embodiment, the present invention provides a method for attenuating or treating disorders of the eye in a subject caused by oxidative and ER stress in a cornea of the subject comprising administering to the subject an effective amount of a dendrimer composition comprising a biologically active agent.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

In some embodiments, the biologically active agents can include detectable moieties. As used herein, the term "detectable moiety" means that this specific portion of the molecule comprises at least one or more imaging agents which are attached to the dendrimer molecule. At least one of the imaging agents is a fluorescent dye. The dyes may be emitters in the visible or near-infrared (NIR) spectrum. Known dyes useful in the present invention include carbocyanine, indocarbocyanine, oxacarbocyanine, thüicarbocyanine and merocyanine, polymethine, coumarine, rhodamine, xanthene, fluorescein, boron-dipyrromethane (BODIPY), Cy3, Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS.

Organic dyes which are active in the NIR region are known in biomedical applications. However, there are only a few NIR dyes that are readily available due to the limitations of conventional dyes, such as poor hydrophilicity and photostability, low quantum yield, insufficient stability and low detection sensitivity in biological system, etc. Significant progress has been made on the recent development of NIR dyes (including cyanine dyes, squaraine, phthalocyanines, porphyrin derivatives and BODIPY (borondipyrromethane) analogues) with much improved chemical and photostability, high fluorescence intensity and long fluorescent life. Examples of NIR dyes include cyanine dyes (also called as polymethine cyanine dyes) are small organic molecules with two aromatic nitrogen-containing heterocycles linked by a polymethine bridge and include Cy5, Cy5.5, Cy7 and their derivatives. Squaraines (often called Squarylium dyes) consist of an oxocyclobutenolate core with aromatic or heterocyclic components at both ends of the molecules, an example is KSQ-4-H. Phthalocyanines, are two-dimensional 18π-electron aromatic porphyrin derivatives, consisting of four bridged pyrrole subunits linked together through nitrogen atoms. BODIPY (boron-dipyrromethane) dyes have a general structure of 4,4'-difluoro-4-bora-3a, 4a-diaza-s-indacene) and sharp fluorescence with high quantum yield and excellent thermal and photochemical stability.

In accordance an embodiment, the biologically active agent is selected from the group consisting of enzymes, receptor antagonists or agonists, hormones, growth factors, antibodies, oligonucleotides, siRNAs, microRNAs, vitamin A, vitamin C, vitamin E, beta-carotene, and small molecules.

In accordance with another embodiment, the small molecules are selected from the group consisting of anti-inflammatory agents such as steroids, including methyl prednisone, dexamethasone, non-steroidal anti-inflammatory agents, including COX-2 inhibitors, corticosteroid anti-inflammatory agents, gold compound anti-inflammatory agents, immunosuppressive anti-inflammatory and anti-angiogenic agents, salicylate anti-inflammatory agents, ranibizumab, minocycline, anti-VEGF agents, including aflibercept, and rapamycin. They can also include anti-oxidants such as N-acetyl cysteine, omega-3 fatty acid derivatives such as resolving and neuroprotectin-D1 (NPD1).

In accordance with some other embodiments, the molecules can include antibodies, including, for example, daclizumab, bevacizumab (Avastin®), ranibizumab (Lucentis®), basiliximab, ranibizumab, and pegaptanib sodium or peptides like SN50, and antagonists of NFκβ.

In accordance with some embodiments, the biologically active agent can be N-acetyl cysteine (NAC) and/or triamcinolone acetonide (TA).

In some embodiments, the dendrimer compositions used in the methods described herein are generation-4, hydroxyl terminated PAMAM dendrimers (G4-OH) conjugated with one or more biologically active agents. For example, G4-OH dendrimers conjugated to NAC and/or TA can be used in the inventive methods.

In some embodiments, there is contemplated, theranostic compositions which would include at least one biologically active agent and at least one detectable moiety. For example, a theranostic composition could include a G4-OH or amine-G4-NH$_2$ dendrimer conjugated to NAC and to D-Cy5 to aid in visualization of the therapeutic or biologically active agent in the body.

Triamcinolone acetonide (4aS,4bR,5S,6aS,6bS,9aR, 10aS,10bS)-4b-fluoro-6b-glycoloyl-5-hydroxy-4a,6a,8,8-tetramethyl-4a,4b,5,6,6a,6b,9a,10,10a,10b,11,12-dodecahydro-2H-naphtho[2',1':4,5]indeno[1,2-d][1,3]dioxol-2-one) is a synthetic corticosteroid used to treat various skin conditions, to relieve the discomfort of mouth sores, and in nasal spray form, to treat allergic rhinitis. It is a more potent derivative of triamcinolone, and is about eight times as potent as prednisone. As an intravitreal injection, triamcinolone acetonide has been used to treat various eye diseases and has been found useful in reducing macular edema. Drug trials have found it to be as efficient as anti-VEGF drugs in eyes with artificial lenses over a two-year period.

It will be understood that the dendrimer compositions used with the methods of the present invention can be in any suitable formulation. Examples of such formulations include one or more of a liposome, a microcapsule, and a nanocapsule.

Embodiments of the invention also include a process for preparing pharmaceutical products comprising the compounds. The term "pharmaceutical product" means a composition suitable for pharmaceutical use (pharmaceutical composition), as defined herein. Pharmaceutical compositions formulated for particular applications comprising the compounds of the present invention are also part of this invention, and are to be considered an embodiment thereof.

As used herein, the term "treat," as well as words stemming there from, includes preventative as well as disorder remitative treatment. The terms "reduce," "suppress," "prevent," and "inhibit," as well as words stemming there from, have their commonly understood meaning of lessening or decreasing. These words do not necessarily imply 100% or complete treatment, reduction, suppression, or inhibition.

With respect to pharmaceutical compositions described herein, the pharmaceutically acceptable carrier can be any of those conventionally used, and is limited only by physico-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compounds of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compound. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

In an embodiment, the term "administering" means that the compounds of the present invention are introduced into a subject, preferably a subject receiving treatment for a inflammatory related disease of the eye, and the compounds are allowed to come in contact with the one or more disease related cells or population of cells in vivo.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

It will be understood by those of ordinary skill that a dosing regimen used in the inventive methods can be any length of time sufficient to provide a reduction in the inflammatory disease and/or oxidative stress in the eyes of the subject. The term "chronic" as used herein, means that the length of time of the dosage regimen can be hours, days, weeks, months, or possibly years.

In a further embodiment, the compositions and methods of the present invention can be used in combination with one or more additional therapeutically active agents which are known to be capable of treating conditions or diseases discussed above. For example, the compositions of the present invention could be used in combination with one or more known therapeutically active agents, to treat inflammatory and/or angiogenic disease, or an oxidative stress related disease. Non-limiting examples of other therapeutically active agents that can be readily combined in a pharmaceutical composition with the compositions and methods of the present invention include drugs in the non-steroidal anti-inflammatory drug class (NSAID).

In accordance with an embodiment, the present invention provides a method for attenuating or treating disorder of the eye in a subject caused by inflammatory disease, oxidative stress, and/or angiogenesis in an eye of the subject comprising administering to the subject an effective amount of a composition comprising a dendrimer composition conjugated to a non-steroidal anti-inflammatory drug.

Examples of NSAIDS used in the methods of the present invention include mefenamic acid, aspirin, Diflunisal, Salsalate, Ibuprofen, Naproxen, Fenoprofen, Ketoprofen, Deacketoprofen, Flurbiprofen, Oxaprozin, Loxoprofen, Indomethacin, Sulindac, Etodolac, Ketorolac, Diclofenac, Nabumetone, Piroxicam, Meloxicam, Tenoxicam, Droxicam, Lornoxicam, Isoxicam, Meclofenamic acid, Flufenamic acid, Tolfenamic acid, elecoxib, Rofecoxib, Valdecoxib, Parecoxib, Lumiracoxib, Etoricoxib, Firocoxib, Sulphonanilides, Nimesulide, Niflumic acid, and Licofelone.

Typically, an attending physician will decide the dosage of the composition with which to treat each individual subject, taking into consideration a variety of factors, such as age, body weight, general health, diet, sex, compound to be administered, route of administration, and the severity of the condition being treated. By way of example, and not intending to limit the invention, the systemic dose of the compositions of the present invention can be about 0.0001 to about 1000 mg/kg body weight of the subject being treated, from about 0.01 to about 100 mg/kg body weight, from about 0.1 mg/kg to about 50 mg/kg, and from about 0.5 mg to about 25 mg/kg body weight In an embodiment of the present invention, patients are treated periodically with the dendrimer-drug compositions in accordance with a dosing regimen.

Thus, in accordance with another embodiment, the present invention provides a method for treating inflammatory and angiogenic diseases in the eye of a subject comprising periodically administering to the subject systemically, a composition comprising dendrimer nanoparticles, wherein the dendrimer nanoparticles poly(amidoamine) (PAMAM) hydroxyl-terminated dendrimers covalently linked to a biologically active agent, in an amount effective to suppress or inhibit the inflammatory disease in the eye.

It is contemplated that in an embodiment of the present invention, that the patients are treated with the anti-inflammatory dendrimer compositions, for example, a biweekly, monthly, bimonthly or trimonthly schedule.

EXAMPLES

High Performance Liquid Chromatography (HPLC) analysis. The purity of the dendrimer-Cy5 conjugates (D-Cy5) were analyzed using a Waters HPLC instrument (Waters Corporation, Milford, Mass.) equipped with Waters In-line degasser, binary pump, photodiode array (PDA) detector, multi fluorescence $\lambda$ detector and auto sampler (maintained at 4° C.) interfaced with Empower software. The HPLC chromatogram was monitored simultaneously for absorbance at 210 nm for dendrimer and 650 nm for Cy5 using Waters 2998 PDA detector and fluorescence with excitation at 645 nm and emission at 662 nm using Waters 2475 fluorescence detector. The water/acetonitrile (0.1% w/w TFA) was freshly prepared, filtered, degassed, and used as a mobile phase. TSK-Gel ODS-80 Ts (250×4.6 mm, 25 cm length with 5 µm particle size) connected to TSK-Gel guard column was used. A gradient flow was used with initial condition being 90:10 ($H_2O$/ACN) and then gradually increasing the acetonitrile concentration to 10:90 ($H_2O$/ACN) in 30 min and returning to original initial condition 90:10 ($H_2O$/ACN) in 60 min with flow rate of 1 ml/min.

Dynamic light scattering and Zeta potential analysis. The particle size and potential of G4-OH and D-Cy5 conjugates were determined by dynamic light scattering (DLS) using a Zetasizer Nano ZS (Malvern Instrument Ltd. Worchester, U.K.) equipped with a 50 mW He—Ne laser (633 nm). For sizing, the samples were dissolved in deionized water (18.2Ω) making a final concentration of 50 µg/mL. The solution was filtered through a cellulose acetate membrane (0.45 micron, PALL Life Science) and DLS measurements were performed at 25° C. with a scattering angle of 173°. Zeta potentials were calculated using the Smolokowsky model and measurements were performed in triplicate.

Animals & Ischemia reperfusion (I/R) injury. All procedures involving the animals conformed to the ARVO Statement for the Use of Animals in Ophthalmic and Vision Research. BALB/c albino mice, each weighing ~25 grams, housed in Wilmer animal facility at Johns Hopkins were used for transport as well as I/R studies. All surgeries were performed under ketamine (100 mg/Kg) and Xylazine (10 mg/kg) peritoneal anaesthesia. Six mice were used in each group at each time point. I/R injury was performed in the left eye by following the procedure described elsewhere. Briefly, the anterior chamber was cannulated with 30 gauze needle attached to a line infusing saline. The saline system is mounted on to a custom-made saline reservoir and elevated to certain height (calibrated to 90 mm Hg). The IOP was elevated to 90 mm Hg for 90 minutes and I/R injury and shut off of choroidal circulation was evidenced by blanching of the posterior segment via fundus examination through the operating microscope. After ischemia, the needle was immediately withdrawn for immediate blood reperfusion. The right eye had no I/R injury and served as control.

Dendrimer injection and Animal sacrifice. Six days post I/R injury, BALB/c mice were injected with dendrimer either intravitreally or intravenously. For intravitreal injections, 2 µL containing 20 µg of D-Cy5 was injected using a glass needle aided with a compression injector (Harvard apparatus, Holliston, Mass., USA) into the vitreous chamber. For intravenous injections, 600 µg of D-Cy5 dissolved in 100 µL of sterile PBS was injected via a 30 g needle into the femoral vein after making a small incision in the femoral region. Animals injected with free Cy5 and PBS served as positive or negative controls for this study. At appropriate time points (24 hrs, 72 hrs and 21 days) post dendrimer injections, the animals were anesthetized using ketamine/Xylazine and euthanized using a lethal dose of sodium pentobarbital. The eyes were immediately enucleated and processed for immunohistochemistry analysis.

Immunohistochemistry and confocal microscopy. Eyes were enucleated and fixed in 2% paraformaldehyde (PFA) in PBS. The anterior chamber of the eye was removed and eye cup cryopreserved using previously established protocols (Lutty et al, IOVS, 1993). The eyes were frozen in 20% sucrose with optimum cutting temperature compound (OCT) (Sakura Finetek USA Inc., Torrance, Calif.) in a 1:2 ratio respectfully using dry ice in isopentane. Cryoblocks are stored at −80° C. until sectioned. Eight µm sections were cut from frozen blocks using a cryostatSections were incubated in rabbit anti-Ionised Calcium Binding Adapter 1 molecule (Iba-1) (Wako chemicals, USA), which is a microglia cell marker, and a goat anti-rabbit-Cy3 secondary antibody applied. Sections were analysed on a Zeiss 510 confocal microscope. Excitation and emission wavelengths and laser settings were identical to analyze all tissue in Intravitreal and IV injected animals. Z-stacks of sections were taken and collapsed to give an image through the depth of the whole section.

Conjugation of dendrimer conjugates. Synthesis of the dendrimer triamcinolone acetonide conjugate (D-TA) and Cy5-D-TA is shown in FIG. 4, FIGS. 5A-5C, and FIGS. 6A-6B. The conjugation of dendrimers to Cy5 was done using previously reported methods (Biomaterials. 2012; 33:979-88). This is a convergent method of synthesis and a representative chromatogram is shown in FIGS. 9A-9B.

Biodistribution analysis of D-Cy5 in vital organs. Twelve BALB-C mice weighing ~25 gr BW were used for this study. Four animals were sacrificed at each time point: 24 hours, 72 hours and 21 days. Each mouse was injected via femoral vein with 600 µg of D-Cy5 in 100 µL of sterile PBS. At respective time point, the animals were euthanized and vital organs (heart, lungs, spleen, kidney, liver and eyes) were harvested immediately and organ wet weights were noted. Organs were snap frozen on dry ice, and stored at −80° C. until analysis. Upon analysis, the tissues were thawed and approximately 100-150 mg of tissue were measured and homogenized with 1 ml of MeOH in low DNA binding tubes (Eppendorf AG, Hamburg, Germany) using stainless steel bead and tissue homogenizer (Tissuelyzer LT, QIAGEN, Hilden, Germany) resulting in a pulpy tissue suspension. The suspension was sonicated for 30 minutes and appropriate volumes containing 100 mg of tissue were placed in different low DNA binding vials and diluted with methanol to 1 ml so that the same amount of tissue and same volume was analyzed for each sample. The samples were centrifuged at 10,000 rpm for 10 minutes at 4° C. resulting in supernatants, which were subjected to fluorescence spectroscopy (FLS).

Figures 12A, 12B:
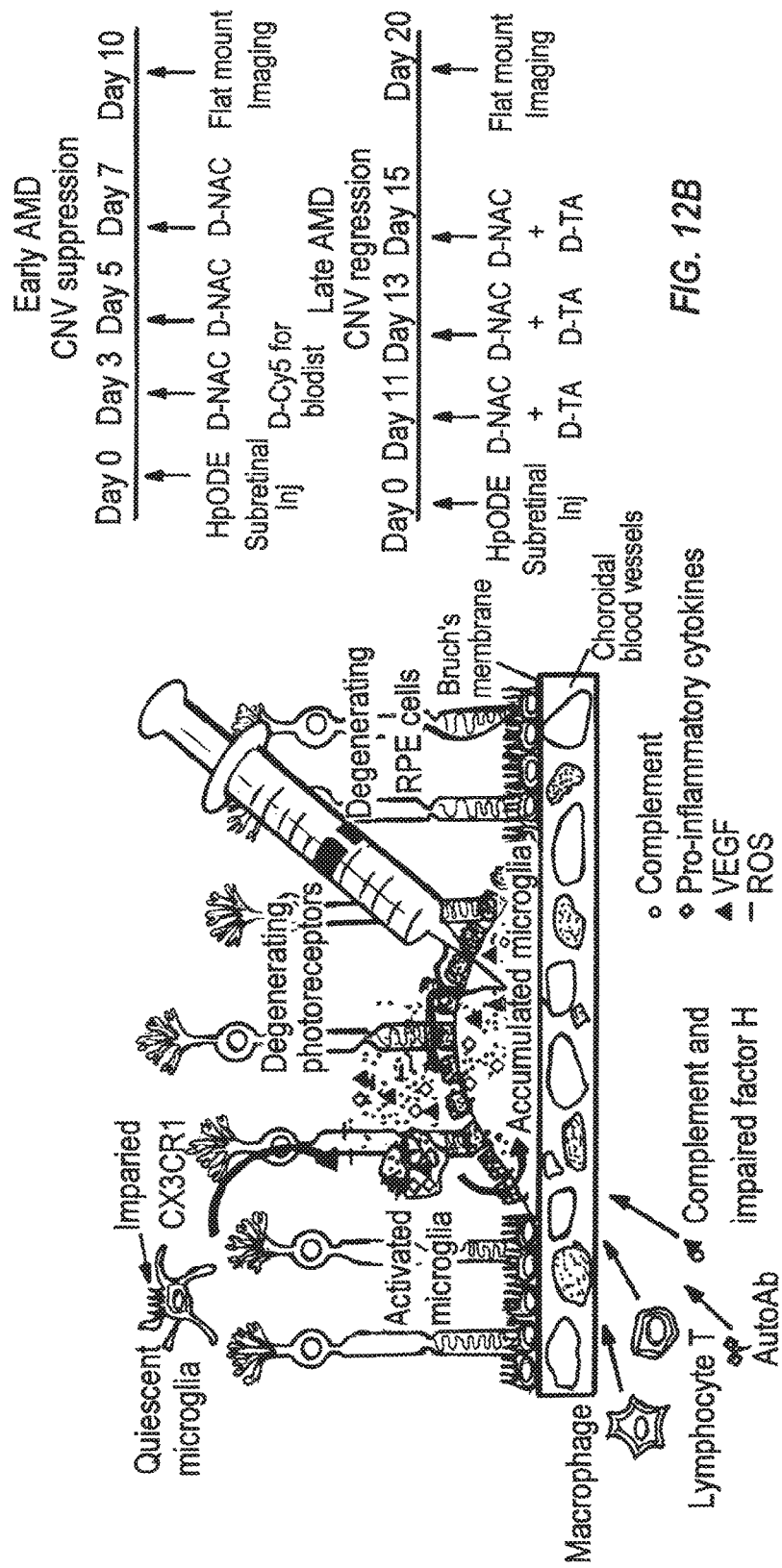
FIG. 12A is an illustration of the rat model of CNV and FIG. 12B are treatment protocols.

CNV rat model. Male SD rats of ~300 grams each were chosen for this study. Lipid 3(S)-hydroperoxy-9Z,11E-octadecadienoic acid (HpODE) (Cayman Chemicals, Michigan, USA.) was dissolved in cold borate buffer at a concentration of 500 µg/33 µL. Two µL of lipid was injected sub-retinal on day 1 forming a bleb in retina. By day 3 the lipid bleb was gone and retinal degeneration began. At day 7 post-lipid injection, neovascularization from choroid (CNV) begins to form and inflammation occurs in retina and choroid as well as neovascularization in retina (RNV). This model causes damage to both choroid and retina and has characteristics of both dry and wed AMD forms (FIG. 12A).

Statistical analysis. The data was analyzed for the reproducibility using Student's t-test to determine the significance between two groups. A p-value equal to or less than 0.05 was considered significant.

Example 1

Characterization of D-Cy5 conjugates. Ethylenediamine-core poly-(amidoamine) [PAMAM] hydroxyl-terminated generation-4 (G4-OH) were labeled with near IR fluorescent dye Cy5 as we reported previously (Molecular Pharmaceutics. 2013; 10:4560-71; Biomaterials. 2012; 33:979-88). Briefly, G4-OH was partially functionalized by 6-amino caproic acid using FMOC protection/deprotection chemistry resulting in bifunctional dendrimers with ~5-6 $NH_2$ groups on their surface. The resulting bifunctional dendrimers with reactive amine groups were reacted with N-hydroxysuccinimide monoester Cy5 dye to obtain the D-Cy5 conjugate. The resulting conjugates were purified using dialysis and GPC (gel permeation chromatgraphy) and characterized using $^1H$ NMR (FIG. 4, FIGS. 5A-5C, and FIGS. 6A-6B).

The HPLC chromatogram of bifunctional dendrimer showed elution time of 14.84 min from the column which differed from the elution time of G4-OH dendrimer (elution time 14.42 min) (FIGS. 9A-9B). This indicates formation of a new compound and that there is only a minor shift in elution time indicating that the structural property of G4-OH dendrimer has not changed significantly. This is also congruent from the DLS results where the approximate size and Zeta potential of G4-OH dendrimer was observed (4.36±0.18 nm and +4.59±0.11 mV respectively). Also, the size and Zeta potential values of bifunctional dendrimer were 4.87±0.20 nm and 6.63±0.24 mV respectively indicating no significant change in size and surface properties of dendrimers. Appearance of a new peak simultaneously in 16.69 min at 647 nm (UV λmax for Cy5) and 645 nm (fluorescence emission of Cy5), which is different from the Cy5 peaks (20.39 min), confirms successful conjugation of dye to the dendrimers.

Example 2

Ischemia-Reperfusion: Differences in microglial/macrophage population, morphology and retinal structural changes. Iba-1$^+$ resident microglia/macrophages in normal retina were less in number and had ramified morphology with distinctive dendrites. The heterogeneous populations of microglial cells were predominately found in choroid and inner nuclear layer (INL) and very few of them were observed in the outer plexiform layer (OPL). Sections from control, non I/R, eyes 24 hours after intravitreal injection were examined Twenty four hours after injection of D-Cy5, there is no dendrimer retained in retina. Free Cy5 was present throughout inner retina and in the inner plexiform layer (IPL). The retinas had a normal lamination after intravitreal injection. I/R injury led to a structurally damaged retina and marked activation of microglia in the retina and choroid, based on a change from dendritic to round or fusiform morphology. At six days post IR, the retinal microglial/macrophages were activated and increased in number and distributed in all retinal layers: inner plexiform layer (IPL), INL, outer nuclear layer (ONL) and the subretinal space. Sections from ischemia/reperfusion eyes 24 hours after intravitreal injection showed Dendrimer-Cy5 (red) is present in Iba-1+ microglia/macrophage; Cy5 or free dye is throughout inner retina and not associated with Iba-1+ microglia. Interestingly, we found decreased numbers of choroidal microglia/macrophages. The IR injury caused collapse of inner retinal layers and retinal detachment from choroid and RPE layers, resulting in folds in retina. We also observed thinning of retinal thickness values, especially the nuclear layers in IR injured retinas when compared to normal retina suggesting neuronal and ganglion cell death.

Example 3

Retinal biodistribution of D-Cy5 upon intravitreal & intravenous administration: Intravitreal Administration.

Intravitreal administration of D-Cy5 showed differential biodistribution between normal and I/R retinas. In normal retinas at 24 hours post intravitreal injection of D-Cy5, there was very minimal fluorescence in retina and choroid. There was no fluorescence signal from D-Cy5 after 24 hours suggesting that dendrimers were cleared completely from retina. On the contrary, free Cy5 remained in inner retina at 24 hours post injection. This suggests that D-Cy5 is cleared rapidly from intact retina. In I/R-injured retinas, we observed significant fluorescence signal from D-Cy5 in retinal sections at 24 hours post-injection. Dendrimers (D-Cy5) were observed in Iba-1+ microglia/macrophages in the subretinal space, ONL, INL and in the vicinity of internal limiting membrane (ILM) of retina. We have also observed dendrimer in vitreous and localized in other cells in inner retina and choroid. At 72 hours post intravitreal injection, D-Cy5 were cleared from other cells and vitreous in I/R eyes. 72 hrs after intravitreal injection, D-Cy5 is still present in microglia and RPE cells in I/R eyes; D-Cy5 was not present in non-I/R control eyes. D-Cy5 was found within Iba-1 labeled cells and retained in microglia/macrophages near the ILM, in inner retina, and sub-retinal space. Interestingly, at 21 days post injection, D-Cy5 was retained specifically in microglial cells in the photoreceptor layer, IPL and near ILM. However, in the case of free Cy5 injected animals, both I/R and normal eyes, Cy-5 can be seen in inner retina and appeared to be concentrated in blood vessels near the ILM but was completely cleared by 72 hours post injection (data not shown).

Example 4

Intravenous administration. D-Cy5, free Cy5 or PBS were injected intravenously through the femoral vein six days after I/R injury in one eye. At respective time points (24 hours, 72 hours and 21 days) post injection, the eyes were enucleated for qualitative assessment of differences in retinal biodistribution of dendrimers between I/R injured and normal retina using IHC. In I/R eyes at 24 hours post intravitreal D-Cy5 administration, D-Cy5 had entered into retina from the circulation and was found within microglia/macrophages throughout retina and in the subretinal space. However, both in normal and I/R eyes 24 hours post free Cy5 dye administration, Cy-5 appeared to be present in retinal blood vessels and choriocapillaris. Free Cy5 was cleared at later time points. Because D-Cy5 was present in choroidal macrophages, it appears that dendrimers can escape the normal choriocapillaris. Interestingly, we did not find any fluorescence signal from D-Cy5 in non-I/R retina indicating the intact blood retinal barrier prevented dendrimer entry. Seventy two hours post intravenous D-Cy5 injection, D-Cy5 were selectively localized and retained in microglia/macrophages in I/R retained in the subretinal space. Even though activated microglial cells were scattered and distributed in all retinal layers, dendrimers were found retained only in microglial cells in choroid, and in the subretinal space. At 21 days post injection, D-Cy5 were retained in a few scattered in retina and choroidal microglial cells. At 21 days, there were relatively fewer Iba-1+ microglial cells with D-Cy5 compared to the 24 hour and 72 hour time point retinas. The microglial cells with D-Cy5 seemed to have reverted back to their ramified morphology but still retained D-Cy5.

Example 5

Figure 3A:
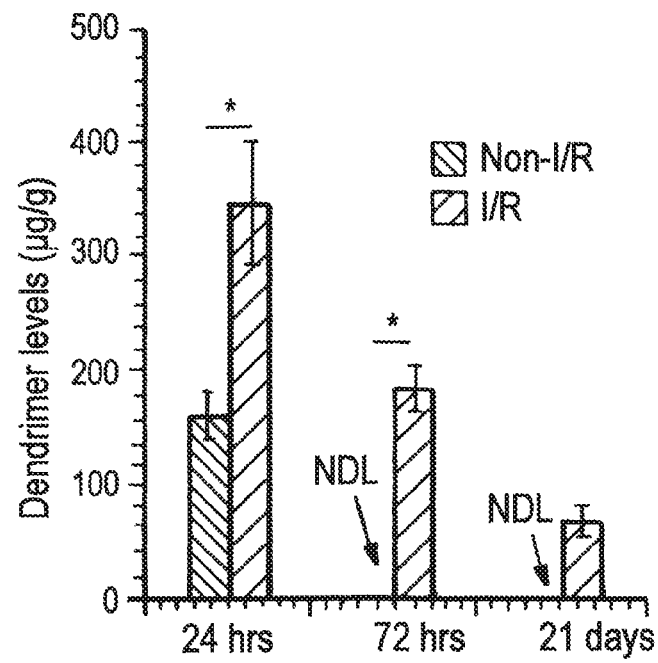
FIGS. 3A-3C show quantification of D-Cy5 levels in posterior eye cups by fluorescence spectroscopy, after extraction of D-Cy5 from tissue.
Figure 3B:
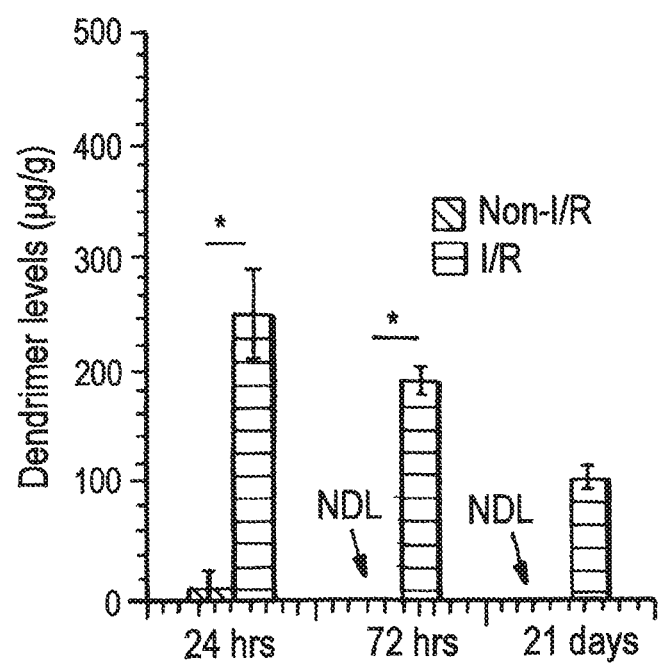
Figure 3C:
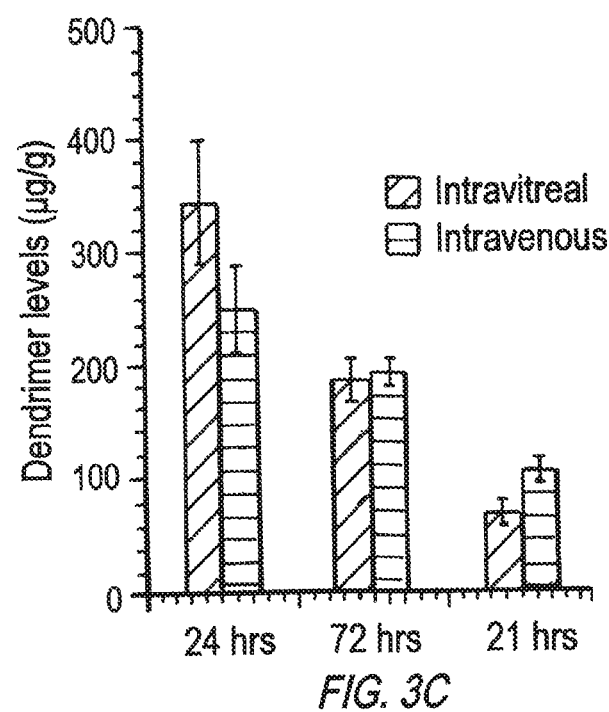
Figure 4:
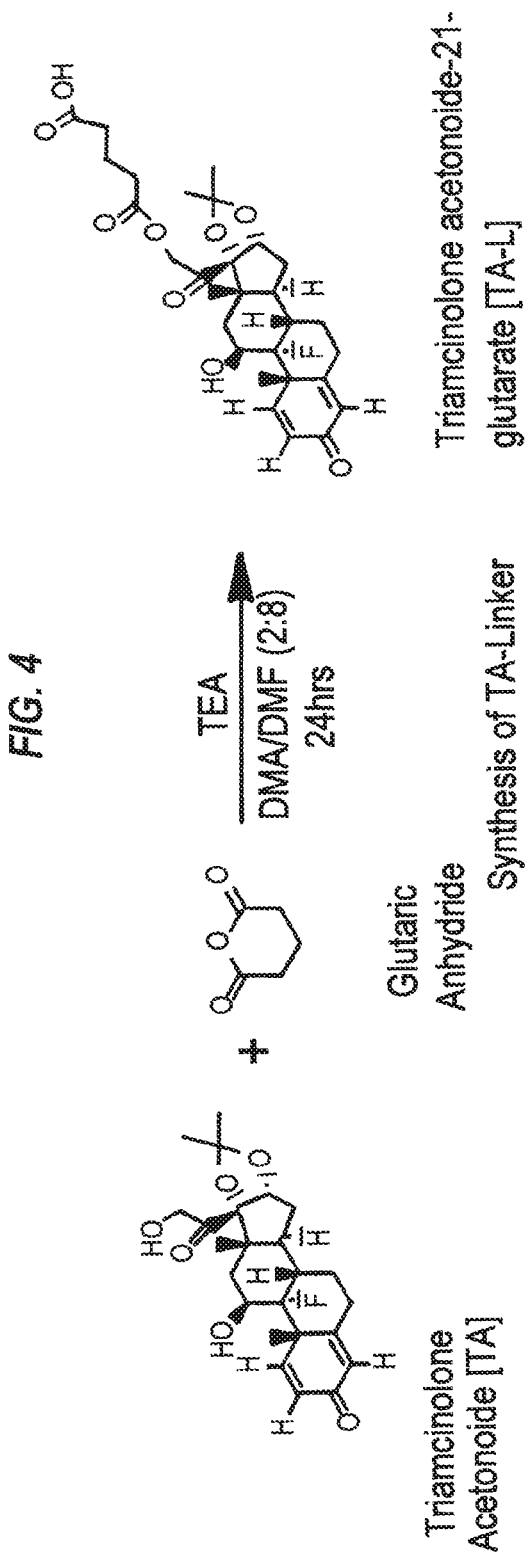
FIG. 4 shows the synthesis of D-TA and Cy5-D-TA conjugates.
Figure 4:
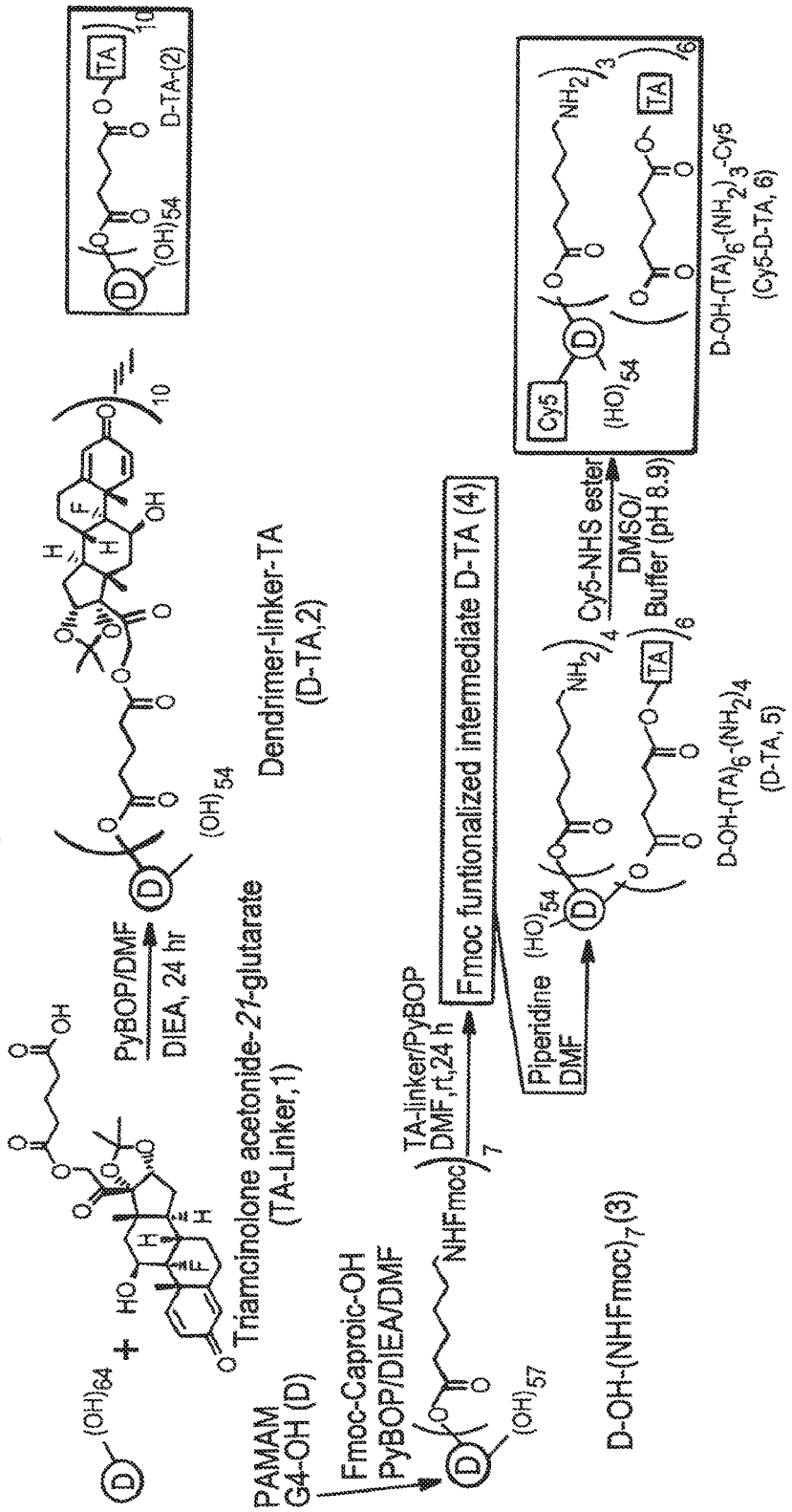
Figure 5A:
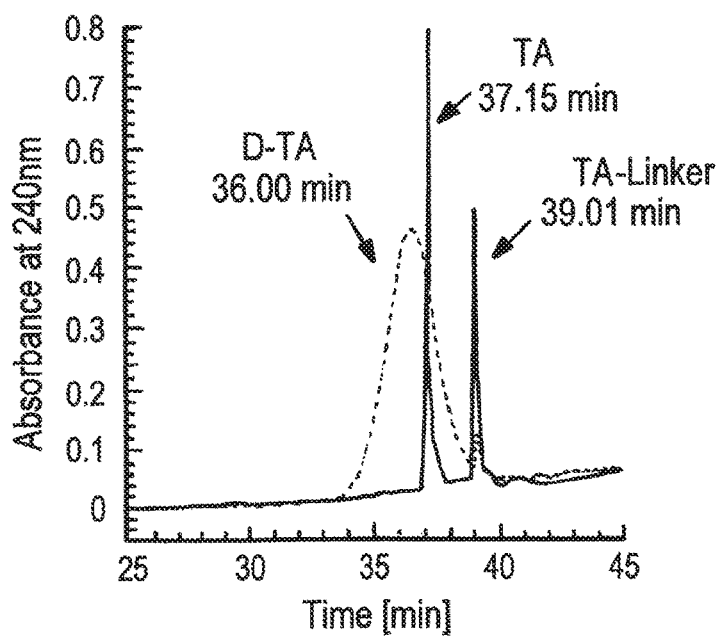
Figure 5B:
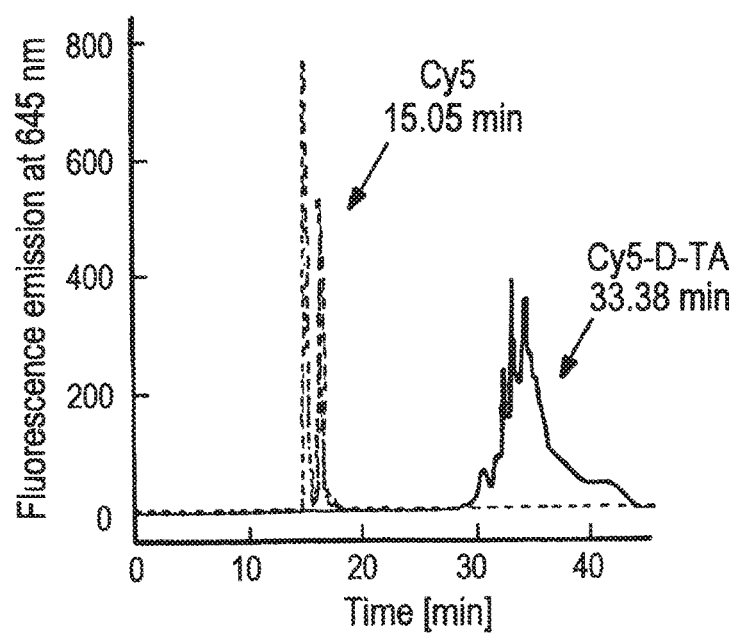
Figure 7B:
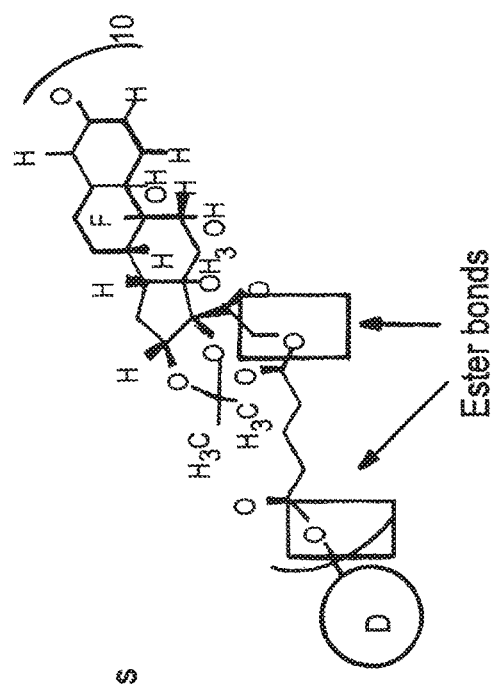
FIGS. 7A-7B the in-vitro release of TA from D-TA in a simulated vitreous humor model.
Figure 7A:
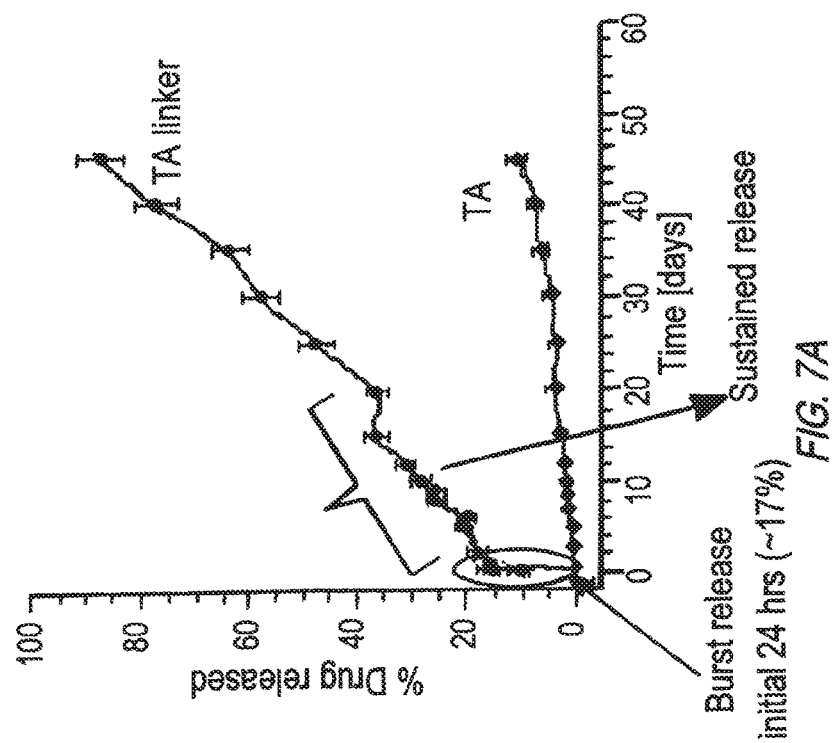

Ocular biodistribution of D-Cy5: intravitreal versus IV. The IV dose of D-Cy5 was 30-fold higher than that of the intravitreal dose. Interestingly, the qualitative uptake and retention pattern in retina was similar after both modes of administration (FIGS. 3A-3C). This demonstrates a relatively low uptake in the healthy control eye, followed by rapid clearance, and a much higher uptake in the fellow I/R eye, and then sustained retention in the I/R eye. In fact, there was no significant difference in quantitative uptake/retention pattern between the two administration modes. Even though there is some choroidal presence after IV D-Cy5 in normal eye, it appears to be mostly cleared within 72 hours. In the I/R eye following IV administration, ~40% of the D-Cy5 uptake observed after 24 hours is retained up to 21 days. For intravitreal administration, ~16% of the D-Cy5 level from 24 hours is retained up to 21 days.

Example 6

Figure 2A:
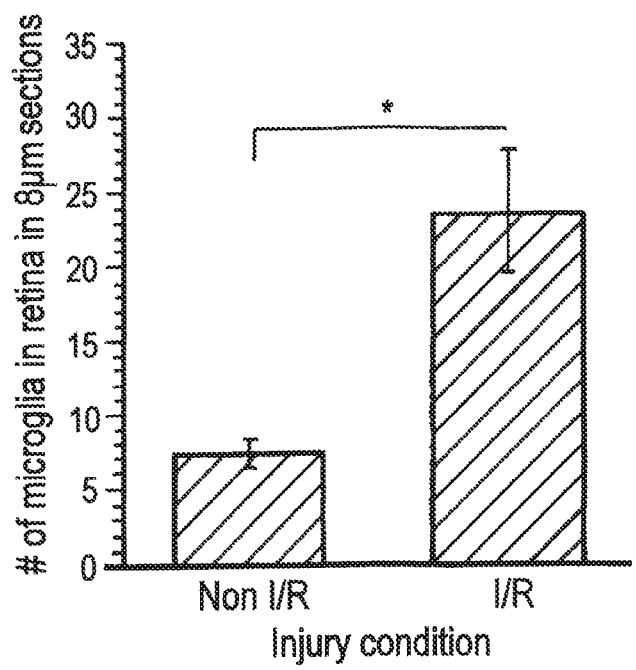
FIGS. 2A-2C show quantification of Iba-1+ cells in retina. Imaris software was trained to count Iba-1$^+$ cells in sections for retina from ora serrate to ora serrata.
Figure 2B:
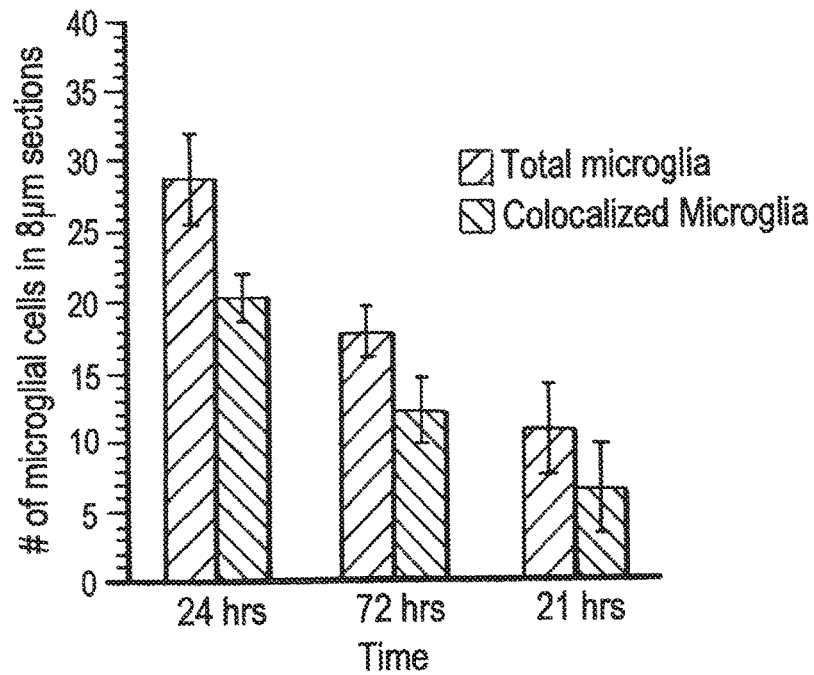
Figure 2C:
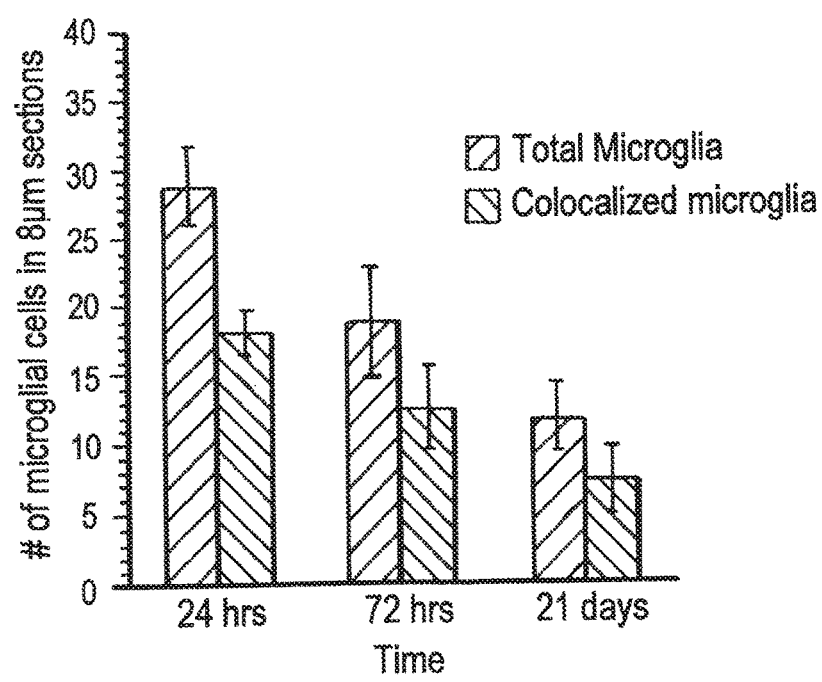

Quantification of Iba-1+ cells and D-Cy5. Imaris software was used to count the number of Iba-1+ cells in 8 mm cryosections from ora *serrata* to ora *serrata*. Four sections from each group were counted. There were significantly more Iba-1+ cells in I/R eyes than non-I/R eyes (FIG. 2A). The software counts not just a single label but cells with two labels colocalizing. Only cell somas would be counted and not delicate processes. We determined that a significant number of Iba-1+ cells had D-Cy5 at all time points with both modes of D-Cy5 delivery (FIGS. 2B-2C) because no cells were double labelled in non-I/R retinas.

Example 7

Quantitative biodistribution of D-Cy5 in vital organs. Quantitative biodistribution in vital organs (liver, kidney, spleen, heart, lungs and serum) and kinetics of D-Cy5 injected intravenously into animals with I/R injury was assessed using FLS (fluorescence spectroscopy) method. For analysis, weight of tissues was measured before being homogenized and D-Cy5 was extracted using methanol as described previously by Lesniak et al. (Molecular pharmaceutics 10 (12), 4560-4571). The D-Cy conjugates were intact stable in human plasma at 37° C. and in vivo, and also the applied methanol extraction protocol yielded best recovery of 96%. The methanol extracts were subjected to fluorescence measurements for emission values using fluorescence spectrophotometer. The amount of D-Cy5 accumulated in each organ was calculated by incorporating the emission values (subtracted background from emission values of respective organs injected with PBS) into the calibration graphs and the values were then back calculated to % of injected dose (ID)/organ using whole organ wet weights.

Figure 8:
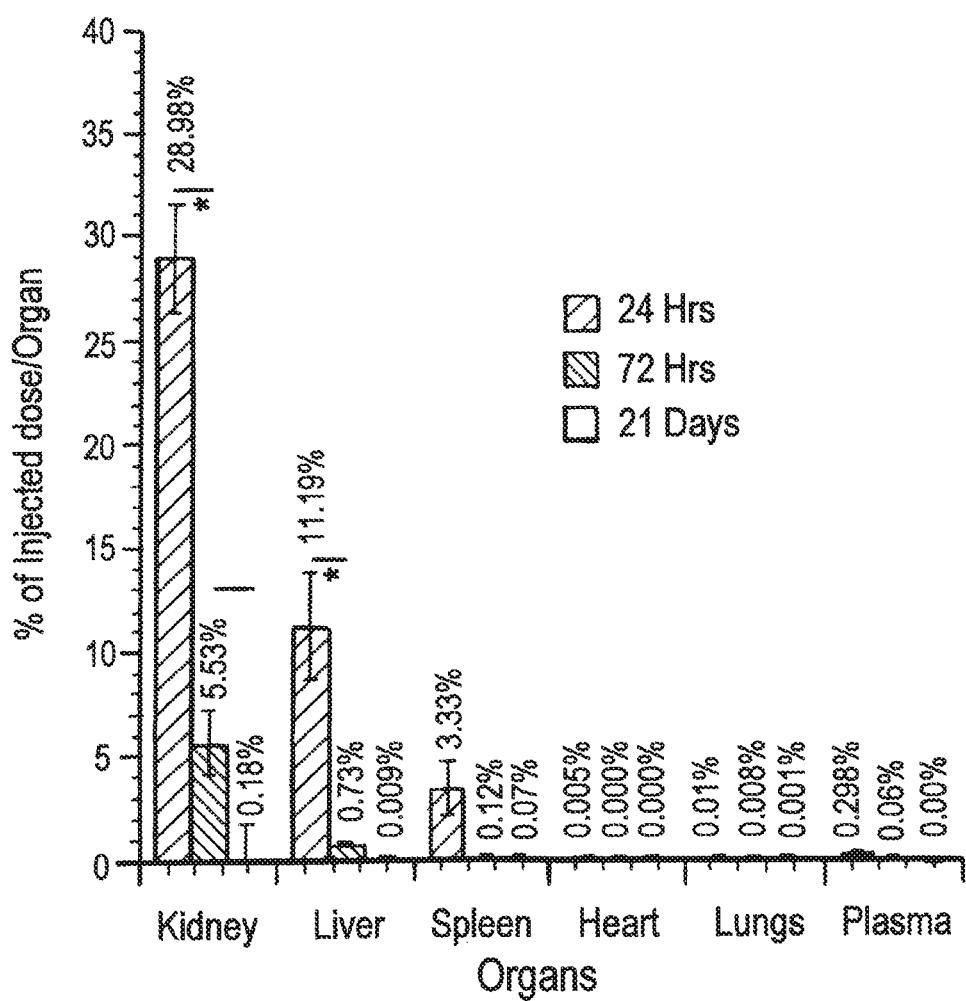
FIG. 8 depicts the biodistribution of D-Cy5 in various organs and clearance with time. The organ uptake was quantified, using D-Cy5 fluorescence measurements, against appropriate calibration curves (n=8). (* indicates p<0.01 when 24 is compared to 72 hr; # indicates p<0.05).

Upon intravenous injection, a percentage of D-Cy5 was immediately cleared out from circulation via urine. We observed that the animals injected with D-Cy5 or free Cy5 urinated deep blue urine within ~5-7 minutes. Twenty four hours post injection, the majority of D-Cy5 was cleared from blood plasma but retained in differential amounts in vital organs (FIG. 8). At 24 hours according to FLS analysis ~0.18% of the injected dose was still in blood. The total blood volume for BALB/C mice is 10.35±0.16 ml/g of tissue.

Figures 10A, 10B, 10C:
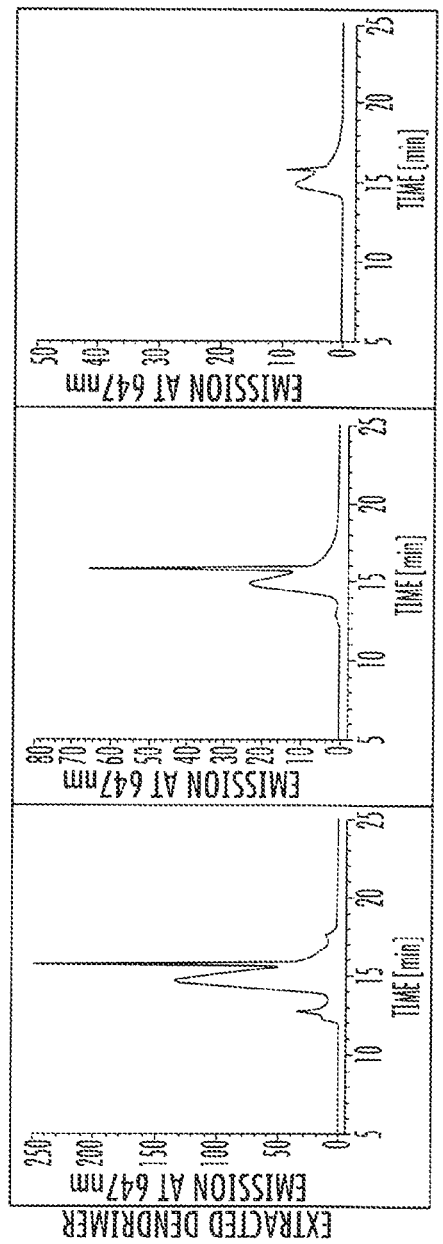
FIGS. 10A-10C show the qualitative assessment of D-Cy5 levels in the kidney as a function of time, using confocal microscopy.

Confocal microscopy analysis of the kidney sections revealed high D-Cy5 signal in the proximal tubules of the kidney cortex at 24 hrs, with this signal decreasing by 72 hrs, which is in good agreement with the biodistribution data. The HPLC of the kidney extracts at 24 hrs showed a small peak from free Cy5 but the major fraction of the peak was D-Cy5 (FIG. 10A). Based on HPLC calibration, we estimate that 12% of the conjugated Cy5 was released by this time, suggesting that the conjugates are mostly intact in-vivo. Hematoxylin and eosin staining of kidney sections from animals injected with D-Cy5 showed no neutrophil or monocyte infiltration, no structural damage, or any signs of toxicity.

The injected D-Cy5 conjugates were cleared but some accumulated in the kidneys. This is in good agreement with the previous results based on fluorescence measurements as described above, and radiolabelling (Drug Deliv Transl Res. 2013 Jun. 1; 3(3):260-271). The D-Cy5 biodistribution and accumulation is as follows: kidney (29.98±2.5%), liver (11.19±2.2), and spleen (3.33±1.26) (FIG. 8). Heart and lungs had minimal accumulation of D-Cy5 (0.0049% and 0.01% respectively). Free Cy5 on other hand was found to be rapidly cleared from blood and had significantly lower accumulation of 0.82±2.93% of the injected dose in kidneys in 24 hours. Moreover, we could not detect any fluorescent signals in other organs indicating the free Cy5 has rapid clearance. At 72 hours post injection, D-Cy5 was cleared from heart, lungs, and spleen but found predominately and persistently retained in kidneys (5.53±1.5%) and to very little extent in liver (0.73±0.026%). Free Cy5 was not detectable in any of the organs indicating that they were either cleared from the body or the amount was below limits of detection (LOD). Twenty one days post injection, dendrimers were completely cleared from all organs examined.

Because there was predominant accumulation of D-Cy5 in kidneys, a qualitative microscopic analysis was done using confocal microscopy. At 24 hours the signal intensity of D-Cy5 channel was high in proximal tubules of the kidney cortex but the signal intensity was decreased in 72 hours kidneys, which is in good agreement with the biodistribution data. The kidney extracts were also analyzed using HPLC to confirm that the fluorescence emission is from D-Cy5 or free Cy5 species. The HPLC chromatograms of the kidney extracts at 24 hours showed a small peak from free Cy5 but the major fraction of the peak was D-Cy5. Twelve % of the conjugated Cy5 was released, based on the calibration graphs of free Cy5, suggesting that the conjugates are somewhat intact in-vivo up to 72 hours. The H and E analysis on these kidney sections (data not shown) show no neutrophil or monocyte infiltration, no structural damage or any signs of toxicity suggesting that the injected D-Cy5 dose did not inflict any toxic effects to organs.

Example 8

Figure 11A:
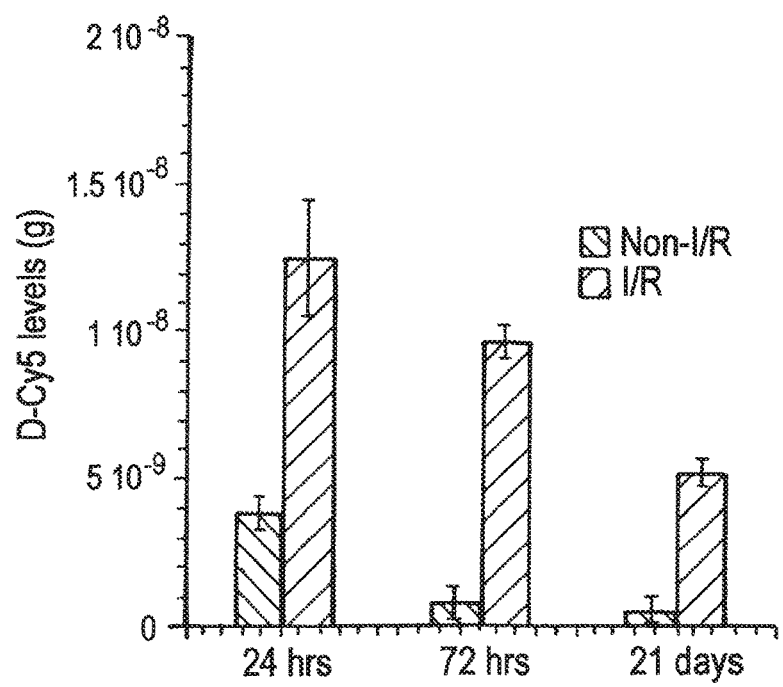
FIGS. 11A-11B are graphs depicting the semi-quantification of dendrimers in posterior eye cup. D-Cy5 was administered either intravenously (FIG. 11A) or intravitreally (FIG. 11B), and quantified both in the injured (I/R) and healthy (non-I/R) eye at 24 hours, 72 hours, 21 days. Significant differences in the uptake between injured and non-injured eye is seen.
Figure 11B:
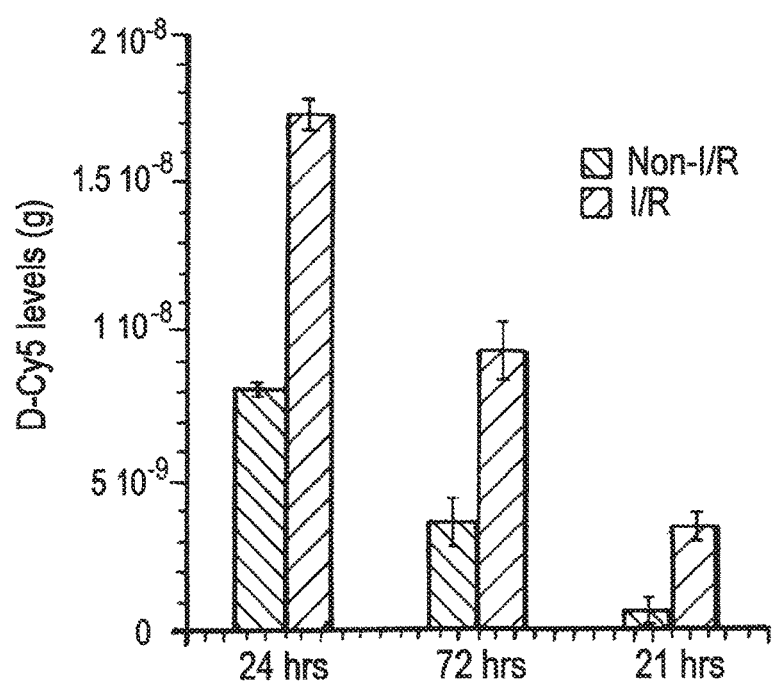

Dendrimer-uptake in the posterior eye-cup. The dendrimer uptake was assessed in the injured and non-injured eyes upon systemic (FIG. 11A) and intravitreal (FIG. 11B, at 30-fold lower doses), using tissue isolation of D-Cy5 and fluorescence quantification. Interestingly, our studies show a significantly higher uptake and retention of the dendrimer in the injured I/R eye, even up to 21 days, post systemic administration. Surprisingly, between 24 hours and 21 days, there appears to be only a 50% drop in the dendrimer level in the injured eye. In contrast, the dendrimer appears to be largely cleared from the healthy eye within 72 hours. The fact that the dendrimers are selectively present in the inflammatory cells, suggests that systemic therapies with dendrimers are viable and sustainable over many weeks. In contrast, small drugs, administered either intravenously and intravitreally are readily cleared from the eye over a short period of time.

Example 9

Effect of N-acetal-Cysteine (NAC) on CNV model. A combination of D-NAC (dendrimer-NAC; 10 mg/kg on a NAC basis) and 6 mg of D-Cy5 were injected intravenously via penile vein on day 3 post lipid injection and animals were sacrificed on day 7 post injection. The animals injected with D-Cy5 and PBS served as controls. The eyes were enucleated immediately after sacrifice and fixed, and retinas and choroids stained with Microglia/Macrophage specific antibody Iba-1, blood vessels stained with GSA lectin and the nuclei were stained with DAPI then viewed as separate flat mounts initially with a Zeiss Meta710 confocal microscope. After flatmount analysis, the tissues were cryopreserved separately and frozen in OCT/20% sucrose. The confocal images choroids of D-NAC treated and control groups were analyzed for CNV area measurements using Image-J software.

Figure 13:
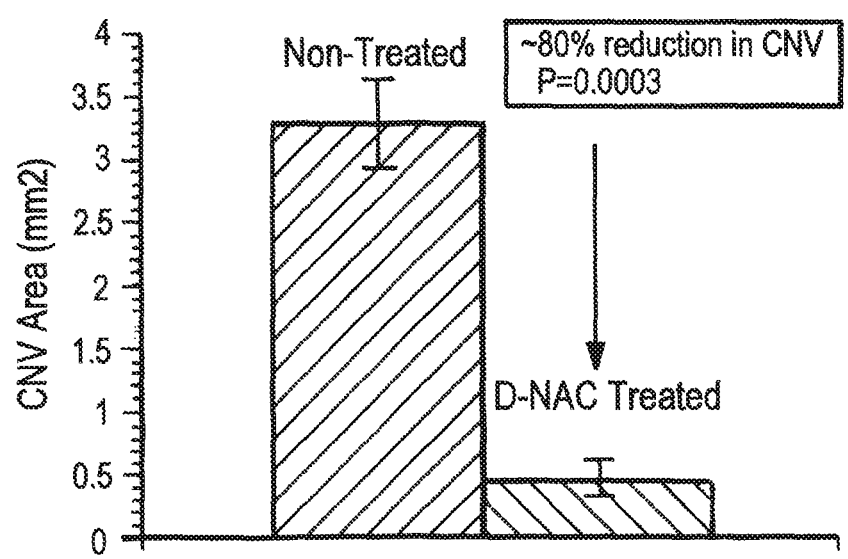
FIG. 13 is a graph depicting the mean CNV areas in non-treated and D-NAC treated choroids in lipid injected rat model. There is a significant reduction ~80% in CNV area in D-NAC treated animals than compared to non-treated animals group. The data was statically analyzed using tailed student t test with Welch correction resulting significant results with p=0.0003 for a sample size n=6.

The image analysis confirmed that lipid injection caused a strong inflammatory response in choroids resulting in the microglial/macrophage (Iba-1 Green) activation, migration and accumulation in CNV area (Iso-lectin blood vessel labeling, Blue). The results suggest that systemically administered dendrimers localized specifically in Iba-1 positive cells in the CNV area (Cy5-Red). The D-NAC+D-Cy5 groups showed therapeutic efficacy in reducing the CNV area when compared to D-Cy5 injected groups. D-NAC (20 mg/kg) was administered systemically, 3 days after lipid-administration, on Day 3, and Day 6, and animals were sacrificed on Day 10. The D-NAC treated animals showed a significant, unexpected reduction in CNV (~80%) (FIG. 13).

Dendrimers can deliver NAC specifically to inflammation causing cells, thereby attenuating them, and which in turn, decreases the VEGF production thus controlling the neovascularization. Retinal inflammation and neovascularization is caused by subretinal injection of lipid. Retinal neovascularization (RNV) formed in the retina showed tortuous abnormal blood vessels stained by Isolectin. Retina flat mount images show that D-Cy5 is up taken by retinal microglia in the inflammation area. It is also evident that the microglial cells are activated due to inflammation caused by the lipid (similar to dry AMD) and the lipid and microglia inducing growth of new blood vessels (similar to wet AMD). We have also observed the migration of microglial cells towards the inflammation area in retina. The RNV area in retinal flatmount indicate that dendrimers (Red) are accumulated in inflammation area and uptaken by microglial cells. We have also observed migration of retinal microglia towards the injured (inflammation) area.

Example 10

Figure 14:
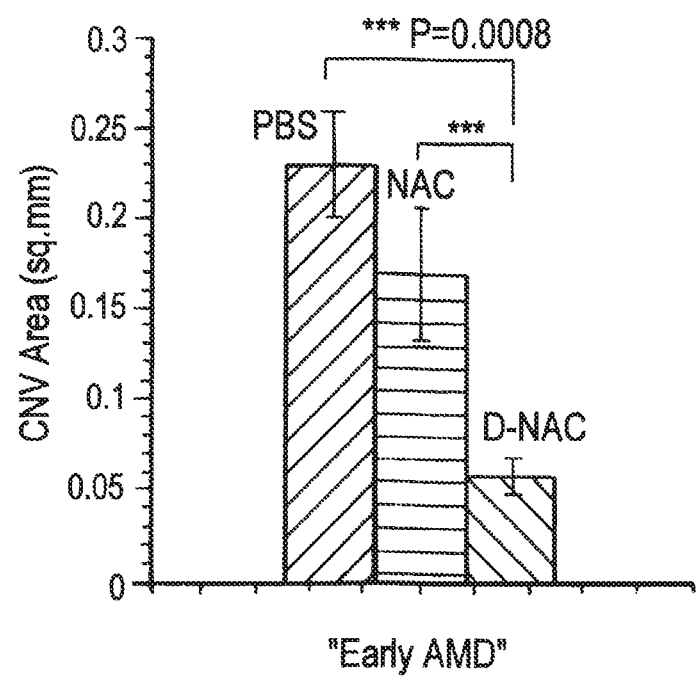
FIG. 14 depicts the effect of systemic free NAC, D-NAC (20 mg/kg on NAC basis), or PBS, on CNV, assessed in a blinded manner, using established choroidal flat mount protocols. D-NAC treated animals showed significant decrease in CNV areas when compared to PBS. Free NAC showed some decrease that was not significant.

Systemically administered D-NAC conjugate suppresses CNV, when administered early. D-NAC was administered on Day 3 (two days after lipid administration), and on day 5 and day 7 at 20 mg/kg on a NAC basis. D-NAC caused significant suppression of CNV when assessed on Day 10 compared to free NAC at equivalent doses, and untreated controls (~78% suppression compared to PBS, n=12 eyes, p<0.001). As shown in FIG. 14, the effect of systemic free NAC, D-NAC (20 mg/kg on NAC basis), or PBS, on CNV, was assessed in a blinded manner, using established choroidal flat mount protocols. D-NAC treated animals showed significant decrease in CNV areas when compared to PBS. Free NAC showed some decrease that was not significant. CNV areas were assessed using morphometric analysis (yellow delineation) in Image-J software. FIG. 14 shows the PBS choroid with larger CNV and increased population of macrophages (green) in the bleb area, whereas the flatmount shows the efficacy of D-NAC with reduced CNV and macrophage accumulation. The vasculature was stained with GSA lectin (blue), and macrophages are stained with IBA-1 (Green). Values were analyzed using Mann-Whitney t-test with n=12 and P<0.001

Example 11

Figure 15:
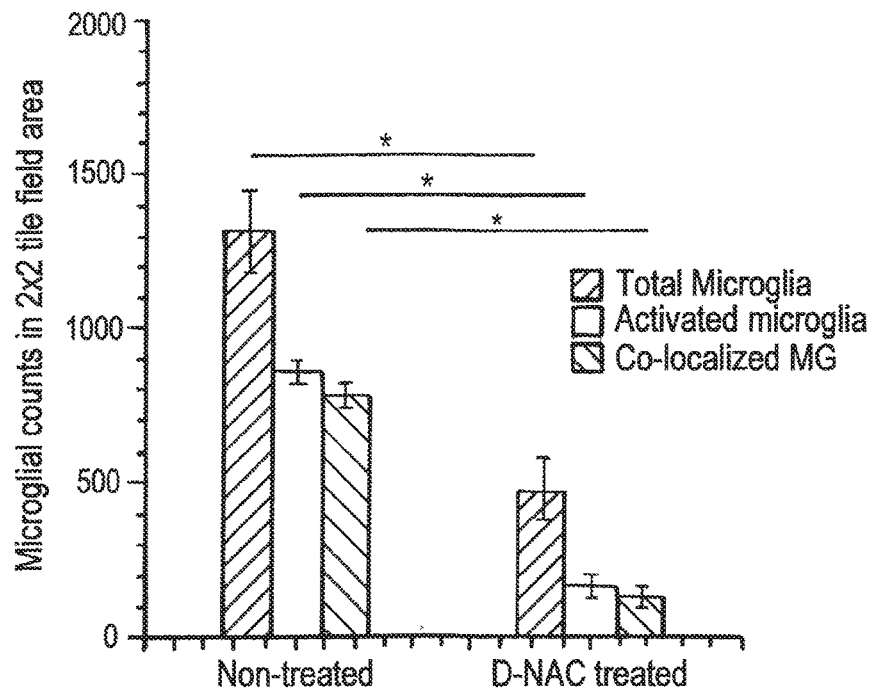
FIG. 15 shows flat mount image analysis of (20× magnification) of choroids for macrophage accumulation in the bleb area surrounding the CNV. Macrophages were stained with IBA-1 (Green) and D-Cy5 is red. Macrophage cell count analysis showed a ~63% reduction in number of macrophages cells, and a ~60% reduction in activated macrophages upon D-NAC compared to PBS treatment, with near 90%+colocalization of activated macrophages and dendrimers. The cell count analysis were done using Imaris (Bitplane) software using surface function with smoothing factor and cell size threshold of 8-12 µm diameter with split function. Activated and resting macrophages were counted based on cell shape (amoeboid versus ramified) using cell surface to volume ratio with sphericity of 0.758 add ellipiticity function 0.298 as threshold. Colocalization of D-Cy5 was assessed using spot function. N=6 eyes for each group, 3 areas/choroid were analyzed, and averaged.

Systemic D-NAC reduces macrophage migration to the CNV area, and attenuates choroidal inflammation. The extent of macrophage depletion in the CNV region, upon systemic D-NAC therapy at 20 mg/kg NAC was assessed on Day 10, using IBA-1 staining. A significant reduction in total macrophages accumulation (63%) was seen upon D-NAC therapy. Previous studies by Ambati and coworkers showed that macrophage depletion correlated with CNV reduction. Interestingly, morphological analysis using Imaris71 suggested that there was an 80% reduction in activated macrophages, and ~90% of these activated macrophages contained D-Cy5 (in both PBS and D-NAC treated animals), indicating selectivity (FIG. 15).

Example 12

Figure 16A:
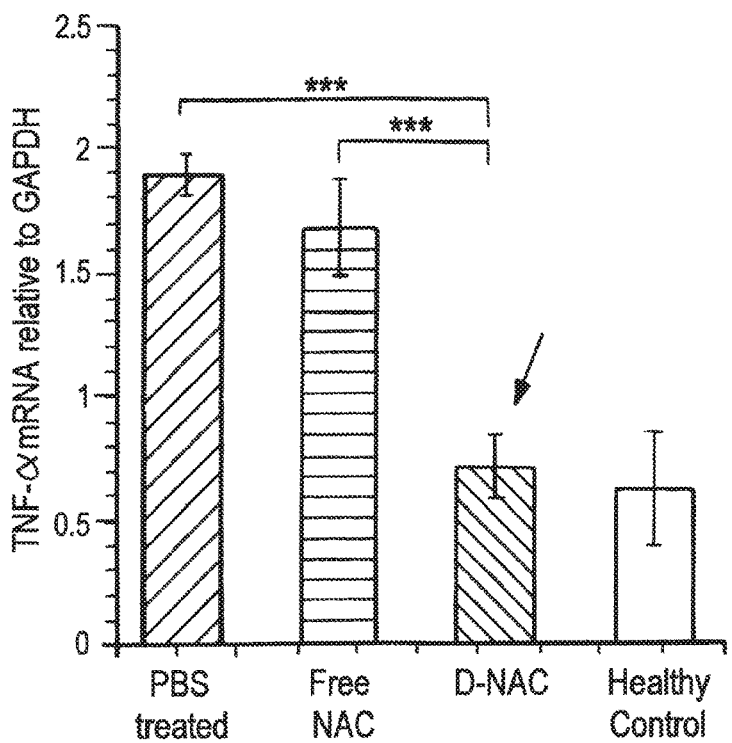
FIGS. 16A-16C depict that the choroids from the different groups were analyzed using ELISA (n=8 choroids/group). While free NAC was not effective compared to controls, D-NAC showed significant attenuation of pro-inflammatory cytokines (FIGS. 16A-16B). *** denotes p<0.001. D-NAC also enhanced anti-inflammatory IL-10 (FIG. 16C) * denotes p <0.01.
Figure 16B:
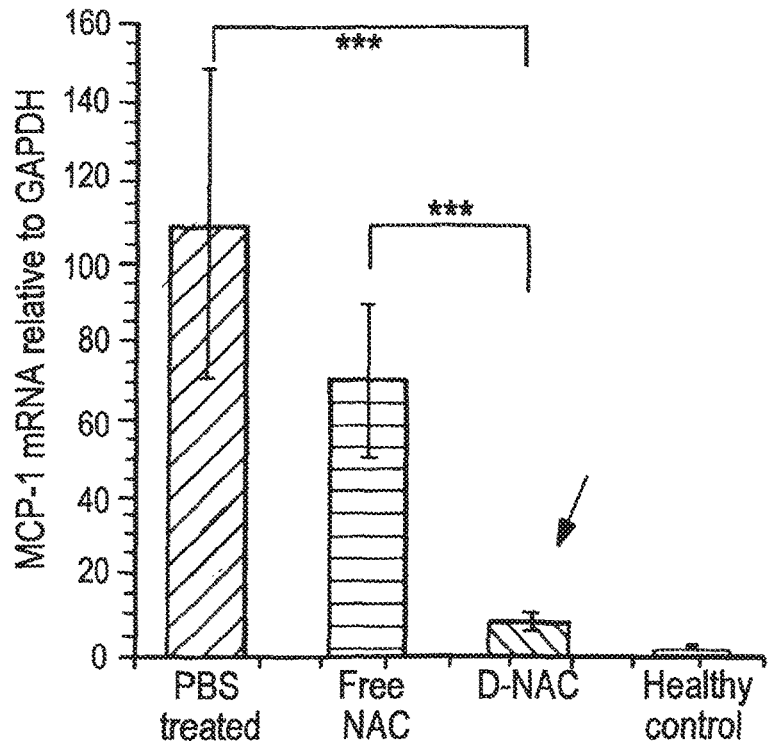
Figure 16C:
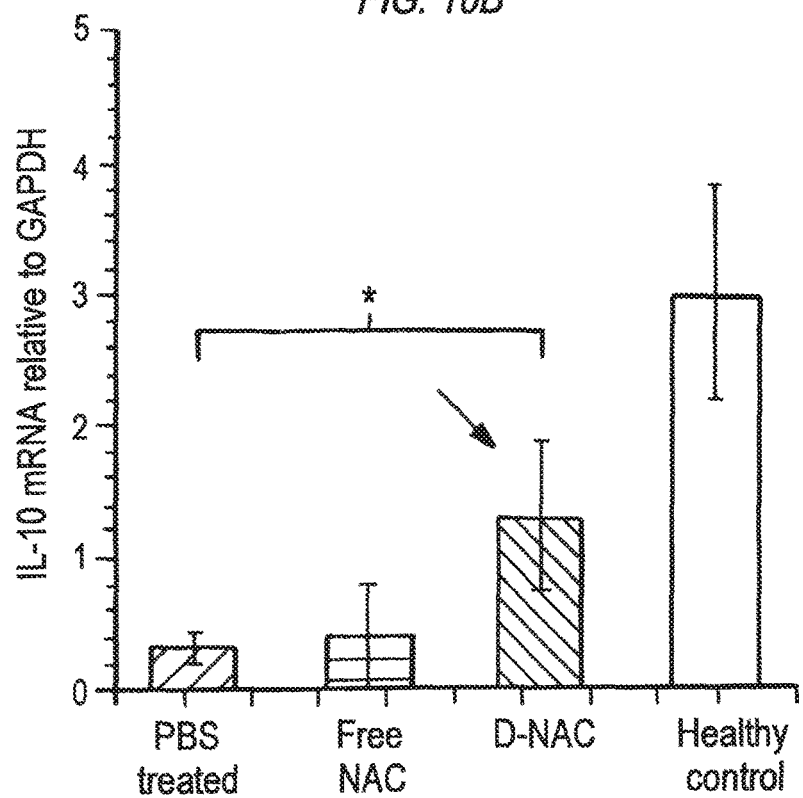
Figure 17:
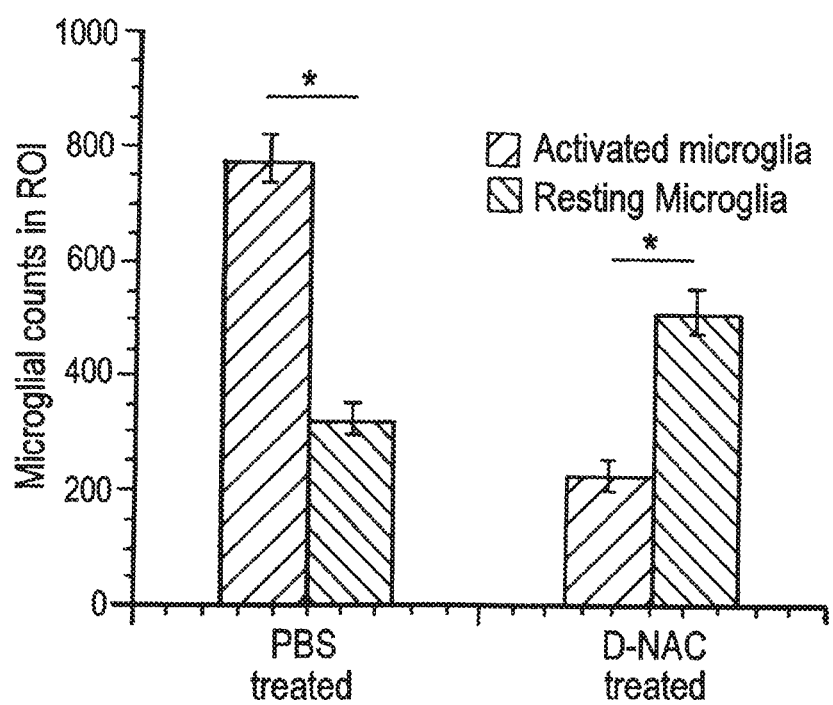
FIG. 17 is a bar graph showing retinal microglial counts in the retina for PBS and D-NAC treatment. The D-NAC treatment reverses the activated microglia phenotype.

The effect of D-NAC choroidal inflammation was assessed in a blinded manner, by measuring proinflammatory (IL-1β, IL-6, MCP-1-monocyte chemoattractant, and TNFα) and anti-inflammatory cytokine levels (IL-10). 10,23,72 There was a significant reduction in all the proinflammatory cytokines, which returned to levels seen in healthy controls, whereas free NAC was not effective (FIGS. 16A-16B). Interestingly, D-NAC appeared to enhance the anti-inflammatory cytokine IL-10 (FIG. 16C). This suggests that selective attenuation of proinflammatory response can be achieved with D-NAC.

Example 13

Systemic dendrimer targets retinal mi/ma, and D-NAC attenuates retinal inflammation. Pathological area of the same retina near the bleb shows abnormal vessels, activated mi/ma ('round' and amoeboid) and 'spiked' dendrimers co-localized in activated mi/ma. Similar to the biodistribution pattern seen in the CNV area, the D-Cy5 localized selectively in the activated mi/ma in the bleb area, but did not localize in the unaffected areas of the same retina. In D-NAC treated retina, there was a reduction in the number of mi/ma in the bleb area, and which were more ramified with less D-Cy5 uptake.

Figure 18A:
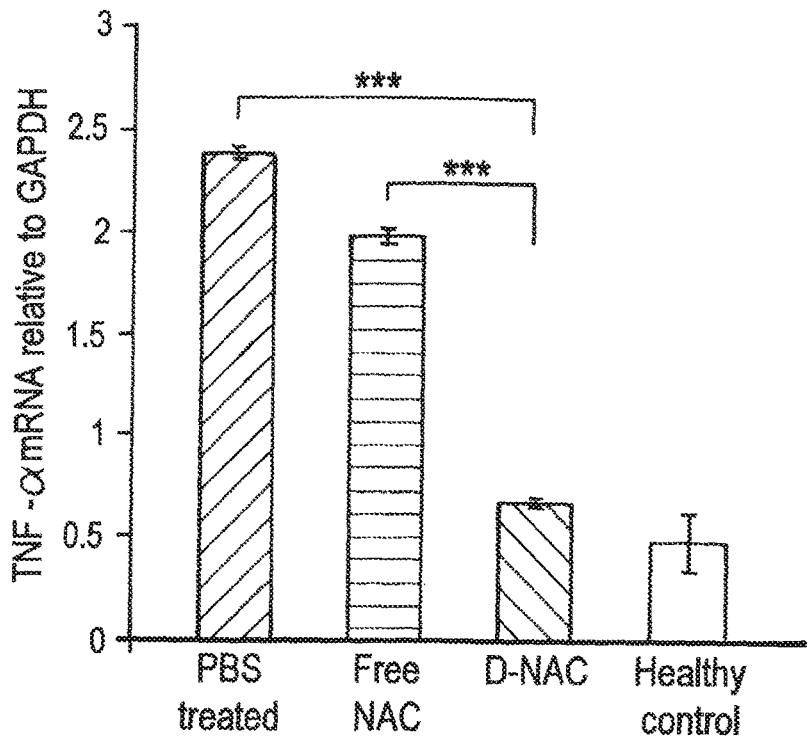
FIGS. 18A-18C show the results from the retinas from the different groups analyzed by ELISA (n=8/group). While free NAC was not effective compared to PBS, D-NAC showed significant attenuation of pro-inflammatory cytokines (FIG. 18A: TNF-a.
Figure 18B:
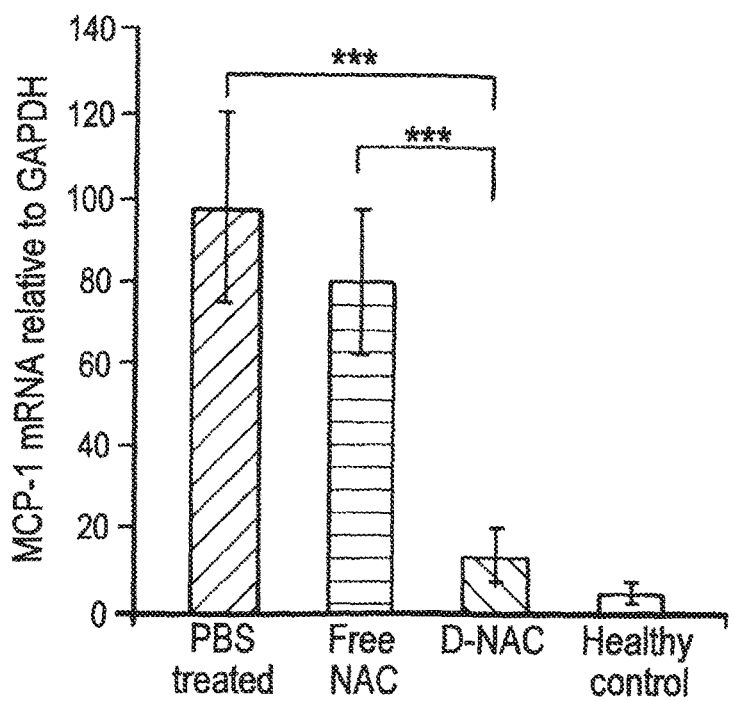
Figure 18C:
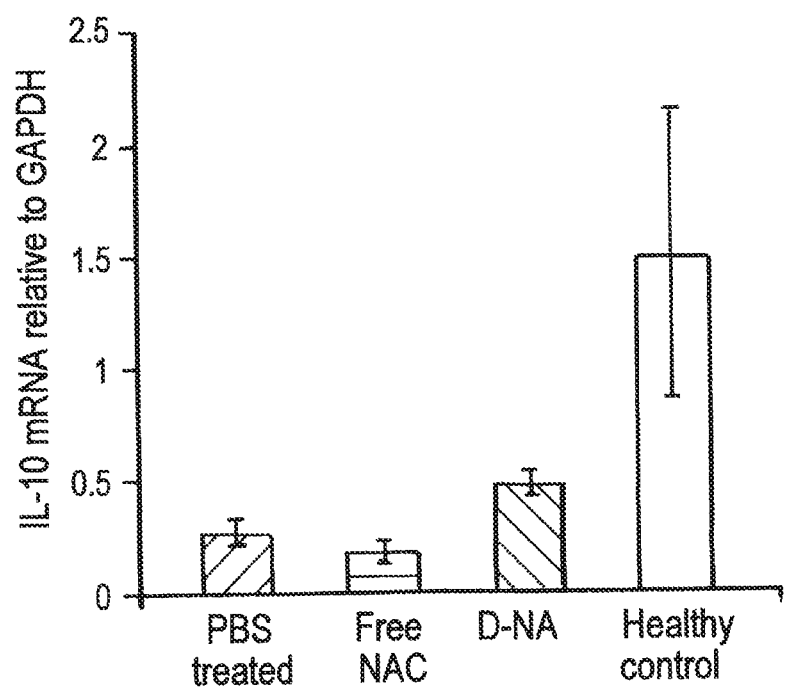

The effect of D-NAC on retinal inflammation was assessed in a blinded manner, by measuring proinflammatory (IL-1β, IL-6, MCP-1, and TNFα) and anti-inflammatory (IL-10) cytokine levels. There was a significant reduction in all the proinflammatory cytokines, which returned to levels seen in healthy controls, whereas free NAC was not effective (FIGS. 18A-18C). Interestingly, D-NAC appeared to enhance the anti-inflammatory cytokine IL-10 (FIG. 18C). This suggests that selective attenuation of proinflammatory response can be achieved with D-NAC.

Example 14

Figure 19:
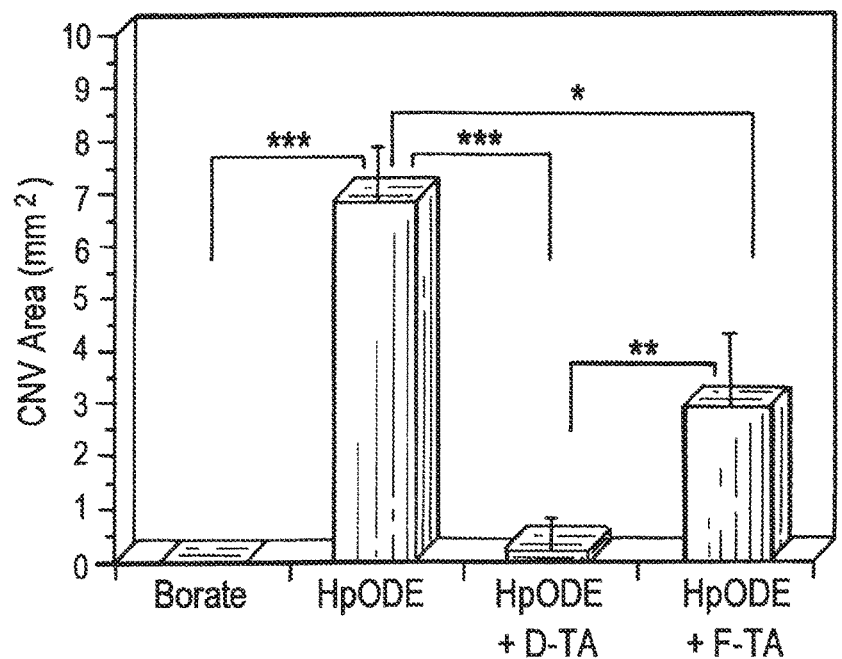
FIG. 19 shows the effect of TA on CNV suppression.
Figure 20:
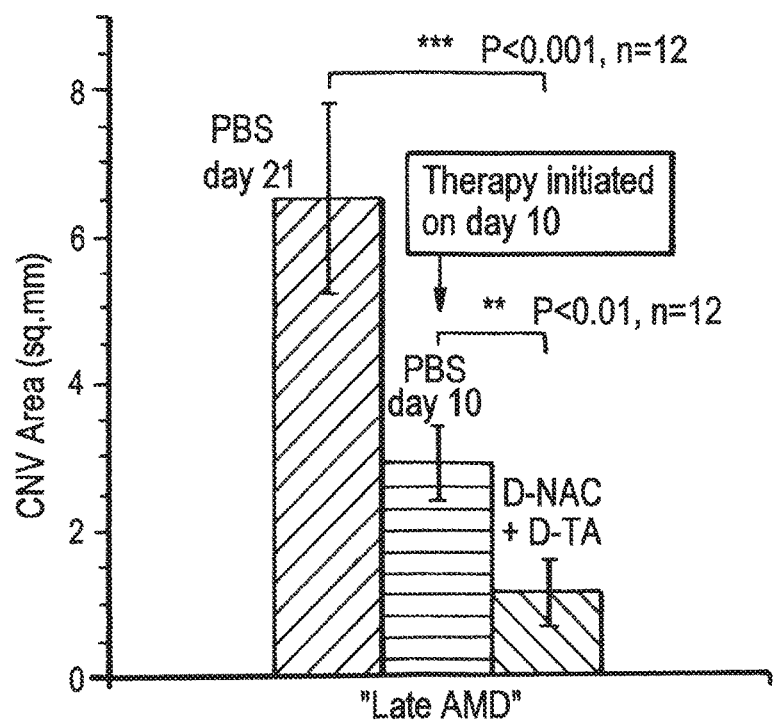
FIG. 20 shows preliminary CNV area analysis of D-NAC+D-TA treated choroids: On Day 21, PBS-treated choroids show significantly larger CNV area with fully formed irregular blood vessels compared to D-NAC choroids treated on Day 11, suggesting effectiveness for late AMD. On Day 21, the D-NAC treated (on Day 11) choroids show a lower CNV area compared to PBS choroids on Day 10, suggesting regression.

Systemic combination therapy with D-NAC and D-TA, results in CNV regression. A combination of D-NAC (20 mg/kg on NAC basis) and D-TA (10 mg/kg on TA basis) was administered systemically at a later stage (on Day 11, Day 13 and Day 15) to assess the efficacy when significant CNV has already occurred: (1) On Day 21, there was a 72% reduction in CNV in dendrimer-treated animals, compared to PBS controls, suggesting that late treatment is effective; (2) Compared to the extent of CNV area on Day 10, there was a 45% reduction in dendrimer-treated animals on Day 21, showing strong suggestions of CNV regression (FIGS. 19-20). These pilot results (n=3) suggest that significant CNV suppression may be possible with systemic therapies delivered with dendrimers. The systemic combination therapy did not lead to any increase in IOP, or any systemic toxicity assessed from histology. Moreover, both intravitreal and systemic administration of the inventive compositions had similar retinal biodistribution and effect in injured retinas, meaning the systemic administration is a viable alternative to intravitreal injection.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating an inflammatory and/or angiogenic disease in the eye of the subject in need thereof, comprising injecting for systemic delivery a dendrimer composition in an effective amount to treat the inflammatory and/or angiogenic disease in the eye of the subject,
    wherein the dendrimer composition comprises hydroxyl-
        terminated poly(amidoamine) (PAMAM) dendrimers covalently linked to one or more therapeutic agents, which can be the same or different.

2. The method of claim 1, wherein the dendrimers are included in a formulation comprising liposomes, microcapsules, nanoparticles, or nanocapsules.

3. The method of claim 1, wherein the PAMAM dendrimer is a G3, G4, G5, G6, G7, G8, G9 or G10 PAMAM dendrimer.

4. The method of claim 1, wherein the inflammatory disease of the eye is selected from the group consisting of age-related macular degeneration (AMD), retinitis pigmentosa, optic neuritis, infection, uveitis, sarcoid, sickle cell disease, retinal detachment, temporal arteritis, retinal ischemia, arteriosclerotic retinopathy, hypertensive retinopathy, retinal artery blockage, retinal vein blockage, hypotension, diabetic retinopathy, macular edema, and choroidal neovascularization.

5. The method of claim 1, wherein the dendrimer composition is repeatedly administered to the subject daily, weekly, biweekly, monthly, or bimonthly.

6. The method of claim 1, wherein the one or more therapeutic agents are selected from the group consisting of proteins, oligonucleotides, and small molecules.

7. The method of claim 6, wherein the one or more therapeutic agents are selected from the group consisting of vitamin A, vitamin C, vitamin E, and beta-carotene.

8. The method of claim 6, wherein the one or more therapeutic agents are anti-inflammatory agents selected from the group consisting of triamcinolone acetonide, methyl prednisone, dexamethasone, COX-2 inhibitors, gold compound anti-inflammatory agents, salicylate anti-inflammatory agents, N-acetyl cysteine, minocycline, aflibercept, rapamycin, and anti-VEGF agents.

9. The method of claim 6, wherein the one or more therapeutic agents are antibodies selected from the group consisting of daclizumab, basiliximab, ranibizumab, and pegaptanib sodium.

10. The method of claim 6, wherein the one or more therapeutic agents are selected from the group consisting of enzymes, receptor antagonists or agonists, hormones, growth factors, and antibodies.

11. The method of claim 6, wherein the oligonucleotides are selected from the group consisting of siRNAs, and microRNAs.

12. The method of claim 1, wherein the composition is administered in combination with one or more additional therapeutically active agents.

13. The method of claim 1, wherein the composition is administered intravenously.

* * * * *

UNITED STATES PATENT AND TRADEMARK OFFICE
CERTIFICATE OF CORRECTION

PATENT NO. : 10,369,124 B2
APPLICATION NO. : 15/307284
DATED : August 6, 2019
INVENTOR(S) : Kannan Rangaramanujam et al.

Page 1 of 1

It is certified that error appears in the above-identified patent and that said Letters Patent is hereby corrected as shown below:

On the Title Page

Item (72) Inventors, please replace "Manof Mishra" with "Manoj Mishra".

In the Specification

Column 1, Line 13, please insert the following paragraph
--STATEMENT REGARDING FEDERALLY SPONSORED RESEARCH
This invention was made with government support under, EY025304 awarded by the National Institutes of Health. The government has certain rights in the invention.--.

In the Claims

Column 20, Line 62, please replace the phrase "the subject" with "a subject".

Signed and Sealed this
Fourth Day of August, 2020

Andrei Iancu
*Director of the United States Patent and Trademark Office*